(12) United States Patent
Suzuki et al.

(10) Patent No.: US 8,986,857 B2
(45) Date of Patent: Mar. 24, 2015

(54) DIBENZO[C,G]CARBAZOLE COMPOUND, LIGHT-EMITTING ELEMENT, LIGHT-EMITTING DEVICE, DISPLAY DEVICE, LIGHTING DEVICE AND ELECTRONIC DEVICE

(75) Inventors: Hiroki Suzuki, Kanagawa (JP); Satoshi Seo, Kanagawa (JP); Sachiko Kawakami, Kanagawa (JP); Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 383 days.

(21) Appl. No.: 13/548,684

(22) Filed: Jul. 13, 2012

(65) Prior Publication Data

US 2013/0020561 A1 Jan. 24, 2013

(30) Foreign Application Priority Data

Jul. 22, 2011 (JP) .................................. 2011-161161

(51) Int. Cl.

| H01L 51/50 | (2006.01) |
|---|---|
| H01L 51/00 | (2006.01) |
| C07D 209/60 | (2006.01) |
| C09K 11/06 | (2006.01) |
| H05B 33/14 | (2006.01) |

(52) U.S. Cl.
CPC .......... *H01L 51/0072* (2013.01); *C07D 209/60* (2013.01); *C09K 11/06* (2013.01); *H05B 33/14* (2013.01); *H01L 51/006* (2013.01); *H01L 51/5012* (2013.01); *C09K 2211/1007* (2013.01); *C09K 2211/1011* (2013.01); *C09K 2211/1029* (2013.01); *Y10S 428/917* (2013.01)
USPC ........... 428/690; 428/917; 313/504; 313/505; 313/506; 257/40; 257/E51.05; 257/E51.026; 257/E51.032; 548/304.1; 548/418; 548/440; 548/444; 546/18; 546/79; 546/81; 546/101

(58) Field of Classification Search
None
See application file for complete search history.

(56) References Cited

U.S. PATENT DOCUMENTS

| 8,084,146 B2 | 12/2011 | Murase et al. |
| 8,183,793 B2 | 5/2012 | Egawa et al. |
| 2003/0186077 A1 | 10/2003 | Chen |
| 2007/0247063 A1 | 10/2007 | Murase et al. |
| 2008/0107918 A1 | 5/2008 | Egawa et al. |
| 2008/0122344 A1 | 5/2008 | Shin et al. |
| 2012/0138907 A1 | 6/2012 | Murase et al. |

FOREIGN PATENT DOCUMENTS

| CN | 1984897 | 6/2007 | |
|---|---|---|---|
| CN | 101506163 A | 8/2009 | |
| EP | 1 748 045 A1 | 1/2007 | |
| EP | 2 450 356 A1 | 5/2012 | |
| KR | 10-2008-0047210 | 5/2008 | |
| KR | 10-2010-0108924 | 10/2010 | |
| TW | 200609328 | 3/2006 | |
| TW | 201105774 | 2/2011 | |
| WO | WO 03/059014 A1 | 7/2003 | |
| WO | WO 2005/113531 A1 | 12/2005 | |
| WO | WO 2008/026614 A1 | 3/2008 | |
| WO | WO 2010/107244 * | 9/2010 | ............. C09K 11/06 |
| WO | WO 2010/114264 A2 | 10/2010 | |
| WO | WO 2011/010842 A2 | 1/2011 | |

OTHER PUBLICATIONS

Zander et al., "Notiz uber die Dehydrierung von Di-β-naphthylamin and Di-β-anthrylamin mit Kupferpulver," Chemische Berichte, 1964, vol. 97, No. 1, pp. 304-306.
International Search Report for WO application No. PCT/JP2012/068049; mailing date Sep. 25, 2012.
Written Opinion of the International Searching Authority for WO application No. PCT/JP2012/068049, mailing date Sep. 25, 2012.
Zander.M et al., "Notiz uber die Dehydrierung von Di-β-naphthylamin und Di-β-anthrylamin mit Kupferpulvr", Chemische Berichte, 1964, vol. 97, No. 1, pp. 304-306.
Chinese Office Action re Application No. CN 201310063019.6, dated Nov. 15, 2013.
Goldsmith, C.R. et al., "C-H Bond Activation by a Ferric Methoxide Complex: Modeling the Rate-Determining Step in the Mechanism of Lipoxygenase," J. Am. Chem. Soc., vol. 124, No. 1, 2002, pp. 83-96.
Onishi, T. et al., "A Method of Measuring an Energy Level," High Molecular EL Materials-Development of Light-Emitting High Molecular Compounds, Kyoritsu Shuppan, Dec. 25, 2004, pp. 64-67 (with English translation, pp. 1-3).
Chinese Office Action re Application No. CN 201280002032.4, dated Jan. 28, 2015.

* cited by examiner

Primary Examiner — Gregory Clark
(74) Attorney, Agent, or Firm — Husch Blackwell LLP

(57) ABSTRACT

Provided is a novel compound which can be used for a transport layer or as a host material or a light-emitting material in a light-emitting element and with which a high-performance light-emitting element can be manufactured. A dibenzo[c,g]carbazole compound in which an aryl group having 14 to 30 carbon atoms and including at least anthracene is bonded to nitrogen of a dibenzo[c,g]carbazole derivative is synthesized. By use of the dibenzo[c,g]carbazole compound, a light-emitting element having very good characteristics can be obtained.

21 Claims, 25 Drawing Sheets

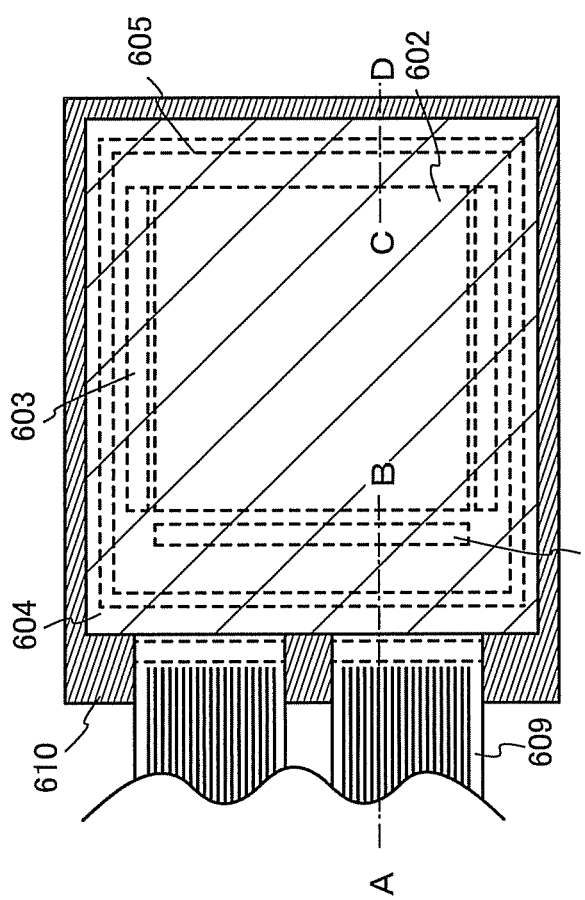
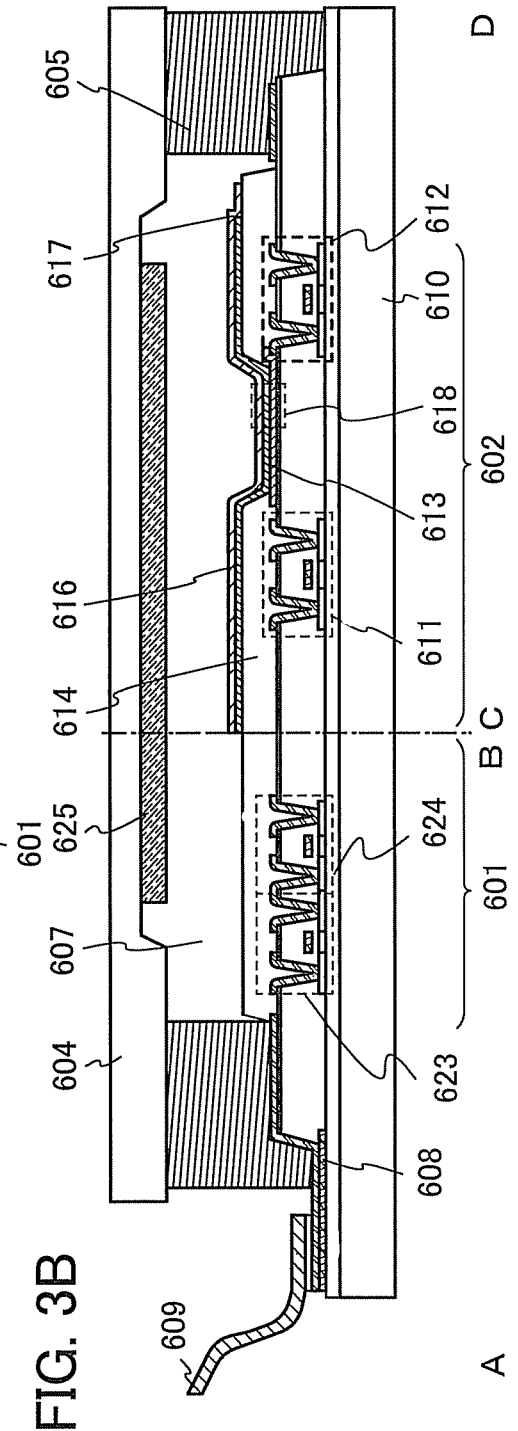
FIG. 3A
FIG. 3B

DIBENZO[C,G]CARBAZOLE COMPOUND, LIGHT-EMITTING ELEMENT, LIGHT-EMITTING DEVICE, DISPLAY DEVICE, LIGHTING DEVICE AND ELECTRONIC DEVICE

TECHNICAL FIELD

The present invention relates to a dibenzo[c,g]carbazole compound. The present invention further relates to a light-emitting element, a light-emitting device, a display device, a lighting device, and an electronic device each using the dibenzo[c,g]carbazole compound.

BACKGROUND ART

A display device using a light-emitting element (organic EL element) in which an organic compound is used as a light-emitting substance has been developed rapidly as a next generation lighting device or display device because it has advantages that such a light-emitting element can be formed to be thin and lightweight, has very high response speed for input signals, and has low power consumption.

In an organic EL element, when a voltage is applied between electrodes with a light-emitting layer interposed therebetween, electrons and holes injected from the electrodes recombine to form an excited state, and when the excited state returns to a ground state, light emission is obtained. Since the wavelength of light emitted from a light-emitting substance is peculiar to the light-emitting substance, use of different types of organic compounds for light-emitting substances makes it possible to provide light-emitting elements which exhibit various wavelengths, i.e., various colors.

Light emitted from a light-emitting substance is peculiar to the substance, as described above. However, important performances as a light-emitting element, such as lifetime and power consumption, are not only dependent on the light-emitting substance but also greatly dependent on layers other than the light-emitting layer, an element structure, properties of a light-emitting substance and a host, compatibility between them, and the like. Thus, it is true that many kinds of light-emitting element materials are necessary for a growth in this field. For the above-described reasons, light-emitting element materials with a variety of molecular structures have been proposed (e.g., Patent Documents 1 to 3).

The substance named 9-[4-(10-phenyl-9-anthryl)phenyl]-9H-carbazole (abbreviation: CzPA) is one of materials which can be used as a transport material or a host material of a light-emitting layer in a light-emitting element. By using CzPA as a host material or an electron-transport material, a light-emitting element which provides blue fluorescence and has very excellent characteristics in terms of emission efficiency, driving voltage, and lifetime can be manufactured.

REFERENCES

[Patent Document 1] United States Published Patent Application No. 2008/0122344
[Patent Document 2] PCT International Publication No. 2010/114264
[Patent Document 3] PCT International Publication No. 2011/010842

DISCLOSURE OF INVENTION

Although many light-emitting element materials have been proposed so far, it is very difficult to develop materials, like CzPA described above, with which it is possible to manufacture a light-emitting element that provides blue fluorescence and has the right combination of important excellent characteristics in terms of emission efficiency, driving voltage, and lifetime.

Therefore, an object of one embodiment of the present invention is to provide a novel compound which can be used for a transport layer or as a host material or a light-emitting material in a light-emitting element and with which a high-performance light-emitting element can be manufactured.

Another object of one embodiment of the present invention is to provide a light-emitting element having high emission efficiency which uses the above novel compound. Another object of one embodiment of the present invention is to provide a light-emitting element having low driving voltage which uses the above novel compound. Another object of one embodiment of the present invention is to provide a light-emitting element having a long lifetime which uses the above novel compound. Another object of one embodiment of the present invention is to provide a light-emitting element having favorable characteristics in terms of emission efficiency, driving voltage, and lifetime which uses the above novel compound.

Another object of one embodiment of the present invention is to provide a light-emitting device having low power consumption which uses a light-emitting element using the above novel compound. Another object of one embodiment of the present invention is to provide a highly reliable light-emitting device which uses a light-emitting element using the above novel compound.

Another object of one embodiment of the present invention is to provide a display device having low power consumption which uses a light-emitting element using the above novel compound. Another object of one embodiment of the present invention is to provide a highly reliable display device which uses a light-emitting element using the above novel compound.

Another object of one embodiment of the present invention is to provide a lighting device having low power consumption which uses a light-emitting element using the above novel compound. Another object of one embodiment of the present invention is to provide a highly reliable lighting device which uses a light-emitting element using the above novel compound.

Another object of one embodiment of the present invention is to provide an electronic device having low power consumption which uses a light-emitting element using the above novel compound. Another object of one embodiment of the present invention is to provide a highly reliable electronic device which uses a light-emitting element using the above novel compound.

Note that in one embodiment of the present invention, it is only necessary that at least one of the above-described objects should be achieved.

The present inventors have synthesized a dibenzo[c,g]carbazole compound in which an aryl group including at least an anthracene skeleton is bonded to nitrogen at the 7-position of a dibenzo[c,g]carbazole derivative and have found that a light-emitting element having very good characteristics can be easily provided by use of the dibenzo[c,g]carbazole compound.

Specifically, a structure of the present invention is a light-emitting element including a dibenzo[c,g]carbazole compound in which an aryl group is bonded to the 7-position of a dibenzo[c,g]carbazole skeleton and the aryl group has 14 to 30 carbon atoms and includes at least an anthracene skeleton. Note that when the number of carbon atoms of the aryl group is 14 to 30, the dibenzo[c,g]carbazole compound is a low molecular compound with a relatively low molecular weight and accordingly has a structure suitable for vacuum evaporation (capable of being vacuum-evaporated at relatively low temperature). In general, a lower molecular weight tends to diminish heat resistance after film formation. However, even with a low molecular weight, the dibenzo[c,g]carbazole compound has an advantage in that sufficient heat resistance can be ensured because of the effect of the rigid dibenzo[c,g] carbazole skeleton.

Further, the present inventors have found that a light-emitting element using a dibenzo[c,g]carbazole compound in which an anthracene skeleton is bonded to a dibenzo[c,g] carbazole skeleton through a phenylene group especially has the advantage in lifetime. The inventors have also found that the dibenzo[c,g]carbazole compound has an excellent carrier-transport property and a light-emitting element using this compound can be driven at very low voltage.

Accordingly, another structure of the present invention is a light-emitting element including a dibenzo[c,g]carbazole compound in which an anthracene skeleton is bonded to the 7-position of a dibenzo[c,g]carbazole skeleton through a phenylene group.

The present inventors have also found that a dibenzo[c,g] carbazole compound in which the 7-position of a dibenzo[c, g]carbazole skeleton is bonded to the 9-position of an anthracene skeleton through a phenylene group especially has a wide band gap and is effective.

Accordingly, another structure of the present invention is a light-emitting element including a dibenzo[c,g]carbazole compound in which the 7-position of a dibenzo[c,g]carbazole skeleton is bonded to the 9-position of an anthracene skeleton through a phenylene group.

Furthermore, the present inventors have found the favorable stability and reliability of the element characteristics of a light-emitting element using a dibenzo[c,g]carbazole compound in which the number of carbon atoms of an anthryl phenyl group bonded to a dibenzo[c,g]carbazole skeleton is 20 to 30. The present inventors have also found the excellent driving voltage of the light-emitting element. This is probably because the dibenzo[c,g]carbazole compound can be vacuum-evaporated at relatively low temperature as described above and accordingly is unlikely to deteriorate due to pyrolysis or the like at evaporation and because the dibenzo [c,g]carbazole compound has electrochemical stability and a high carrier-transport property owing to its molecular structure in which an anthracene skeleton is bonded to the 7-position of a dibenzo[c,g]carbazole skeleton through a phenylene group.

Accordingly, another structure of the present invention is a light-emitting element including a dibenzo[c,g]carbazole compound in which a substituted or unsubstituted anthryl phenyl group is bonded to the 7-position of a dibenzo[c,g] carbazole skeleton and the number of carbon atoms of the substituted or unsubstituted anthryl phenyl group is 20 to 30.

Further, the present inventors have also found the favorable stability and reliability of the element characteristics of a light-emitting element using a dibenzo[c,g]carbazole compound in which the number of carbon atoms of (9-anthryl) phenyl group bonded to a dibenzo[c,g]carbazole skeleton is 20 to 30. The present inventors have also found the excellent driving voltage of the light-emitting element. The present inventors have also found that the compound especially has a wide band gap and is effective. Thus, the dibenzo[c,g]carbazole compound has a wide band gap which is a feature due to the effect of the skeleton of the 9-anthryl group, in addition to the high suitability for evaporation, electrochemical stability, and carrier-transport property described above. Hence, this compound is effective in a structure of a light-emitting element in which the dibenzo[c,g]carbazole compound is used as a host material of a light-emitting layer and a light-emitting material is added as a guest material to the light-emitting layer.

Accordingly, another structure of the present invention is a light-emitting element including a dibenzo[c,g]carbazole compound in which a substituted or unsubstituted (9-anthryl) phenyl group is bonded to the 7-position of a dibenzo[c,g] carbazole skeleton and the number of carbon atoms of the substituted or unsubstituted (9-anthryl)phenyl group is 20 to 30.

Another structure of the present invention is a dibenzo[c, g]carbazole compound represented by the following general formula (G1), with which a light-emitting element having favorable characteristics as described above can be easily achieved.

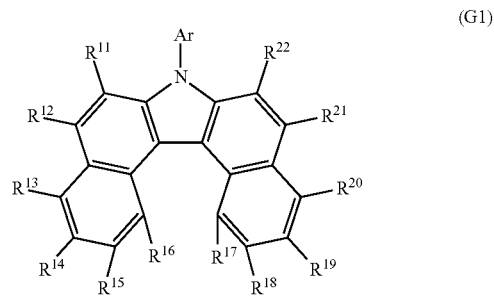

(G1)

In the general formula (G1), Ar represents an aryl group which has 14 to 30 carbon atoms and includes at least an anthracene skeleton. Further, $R^{11}$ to $R^{22}$ each independently represent any of hydrogen, an alkyl group having 1 to 4 carbon atoms, and an aryl group having 6 to 12 carbon atoms.

In the above dibenzo[c,g]carbazole, compound represented by the general formula (G1), when the anthracene skeleton is bonded to a dibenzo[c,g]carbazole skeleton through a phenylene group, the dibenzo[c,g]carbazole compound can be synthesized with higher purity and has an excellent carrier-transport property.

Accordingly, another structure of the present invention is a dibenzo[c,g]carbazole compound represented by the following general formula (G2).

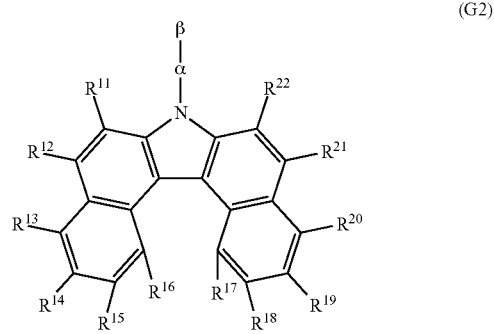

(G2)

In the general formula (G2), $R^{11}$ to $R^{22}$ each independently represent any of hydrogen, an alkyl group having 1 to 4 carbon atoms, and an aryl group having 6 to 12 carbon atoms, α represents a substituted or unsubstituted phenylene group, and β represents a substituted or unsubstituted anthryl group.

In the dibenzo[c,g]carbazole compound represented by the general formula (G2), when the 7-position of a dibenzo[c,g]carbazole skeleton is bonded to the 9-position of an anthracene skeleton, the dibenzo[c,g]carbazole compound especially has a wide band gap and is effective.

Accordingly, another structure of the present invention is a dibenzo[c,g]carbazole compound represented by the following general formula (G3).

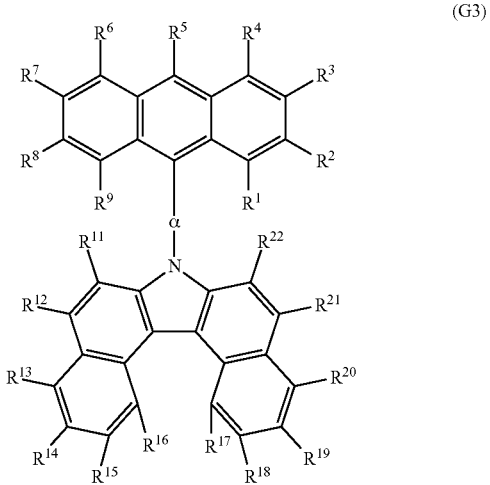

(G3)

In the general formula (G3), $R^5$ represents any of hydrogen, an alkyl group having 1 to 4 carbon atoms, and an aryl group having 6 to 10 carbon atoms, $R^1$, $R^2$, $R^3$, $R^4$, $R^6$, $R^7$, $R^8$, and $R^9$ each independently represent hydrogen or an alkyl group having 1 to 4 carbon atoms, $R^{11}$ to $R^{22}$ each independently represent any of hydrogen, an alkyl group having 1 to 4 carbon atoms, and an aryl group having 6 to 12 carbon atoms, and α represents a substituted or unsubstituted phenylene group.

Furthermore, a light-emitting element using a dibenzo[c,g]carbazole compound in which the number of carbon atoms of an anthryl phenyl group bonded to a dibenzo[c,g]carbazole skeleton is 20 to 30 has element characteristics with favorable stability and reliability, which is a structure preferred in terms of evaporation in the formation of a light-emitting element.

Accordingly, another structure of the present invention is a dibenzo[c,g]carbazole compound represented by the following general formula (G4).

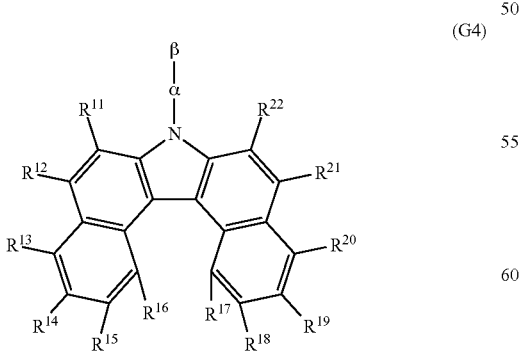

(G4)

In the general formula (G4), $R^{11}$ to $R^{22}$ each independently represent any of hydrogen, an alkyl group having 1 to 4 carbon atoms, and an aryl group having 6 to 12 carbon atoms, α represents a substituted or unsubstituted phenylene group, and β represents a substituted or unsubstituted anthryl group. Note that the total number of carbon atoms of α and β is 20 to 30.

Accordingly, another structure of the present invention is a dibenzo[c,g]carbazole compound represented by the following general formula (G5).

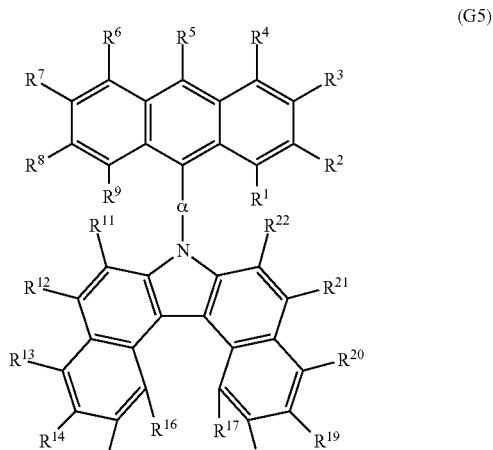

(G5)

In the general formula (G5), $R^5$ represents any of hydrogen, an alkyl group having 1 to 4 carbon atoms, and an aryl group having 6 to 10 carbon atoms, $R^1$, $R^2$, $R^3$, $R^4$, $R^6$, $R^7$, $R^8$, and $R^9$ each independently represent hydrogen or an alkyl group having 1 to 4 carbon atoms, $R^{11}$ to $R^{22}$ each independently represent any of hydrogen, an alkyl group having 1 to 4 carbon atoms, and an aryl group having 6 to 12 carbon atoms, and α represents a substituted or unsubstituted phenylene group. Note that the total number of carbon atoms of $R^1$ to $R^9$ and α is greater than or equal to 6 and less than or equal to 16.

Further, $R^1$, $R^2$, $R^3$, $R^4$, $R^6$, $R^7$, $R^8$, and $R^9$ are each preferably hydrogen in that synthesis becomes easy and the advantage in material cost can be obtained.

Accordingly, another structure of the present invention is a dibenzo[c,g]carbazole compound represented by the following general formula (G6).

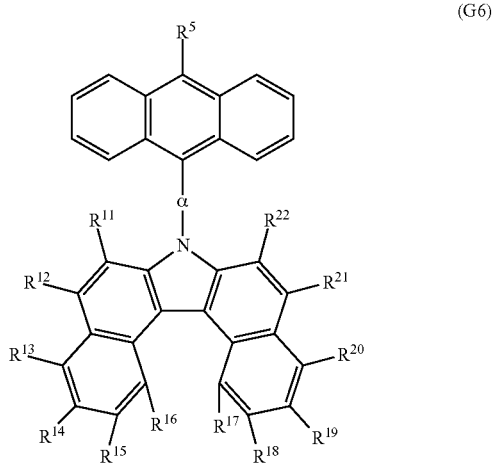

(G6)

In the general formula (G6), α represents a substituted or unsubstituted phenylene group, $R^5$ represents any of hydrogen, an alkyl group having 1 to 4 carbon atoms, and an aryl group having 6 to 10 carbon atoms, and $R^{11}$ to $R^{22}$ each independently represent any of hydrogen, an alkyl group having 1 to 4 carbon atoms, and an aryl group having 6 to 12 carbon atoms. Note that the total number of carbon atoms of $R^5$ and α is greater than or equal to 6 and less than or equal to 16.

As in the above, $R^{11}$ to $R^{22}$ are each preferably hydrogen, in which case a greater advantage can be drawn.

Accordingly, another structure of the present invention is a dibenzo[c,g]carbazole compound represented by the following general formula (G7).

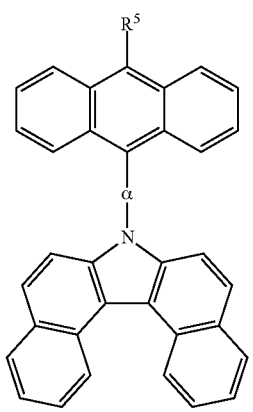

(G7)

In the general formula (G7), α represents a substituted or unsubstituted phenylene group, and $R^5$ represents any of hydrogen, an alkyl group having 1 to 4 carbon atoms, and an aryl group having 6 to 10 carbon atoms. Note that the total number of carbon atoms of $R^5$ and α is greater than or equal to 6 and less than or equal to 16.

Another structure of the present invention is a dibenzo[c,g]carbazole compound represented by the following structural formula (100).

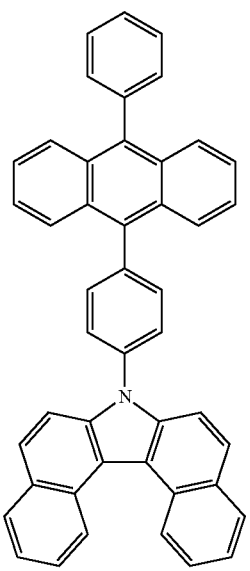

(100)

Another structure of the present invention is a dibenzo[c,g]carbazole compound represented by the following structural formula (127).

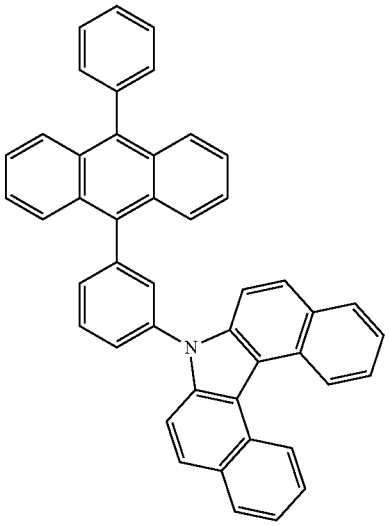

(127)

A dibenzo[c,g]carbazole compound having any of the above structures is a light-emitting element material having a wide energy gap, and can be suitably used for a transport layer, a host material, or a light-emitting substance in a blue fluorescent element or the like. In addition, the dibenzo[c,g]carbazole compound has a favorable carrier-transport property, and a light-emitting element having low driving voltage can be provided by using the compound. Further, the dibenzo[c,g]carbazole compound is stable to oxidation and reduction, and a light-emitting element manufactured using the compound can be a light-emitting element having a long lifetime which less deteriorates. Furthermore, when the dibenzo[c,g]carbazole compound has such characteristics in combination, a high-performance light-emitting element which is excellent in emission efficiency, driving voltage, and lifetime can be manufactured.

With the use of a light-emitting element using a dibenzo[c,g]carbazole compound, a light-emitting device, a display device, a lighting device, or an electronic device each having low power consumption can be obtained. A light-emitting device, a display device, a lighting device, or an electronic device each having high reliability can also be obtained.

BRIEF DESCRIPTION OF DRAWINGS

In the accompanying drawings:
FIGS. 3A and 3B are conceptual diagrams of an active matrix light-emitting device.

BEST MODE FOR CARRYING OUT THE INVENTION

Figure 1A:
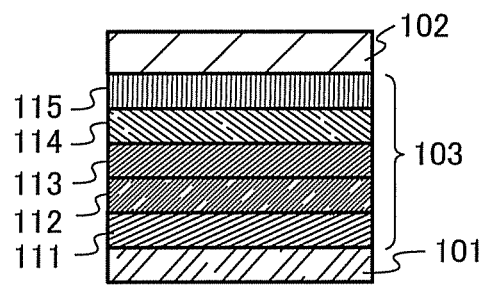
FIGS. 1A and 1B are each a conceptual diagram of a light-emitting element.

Hereinafter, embodiments of the present invention will be described. It is easily understood by those skilled in the art that modes and details disclosed herein can be modified in various ways without departing from the spirit and scope of the present invention. Therefore, the present invention is not construed as being limited to description of the embodiments.

Embodiment 1

A light-emitting element in this embodiment is a light-emitting element including a dibenzo[c,g]carbazole compound in which an aryl group including at least an anthracene skeleton is bonded to the 7-position of a dibenzo[c,g]carbazole skeleton. Since the dibenzo[c,g]carbazole compound has an excellent carrier-transport property, the light-emitting element can be a light-emitting element having low driving voltage. Further, since the dibenzo[c,g]carbazole compound has high resistance to repetition of oxidation and reduction, the light-emitting element can be a light-emitting element having a long lifetime. Furthermore, since the dibenzo[c,g]carbazole compound has a wide band gap, the light-emitting element can be a light-emitting element having high emission efficiency. As described above, a light-emitting element having a structure of this embodiment can easily be a high-performance light-emitting element having the right combination of characteristics.

Note that when the number of carbon atoms of the aryl group is 14 to 30, the dibenzo[c,g]carbazole compound is a low molecular compound with a relatively low molecular weight and accordingly has a structure suitable for vacuum evaporation (capable of being vacuum-evaporated at relatively low temperature). In general, a lower molecular weight tends to diminish heat resistance after film formation. However, even with a low molecular weight, the dibenzo[c,g]carbazole compound has an advantage in that sufficient heat resistance can be ensured because of the effect of the rigid dibenzo[c,g]carbazole skeleton. Note that the anthracene skeleton and the dibenzo[c,g]carbazole skeleton described above may be bonded with an arylene group, such as a phenylene group or a naphthylene group, interposed therebetween.

Further, a light-emitting element using a dibenzo[c,g]carbazole compound in which an anthracene skeleton is bonded to the 7-position of a dibenzo[c,g]carbazole skeleton through a phenylene group especially has the advantage in lifetime. The dibenzo[c,g]carbazole compound has an excellent carrier-transport property and a light-emitting element using this compound can be driven at very low voltage.

The above light-emitting element can be rephrased as a light-emitting element including a dibenzo[c,g]carbazole compound in which an anthryl phenyl group is bonded to a dibenzo[c,g]carbazole skeleton. The dibenzo[c,g]carbazole compound can be easily synthesized with high purity, so that deterioration due to impurities can be suppressed. Note that the number of carbon atoms of the anthryl phenyl group bonded to the dibenzo[c,g]carbazole skeleton is preferably 20 to 30 in terms of the stability and reliability of element characteristics. In this case, the dibenzo[c,g]carbazole compound can be vacuum-evaporated at relatively low temperature as described above and accordingly is unlikely to deteriorate due to pyrolysis or the like at evaporation. In addition, the light-emitting element is excellent in not only reliability but also driving voltage. This is also because of electrochemical stability and high carrier-transport property owing to the molecular structure of the dibenzo[c,g]carbazole compound in which an anthracene skeleton is bonded to the 7-position of a dibenzo[c,g]carbazole skeleton through a phenylene group.

Further, a light-emitting element using a dibenzo[c,g]carbazole compound in which the 9-position of an anthracene skeleton is bonded to the 7-position of a dibenzo[c,g]carbazole skeleton is particularly suitable as a light-emitting element which exhibits light emission with large energy such as blue fluorescence. Note that the anthracene skeleton and the dibenzo[c,g]carbazole skeleton described above may be bonded with an arylene group, such as a phenylene group or a naphthylene group, interposed therebetween.

For the above reason, a light-emitting element including a dibenzo[c,g]carbazole compound in which the 9-position of an anthracene skeleton is bonded to a dibenzo[c,g]carbazole skeleton through a phenylene group is preferred. In other words, a light-emitting element including a dibenzo[c,g]carbazole compound in which a (9-anthryl)phenyl group is bonded to the 7-position of a dibenzo[c,g]carbazole skeleton is preferred. Note that the number of carbon atoms of the (9-anthryl)phenyl group bonded to the dibenzo[c,g]carbazole skeleton is preferably 20 to 30 in terms of the stability and reliability of element characteristics. Thus, the dibenzo[c,g] carbazole compound has a wide band gap which is a feature due to the effect of the skeleton of the 9-anthryl group, in addition to the high suitability for evaporation, electrochemical stability, and carrier-transport property described above. Hence, this compound is effective in a structure of a light-emitting element in which the dibenzo[c,g]carbazole compound is used as a host material of a light-emitting layer and a light-emitting material is added as a guest material to the light-emitting layer.

Embodiment 2

In this embodiment, a dibenzo[c,g]carbazole compound used to achieve a light-emitting element described in Embodiment 1 is described.

A dibenzo[c,g]carbazole compound of this embodiment is a dibenzo[c,g]carbazole compound in which an aryl group including at least an anthracene skeleton is bonded to the 7-position of a dibenzo[c,g]carbazole skeleton. The dibenzo [c,g]carbazole compound has an excellent carrier-transport property. In addition, the dibenzo[c,g]carbazole compound has favorable resistance to repetition of oxidation and reduction. Further, the dibenzo[c,g]carbazole compound has a wide band gap. Accordingly, a high-performance light-emitting element can be easily manufactured by including a dibenzo[c,g]carbazole compound of this embodiment.

Note that the number of carbon atoms of the aryl group bonded to the dibenzo[c,g]carbazole skeleton is preferably 14 to 30 in terms of characteristics such as stability and reliability of the element to be fabricated. When the number of carbon atoms of the aryl group is 14 to 30, the dibenzo[c,g] carbazole compound is a low molecular compound with a relatively low molecular weight and accordingly has a structure suitable for vacuum evaporation (capable of being vacuum-evaporated at relatively low temperature). In general, a lower molecular weight tends to diminish heat resistance after film formation. However, even with a low molecular weight, the dibenzo[c,g]carbazole compound has an advantage in that sufficient heat resistance can be ensured because of the effect of the rigid dibenzo[c,g]carbazole skeleton. Note that in this specification, when the number of carbon atoms is defined, this number means the total number of carbon atoms including those of a substituent of the group, compound, or the like, of which the definition is given.

The above dibenzo[c,g]carbazole compound can be represented by the following general formula (G1).

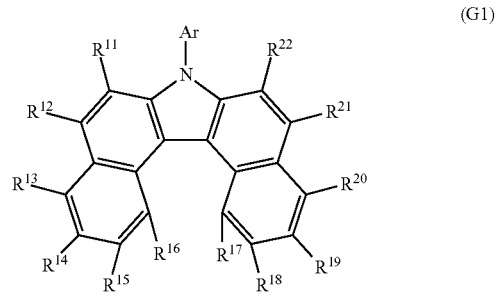

(G1)

In the above general formula (G1), Ar represents a substituted or unsubstituted aryl group which has 14 to 30 carbon atoms and includes at least an anthracene skeleton. When the anthracene skeleton has a substituent, the substituent can be an alkyl group having 1 to 4 carbon atoms. Other than such a substituent, an aryl group having 6 to 12 carbon atoms can also be selected as the substituent at the 10-position of the anthracene skeleton. Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 12 carbon atoms are a phenyl group, a naphthyl group, a biphenyl group, and the like.

Further, $R^{11}$ to $R^{22}$ each independently represent any of hydrogen, an alkyl group having 1 to 4 carbon atoms, and an aryl group having 6 to 12 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 12 carbon atoms are a phenyl group, a naphthyl group, a biphenyl group, and the like.

In the dibenzo[c,g]carbazole compound of this embodiment, it is preferable that the anthracene skeleton be bonded to the dibenzo[c,g]carbazole skeleton through a phenylene group, in which case the dibenzo[c,g]carbazole compound can have improved stability and can be synthesized with higher purity. Further, since the dibenzo[c,g]carbazole compound has an excellent carrier-transport property, a light-emitting element using this compound can be driven at very low voltage.

The above dibenzo[c,g]carbazole compound can be represented by the following general formula (G2).

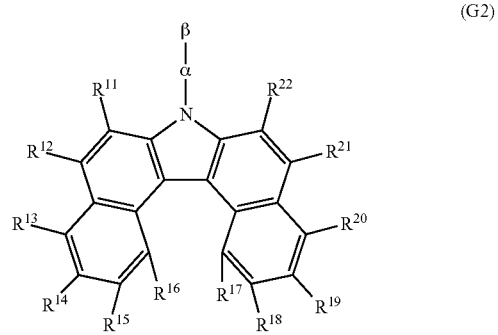

(G2)

In the general formula (G2), $R^{11}$ to $R^{22}$ each independently represent any of hydrogen, an alkyl group having 1 to 4 carbon atoms, and an aryl group having 6 to 12 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 12 carbon atoms are a phenyl group, a naphthyl group, a biphenyl group, and the like.

In the general formula (G2), α represents a substituted or unsubstituted phenylene group, and β represents a substituted or unsubstituted anthryl group. When α has a substituent, an alkyl group having 1 to 4 carbon atoms can be selected as the substituent. Specific examples of the alkyl group having 1 to 4 carbon atoms are a methyl group, an ethyl group, a propyl group, an isopropyl group, a butyl group, an isobutyl group, a tert-butyl group, and the like. When β has a substituent, an alkyl group having 1 to 4 carbon atoms can be selected as the substituent. Other than such a substituent, an aryl group having 6 to 12 carbon atoms can also be selected as the substituent at the 10-position of the anthracene skeleton. Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 12 carbon atoms are a phenyl group, a naphthyl group, a biphenyl group, and the like.

In the above dibenzo[c,g]carbazole compound, when the 7-position of a dibenzo[c,g]carbazole skeleton is bonded to the 9-position of an anthracene skeleton, the dibenzo[c,g]carbazole compound especially has a wide band gap and is effective. This is particularly effective in a structure of a light-emitting element in which the dibenzo[c,g]carbazole compound is used as a host material of a light-emitting layer and a light-emitting material is added as a guest material to the light-emitting layer. The above dibenzo[c,g]carbazole compound can be represented by the following general formula (G3).

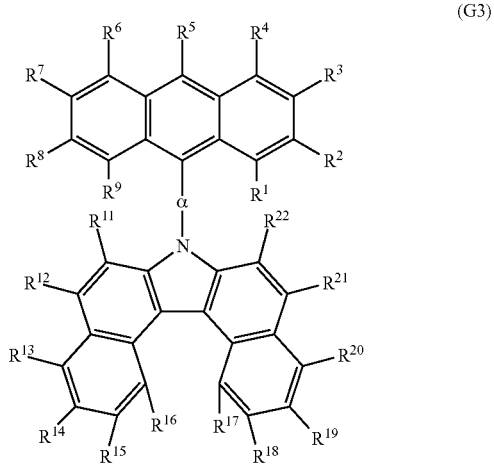

(G3)

In the general formula (G3), $R^5$ represents any of hydrogen, an alkyl group having 1 to 4 carbon atoms, and an aryl group having 6 to 10 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 10 carbon atoms are a phenyl group, a naphthyl group, and the like. Further, $R^1$, $R^2$, $R^3$, $R^4$, $R^6$, $R^7$, $R^8$, and $R^9$ each independently represent hydrogen or an alkyl group having 1 to 4 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Further, $R^{11}$ to $R^{22}$ each independently represent any of hydrogen, an alkyl group having 1 to 4 carbon atoms, and an aryl group having 6 to 12 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 12 carbon atoms are a phenyl group, a naphthyl group, a biphenyl group, and the like. In addition, α represents a substituted or unsubstituted phenylene group. When α has a substituent, an alkyl group having 1 to 4 carbon atoms can be selected as the substituent. Specific examples of the alkyl group having 1 to 4 carbon atoms are a methyl group, an ethyl group, a propyl group, an isopropyl group, a butyl group, an isobutyl group, a tert-butyl group, and the like.

Note that the dibenzo[c,g]carbazole compound represented by the general formula (G2) can be rephrased as a dibenzo[c,g]carbazole compound in which a phenyl anthryl group is bonded to a dibenzo[c,g]carbazole skeleton, and the dibenzo[c,g]carbazole compound represented by the general formula (G3) can be rephrased as a dibenzo[c,g]carbazole compound in which a (9-phenyl)anthryl group is bonded to a dibenzo[c,g]carbazole skeleton. Hence, the number of carbon atoms of the phenyl anthryl group or (9-phenyl)anthryl group bonded to the dibenzo[c,g]carbazole skeleton is preferably 20 to 30 in terms of characteristics such as stability and reliability of the element to be fabricated. This is probably because the dibenzo[c,g]carbazole compound can be vacuum-evaporated at relatively low temperature as described above and accordingly is unlikely to deteriorate due to pyrolysis or the like at evaporation. Note that a dibenzo[c,g]carbazole compound having a (9-phenyl)anthryl group especially has a wide band gap and therefore can be suitably used as a host material of a light-emitting layer in a light-emitting element.

The dibenzo[c,g]carbazole compound has electrochemical stability and a high carrier-transport property owing to its molecular structure in which an anthracene skeleton is bonded to the 7-position of a dibenzo[c,g]carbazole skeleton through a phenylene group.

The above dibenzo[c,g]carbazole compound can be represented by the following general formula (G4) or (G5).

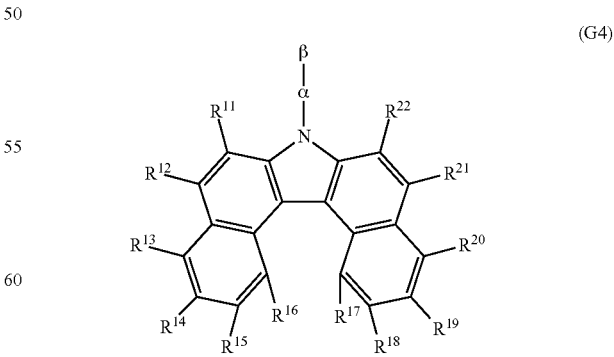

(G4)

In the general formula (G4), $R^{11}$ to $R^{22}$ each independently represent any of hydrogen, an alkyl group having 1 to 4 carbon atoms, and an aryl group having 6 to 12 carbon atoms.

Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 12 carbon atoms are a phenyl group, a naphthyl group, a biphenyl group, and the like. In addition, α represents a substituted or unsubstituted phenylene group. When α has a substituent, an alkyl group having 1 to 4 carbon atoms can be selected as the substituent. Specific examples of the alkyl group having 1 to 4 carbon atoms are a methyl group, an ethyl group, a propyl group, an isopropyl group, a butyl group, an isobutyl group, a tert-butyl group, and the like. Further, β represents a substituted or unsubstituted anthryl group. When β has a substituent, an alkyl group having 1 to 4 carbon atoms can be selected as the substituent. Other than such a substituent, an aryl group having 6 to 12 carbon atoms can also be selected as the substituent at the 10-position of the anthracene skeleton. Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 12 carbon atoms are a phenyl group, a naphthyl group, a biphenyl group, and the like. Note that the total number of carbon atoms of α and β is 20 to 30.

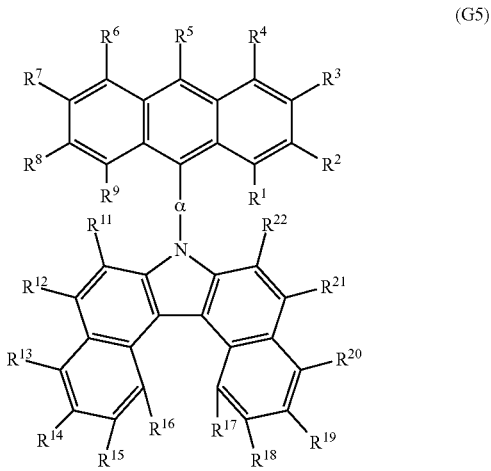

(G5)

In the general formula (G5), $R^5$ represents any of hydrogen, an alkyl group having 1 to 4 carbon atoms, and an aryl group having 6 to 10 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 10 carbon atoms are a phenyl group, a naphthyl group, and the like. Further, $R^1$, $R^2$, $R^3$, $R^4$, $R^6$, $R^7$, $R^8$, and $R^9$ each independently represent hydrogen or an alkyl group having 1 to 4 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Further, $R^{11}$ to $R^{22}$ each independently represent any of hydrogen, an alkyl group having 1 to 4 carbon atoms, and an aryl group having 6 to 12 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Specific examples of the aryl group having 6 to 12 carbon atoms are a phenyl group, a naphthyl group, a biphenyl group, and the like. In addition, α represents a substituted or unsubstituted phenylene group. When α has a substituent, an alkyl group having 1 to 4 carbon atoms can be selected as the substituent. Specific examples of the alkyl group having 1 to 4 carbon atoms are a methyl group, an ethyl group, a propyl group, an isopropyl group, a butyl group, an isobutyl group, a tert-butyl group, and the like. Note that the total number of carbon atoms of $R^1$ to $R^9$ and α is greater than or equal to 6 and less than or equal to 16.

Further, $R^1$, $R^2$, $R^3$, $R^4$, $R^6$, $R^7$, $R^8$, and $R^9$ are each preferably hydrogen in that synthesis becomes easy and the advantage in material cost can be obtained.

Accordingly, another structure of the present invention is a dibenzo[c,g]carbazole compound represented by the following general formula (G6).

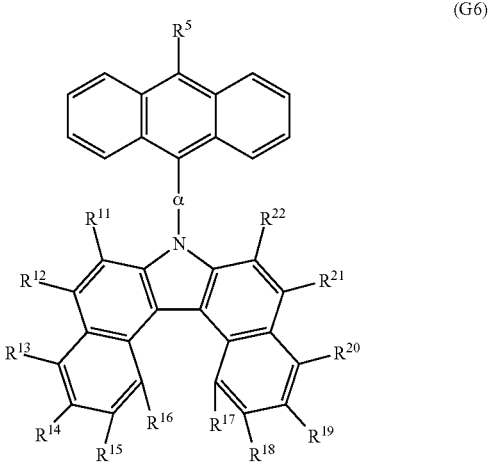

(G6)

In the general formula (G6), α represents a substituted or unsubstituted phenylene group. When α has a substituent, an alkyl group having 1 to 4 carbon atoms can be selected as the substituent. Specific examples of the alkyl group having 1 to 4 carbon atoms are a methyl group, an ethyl group, a propyl group, an isopropyl group, a butyl group, an isobutyl group, a tert-butyl group, and the like. Further, $R^5$ represents any of hydrogen, an alkyl group having 1 to 4 carbon atoms, and an aryl group having 6 to 10 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Further, $R^{11}$ to $R^{22}$ each independently represent any of hydrogen, an alkyl group having 1 to 4 carbon atoms, and an aryl group having 6 to 12 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Note that the total number of carbon atoms of $R^5$ and α is greater than or equal to 6 and less than or equal to 16.

As in the above, $R^{11}$ to $R^{22}$ are each preferably hydrogen, in which case a greater advantage can be drawn.

Accordingly, another structure of the present invention is a dibenzo[c,g]carbazole compound represented by the following general formula (G7).

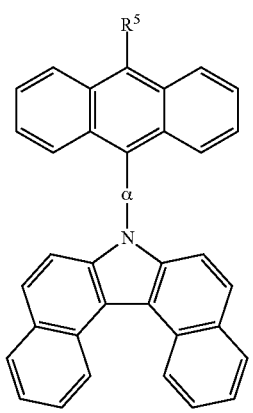
(G7)

In the general formula (G7), α represents a substituted or unsubstituted phenylene group. When α has a substituent, an alkyl group having 1 to 4 carbon atoms can be selected as the substituent. Specific examples of the alkyl group having 1 to 4 carbon atoms are a methyl group, an ethyl group, a propyl group, an isopropyl group, a butyl group, an isobutyl group, a tert-butyl group, and the like. Further, $R^5$ represents any of hydrogen, an alkyl group having 1 to 4 carbon atoms, and an aryl group having 6 to 10 carbon atoms. Specific examples of the alkyl group having 1 to 4 carbon atoms are a methyl group, an ethyl group, a propyl group, an isopropyl group, a butyl group, an isobutyl group, a tert-butyl group, and the like. Note that the total number of carbon atoms of $R^5$ and α is greater than or equal to 6 and less than or equal to 16.

As the aryl group represented by Ar in the above general formula (G1), for example, groups represented by structural formulae (Ar-1) to (Ar-51) below can be used. Note that a group that can be used as Ar is not limited to these.

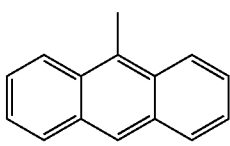
(Ar-1)

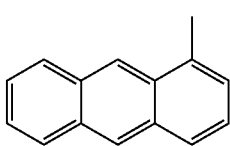
(Ar-2)

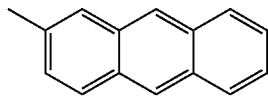
(Ar-3)

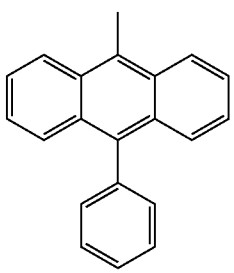
(Ar-4)

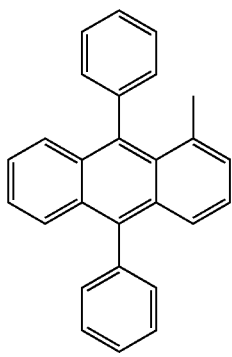
(Ar-5)

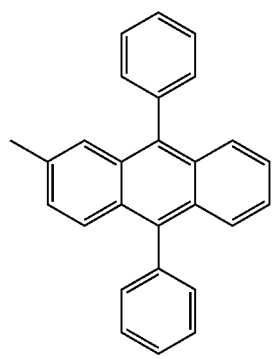
(Ar-6)

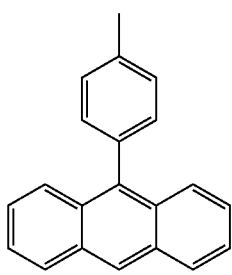
(Ar-7)

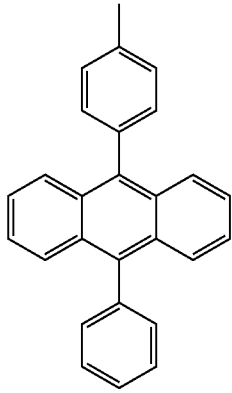
(Ar-8)

(Ar-9)
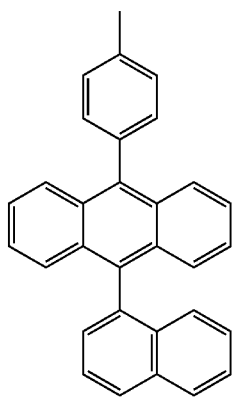
(Ar-10)
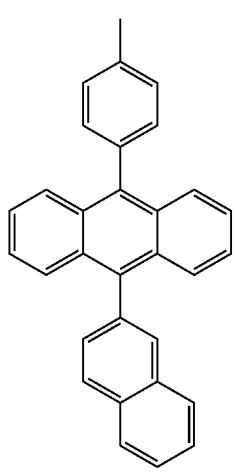
(Ar-11)
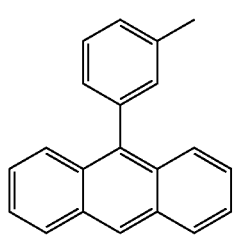
(Ar-12)
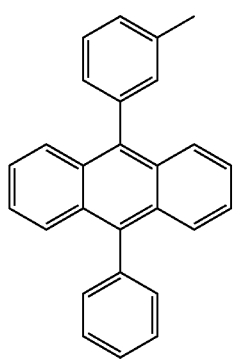
(Ar-13)
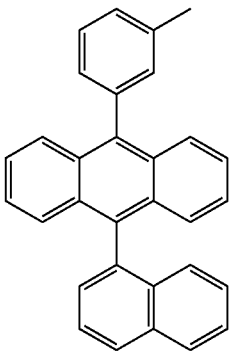
(Ar-14)
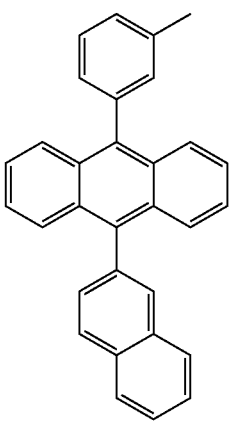
(Ar-15)
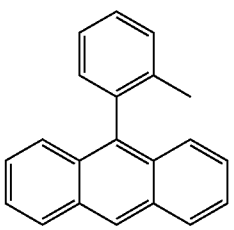
(Ar-16)
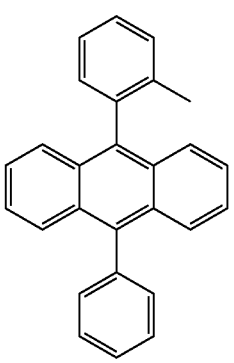

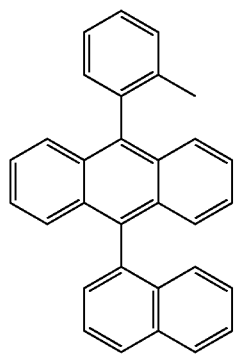 (Ar-17)
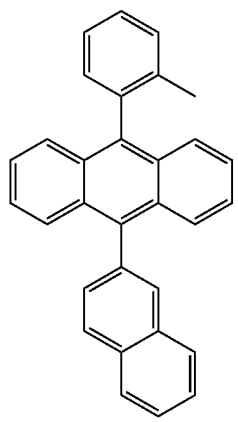 (Ar-18)
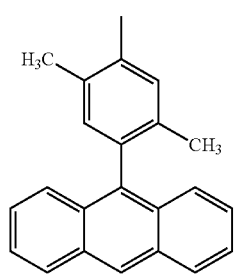 (Ar-19)
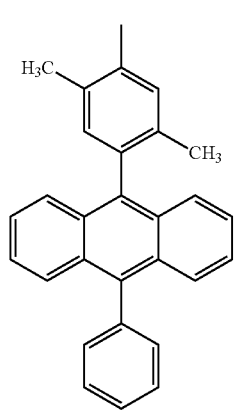 (Ar-20)
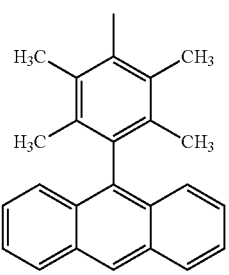 (Ar-21)
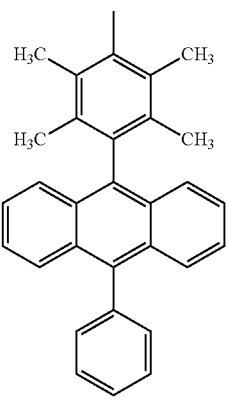 (Ar-22)
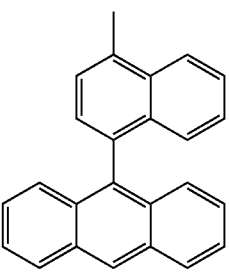 (Ar-23)
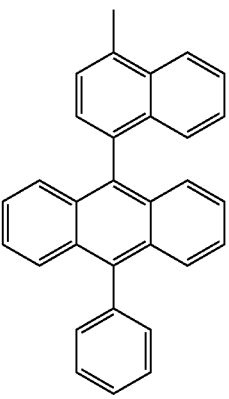 (Ar-24)

(Ar-25)
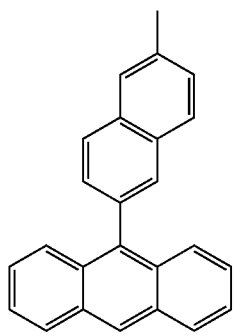
(Ar-26)
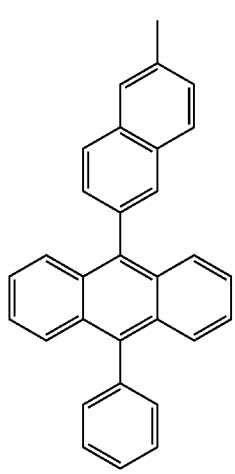
(Ar-27)
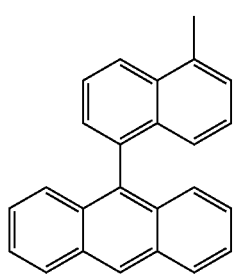
(Ar-28)
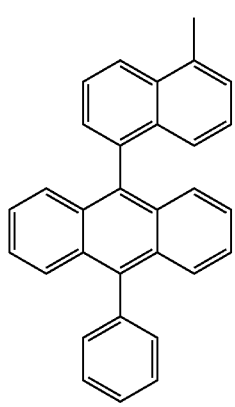
(Ar-29)
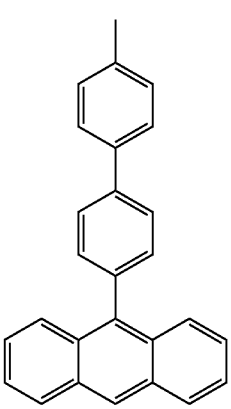
(Ar-30)
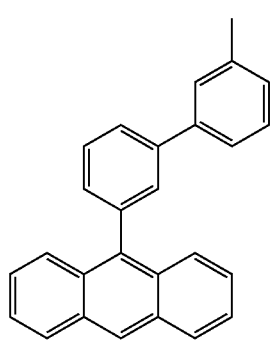
(Ar-31)
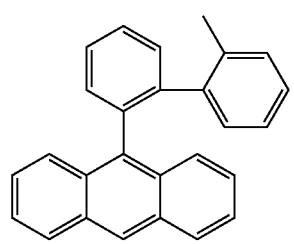
(Ar-32)
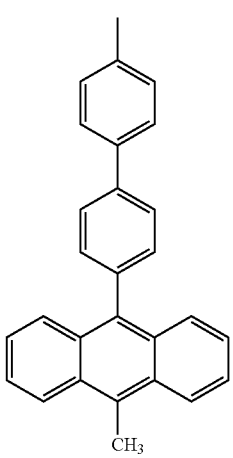

(Ar-33)
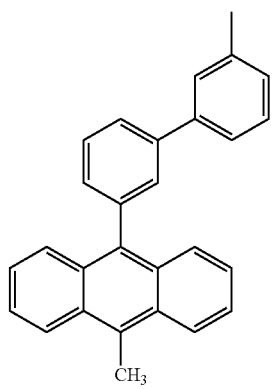
(Ar-34)
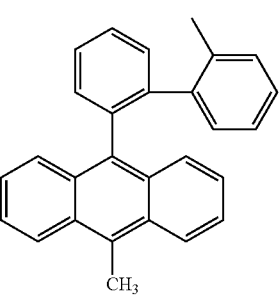
(Ar-35)
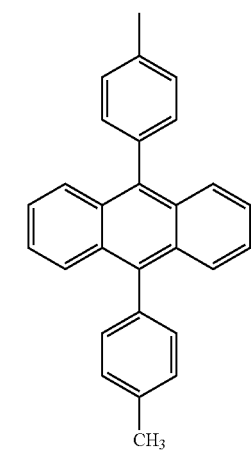
(Ar-36)
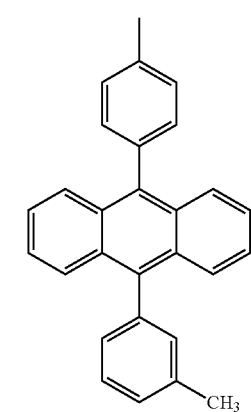
(Ar-37)
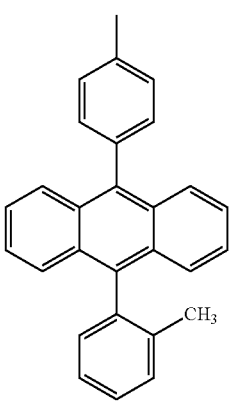
(Ar-38)
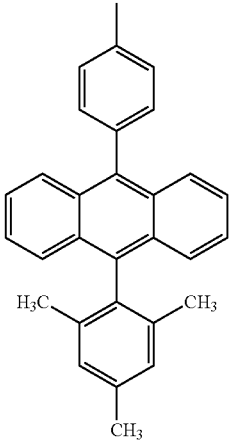
(Ar-39)
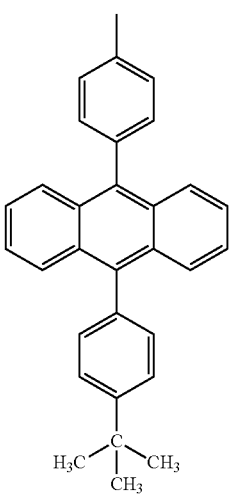
(Ar-40)
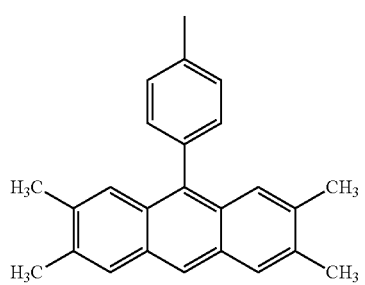

(Ar-41)
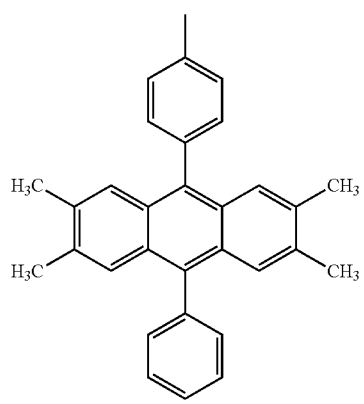
(Ar-42)
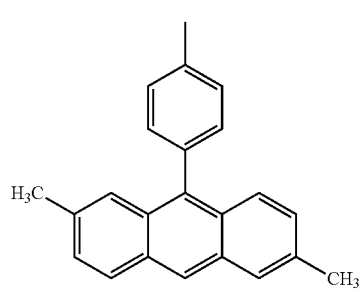
(Ar-43)
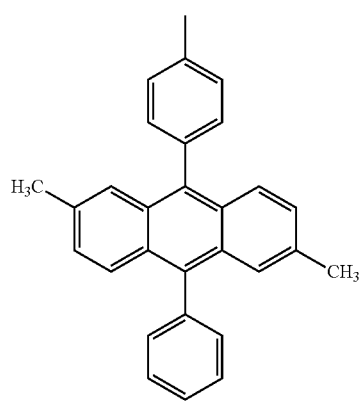
(Ar-44)
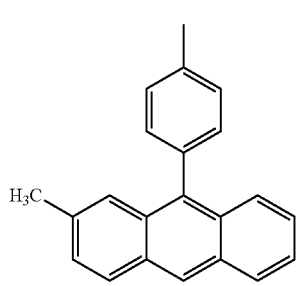
(Ar-45)
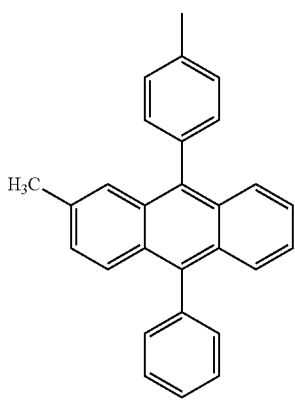
(Ar-46)
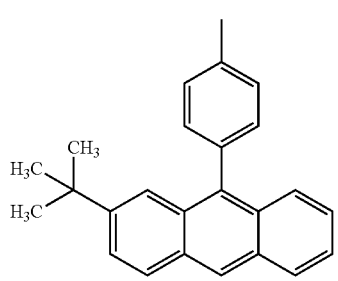
(Ar-47)
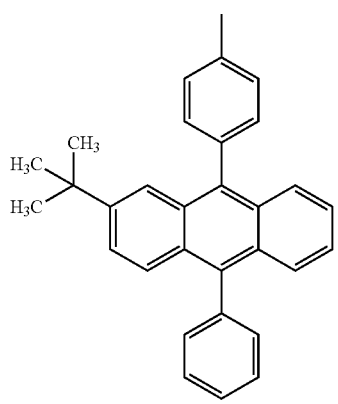
(Ar-48)
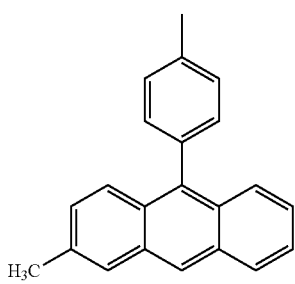

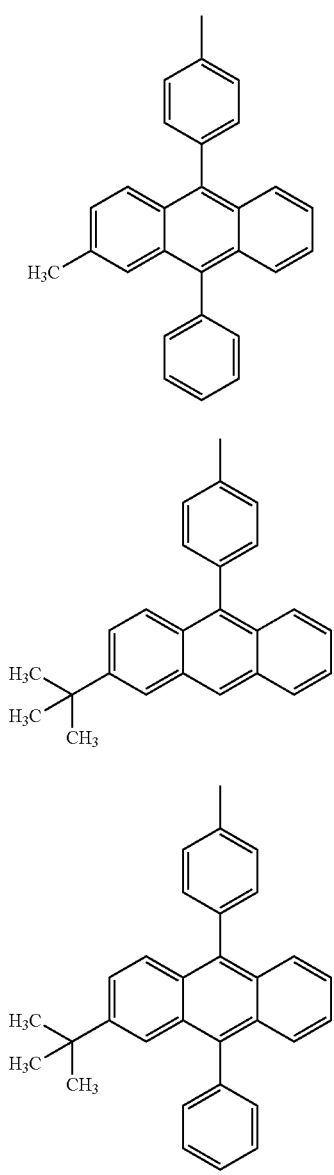
(Ar-49)
(Ar-50)
(Ar-51)
As the aryl group represented by $R^{11}$ to $R^{22}$ in the above general formulae (G1) to (G6), for example, groups represented by structural formulae (Rc-1) to (Rc-17) below can be used. Note that a group that can be used as $R^{11}$ to $R^{22}$ is not limited to these.
(Rc-1)
(Rc-2)
(Rc-3)
(Rc-4)
(Rc-5)
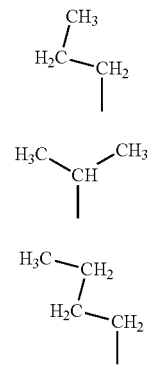
(Rc-6)
(Rc-7)
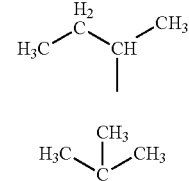
(Rc-8)
(Rc-9)
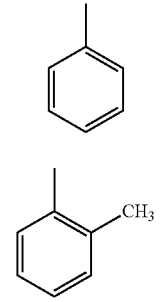
(Rc-10)
(Rc-11)
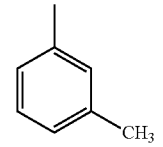
(Rc-12)
(Rc-13)
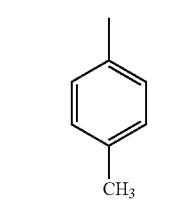
(Rc-14)
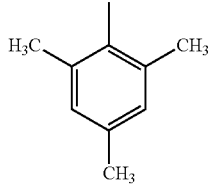

(Rc-15)

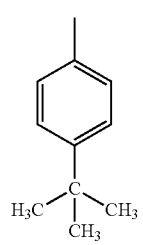

(Rc-16)

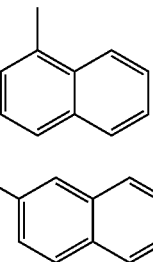

(Rc-17)

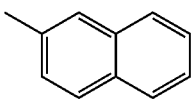

As the aryl group represented by α in the above general formulae (G2) to (G7), for example, groups represented by structural formulae (α-1) to (α-11) below can be used. Note that a group that can be used as α is not limited to these.

(α-1)

(α-2)

(α-3)

(α-4)

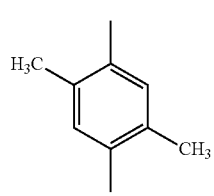

(α-5)

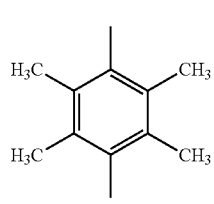

(α-6)

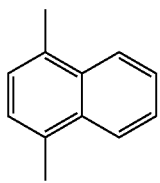

(α-7)

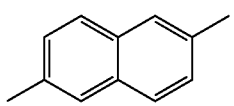

(α-8)

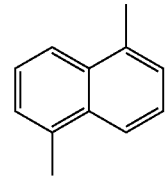

(α-9)

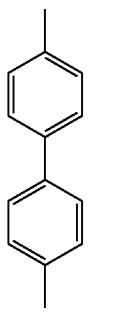

(α-10)

(α-11)

As the aryl group represented by β in the above general formulae (G2) and (G4), for example, groups represented by structural formulae (β-1) to (β-37) below can be used. Note that a group that can be used as β is not limited to these.

(β-1)

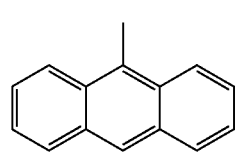

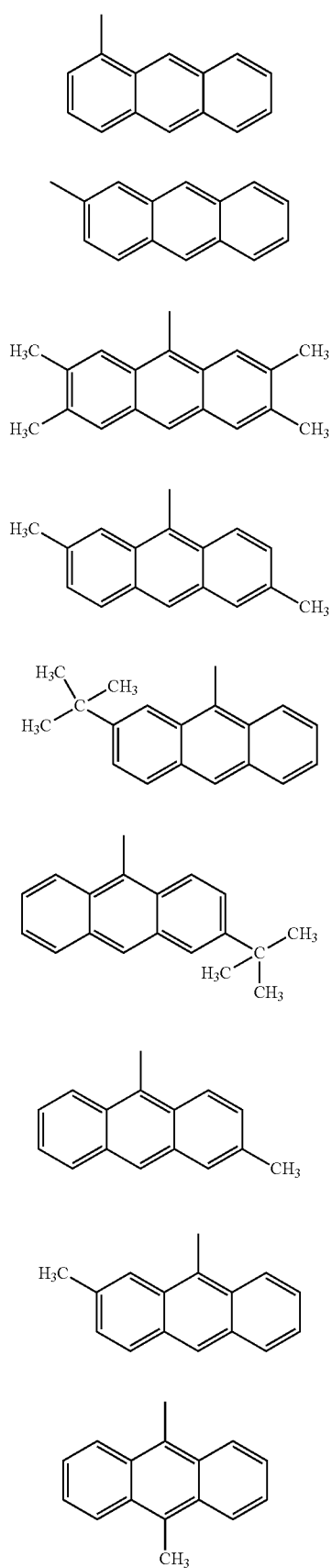
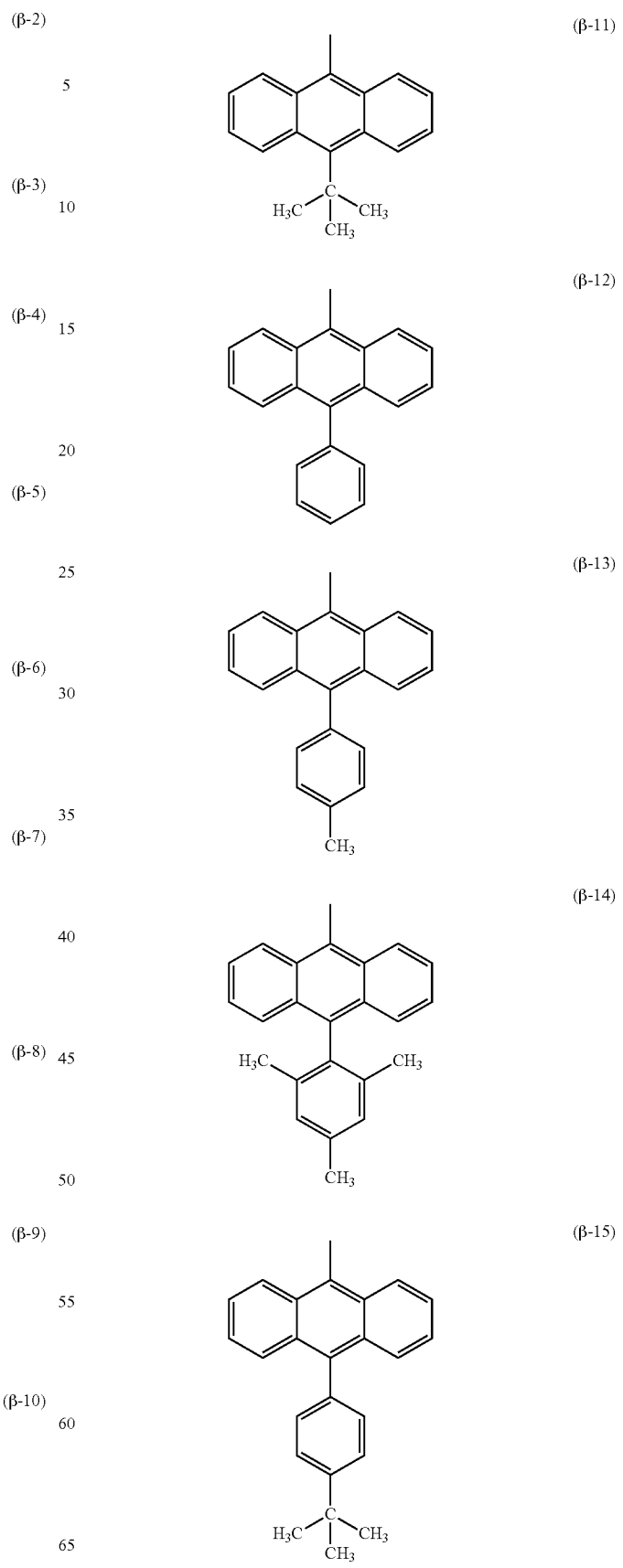

(β-16)
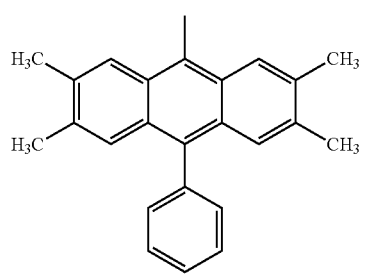
(β-17)
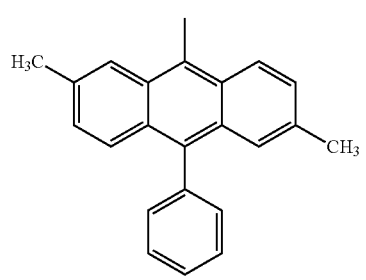
(β-18)
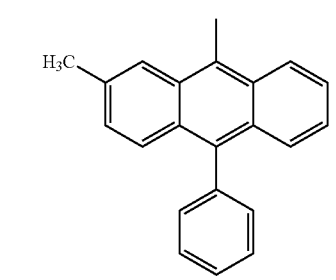
(β-19)
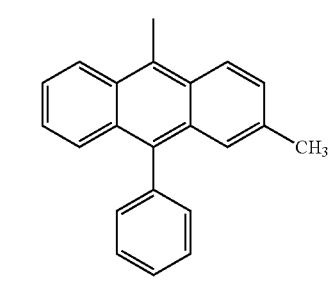
(β-20)
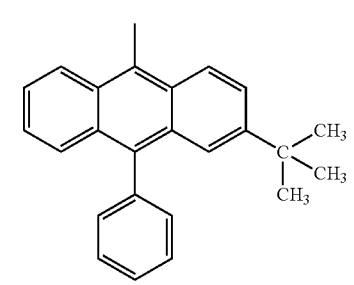
(β-21)
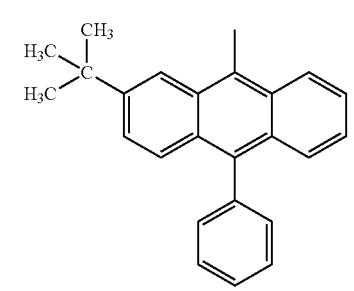
(β-22)
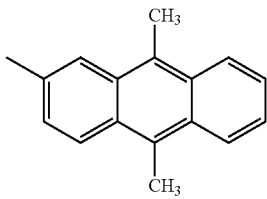
(β-23)
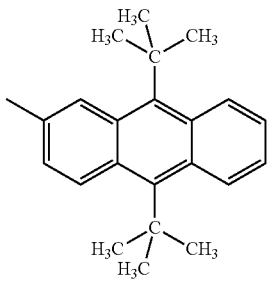
(β-24)
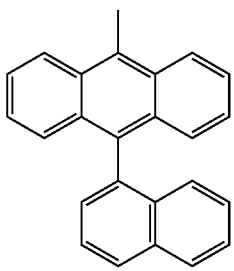
(β-25)
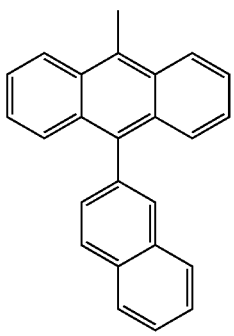
(β-26)
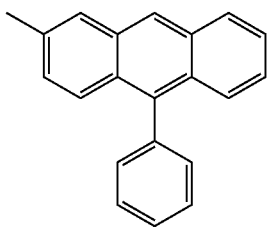
(β-27)
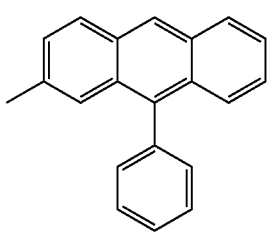

(β-28) 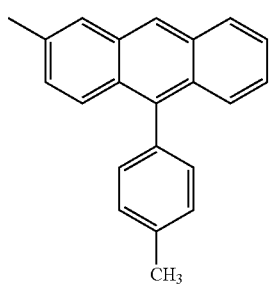
(β-29) 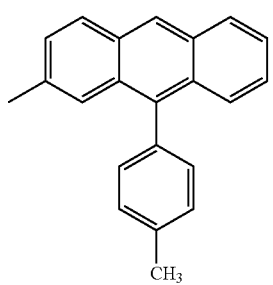
(β-30) 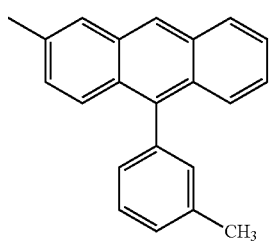
(β-31) 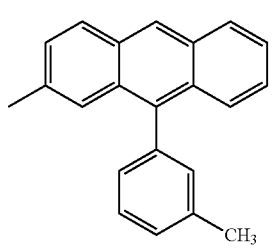
(β-32) 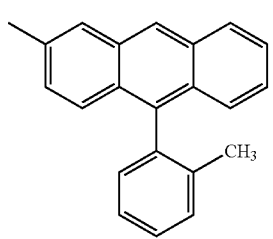
(β-33) 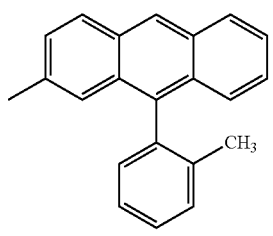
(β-34) 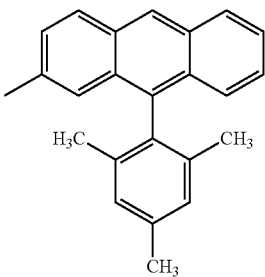
(β-35) 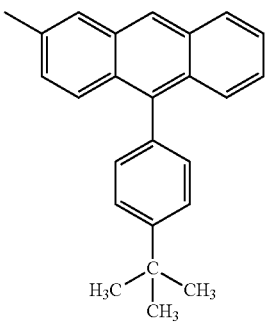
(β-36) 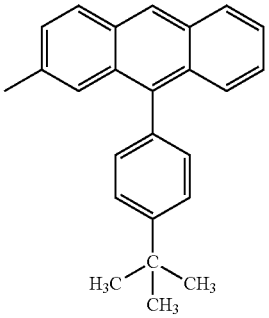
(β-37) 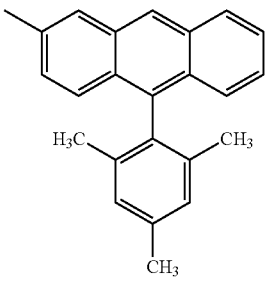
As the aryl group represented by $R^1$, $R^2$, $R^3$, $R^4$, $R^6$, $R^7$, $R^5$, and $R^9$ in the above general formulae (G3) and (G5), for example, groups represented by structural formulae (Ra-1) to (Ra-9) below can be used. Note that a group that can be used as $R^1$, $R^2$, $R^3$, $R^4$, $R^6$, $R^7$, $R^8$, and $R^9$ is not limited to these.
(Ra-1) 
(Ra-2) 

(Ra-3) 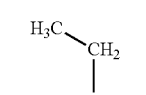
(Ra-4) 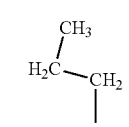
(Ra-5) 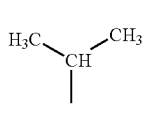
(Ra-6) 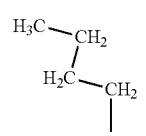
(Ra-7) 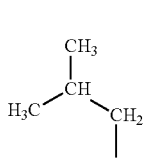
(Ra-8) 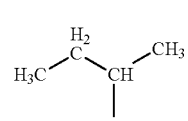
(Ra-9) 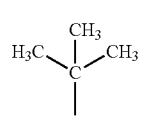
As the aryl group represented by $R^5$ in the above general formulae (G3) and (G5) to (G7), for example, groups represented by structural formulae ($R^5$-1) to ($R^5$-17) below can be used. Note that a group that can be used as $R^5$ is not limited to these.
($R^5$-1) 
($R^5$-2) 
($R^5$-3) 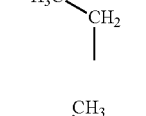
($R^5$-4) 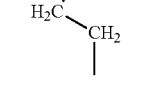
($R^5$-5) 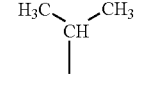
($R^5$-6) 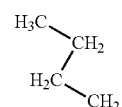
($R^5$-7) 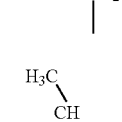
($R^5$-8) 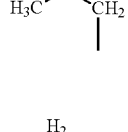
($R^5$-9) 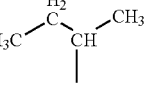
($R^5$-10) 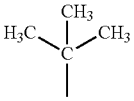
($R^5$-11) 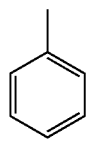
($R^5$-12) 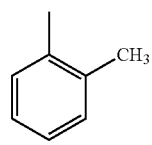
($R^5$-13) 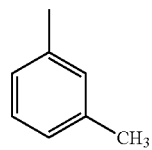
($R^5$-14) 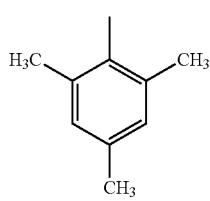

(R⁵-15)
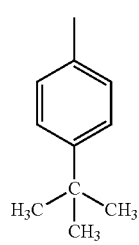
(R⁵-16)
(R⁵-17)
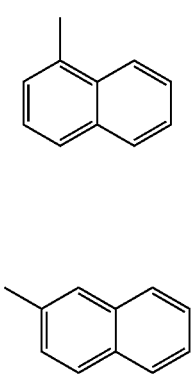
Specific examples of structures of the dibenzo[c,g]carbazole compounds represented by the above general formulae (G1) to (G7) are substances represented by structural formulae (100) to (136) below, and the like. Note that the dibenzo[c,g]carbazole compounds represented by the above general formulae (G1) to (G7) are not limited to the following examples.
(100)
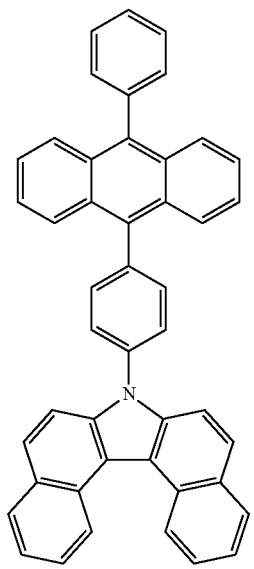
(101)
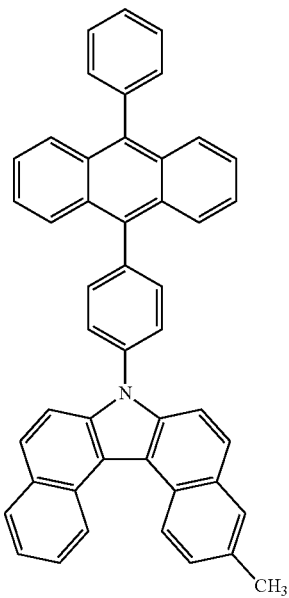
(102)
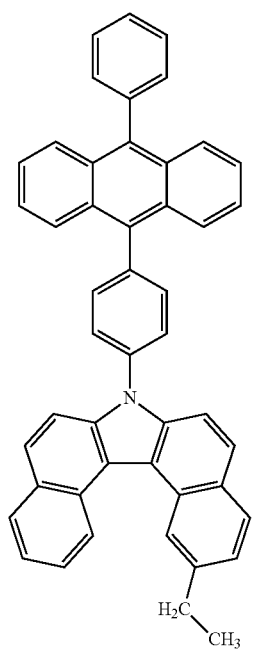

(103)
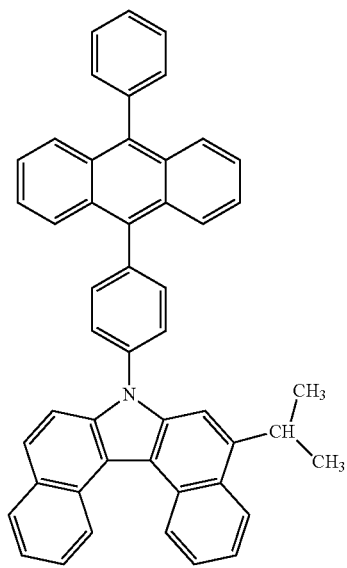
(104)
(105)
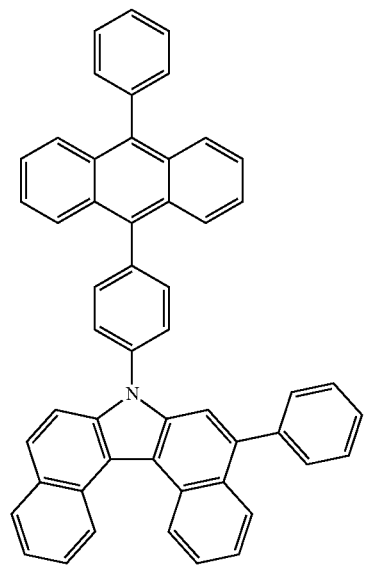
(106)
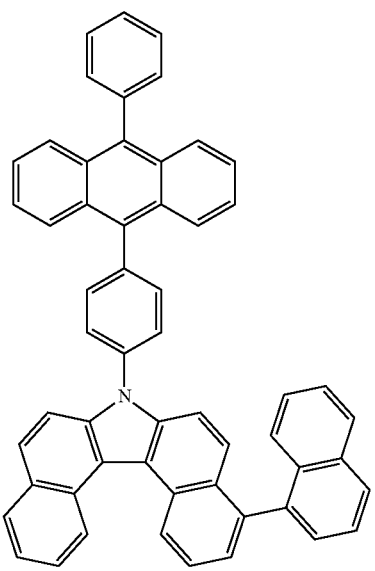

(107)
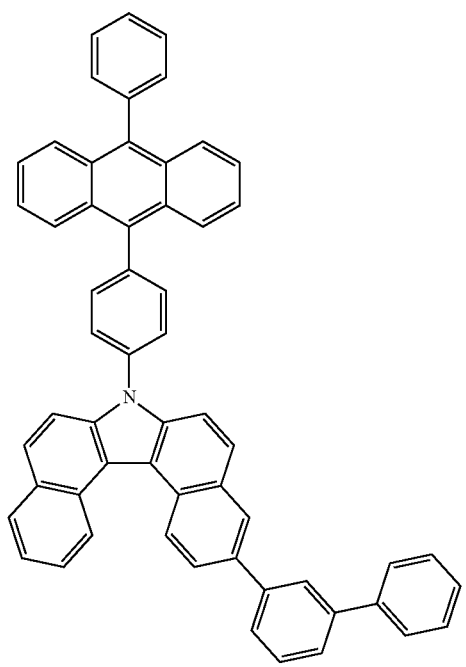
(108)
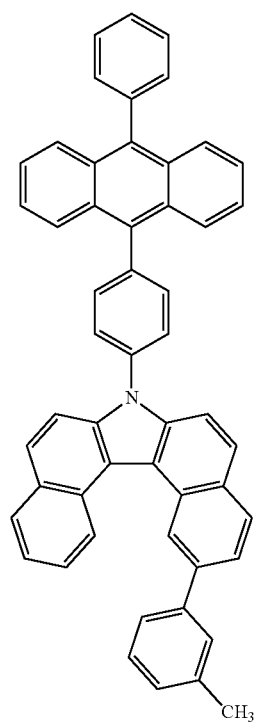
(109)
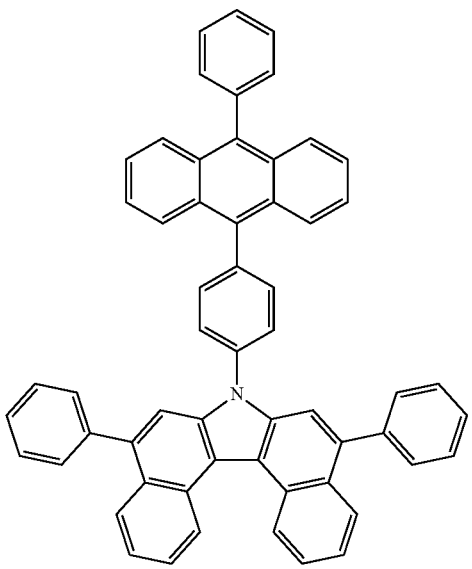
(110)
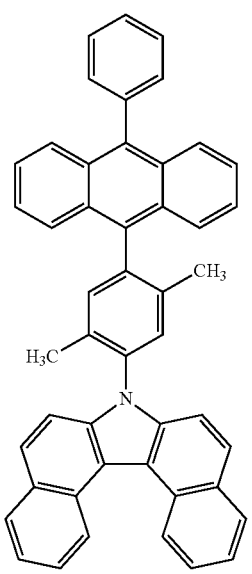

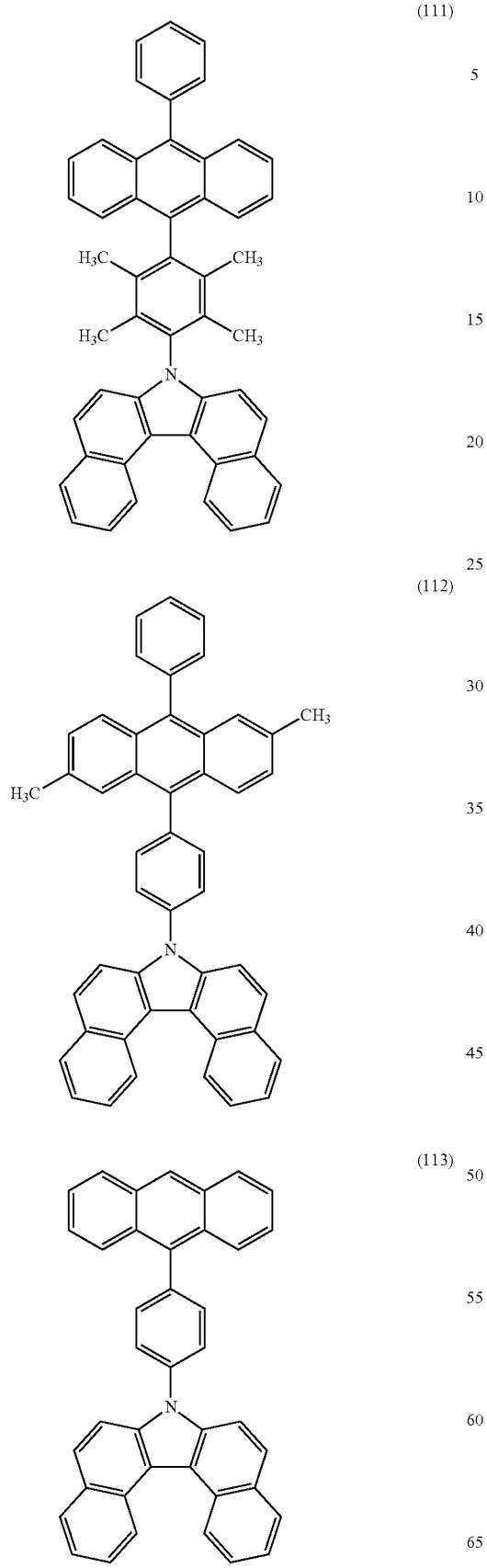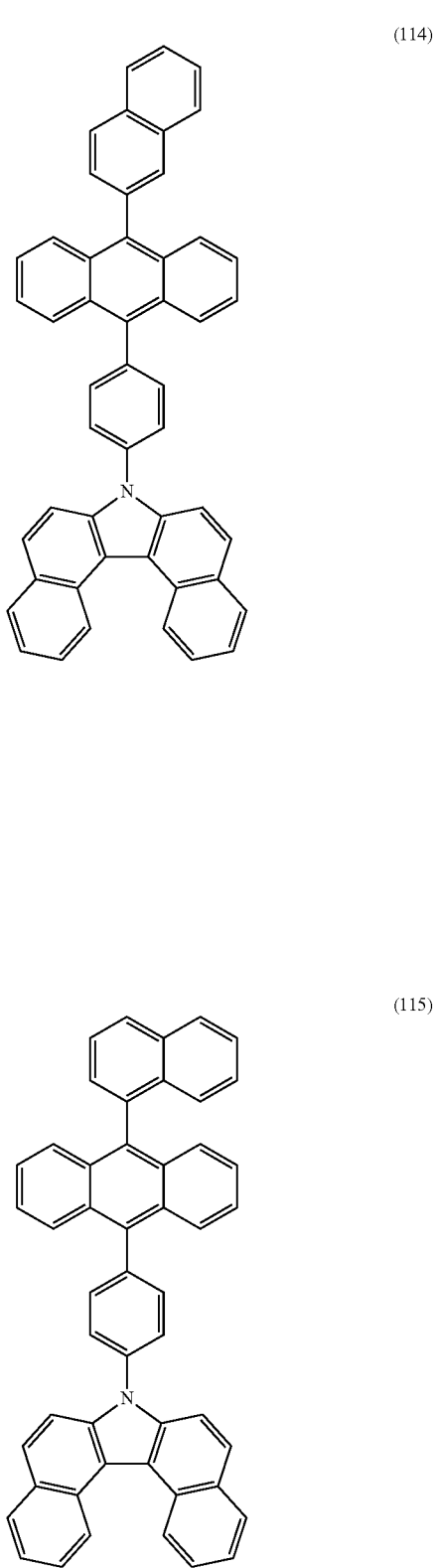

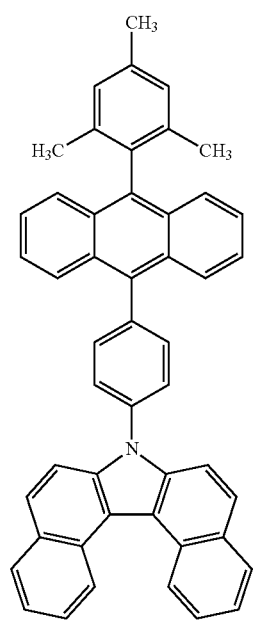 (116)
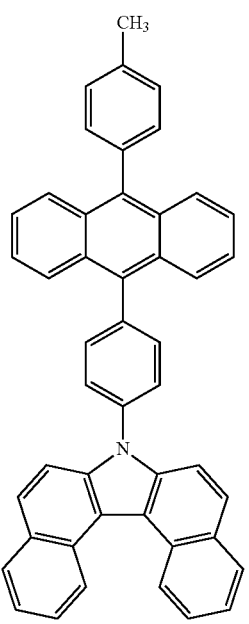 (118)
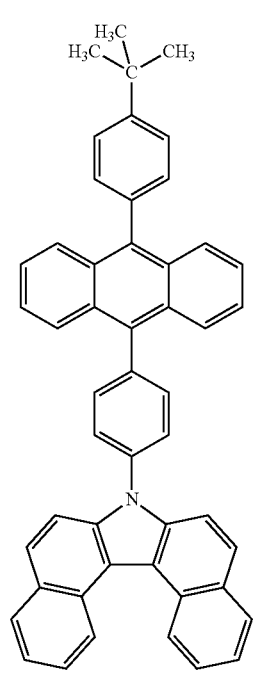 (117)
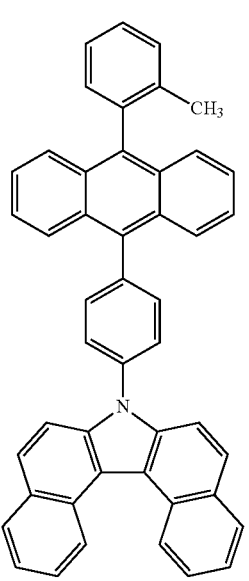 (119)

(120)
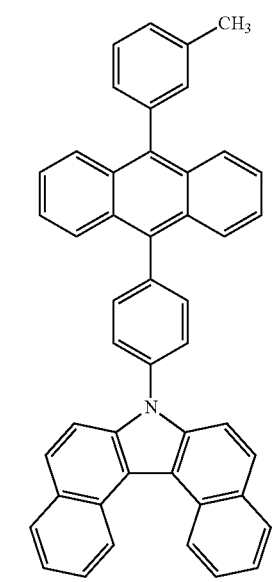
(121)
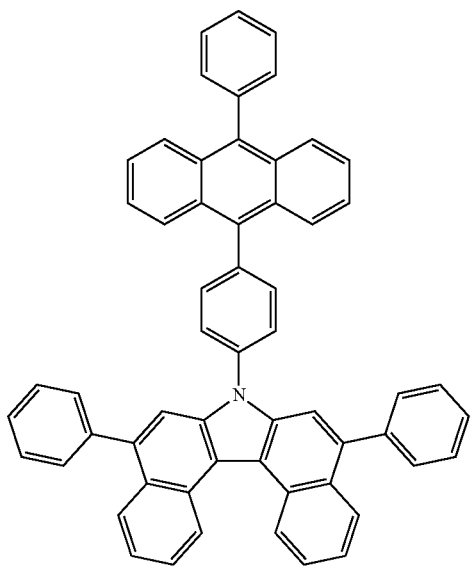
(122)
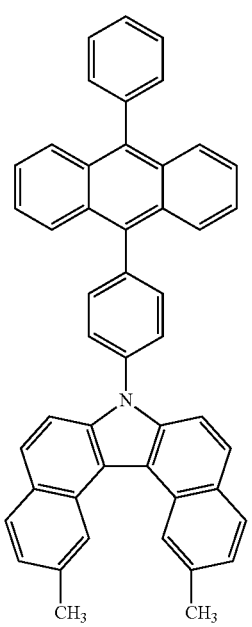
(123)
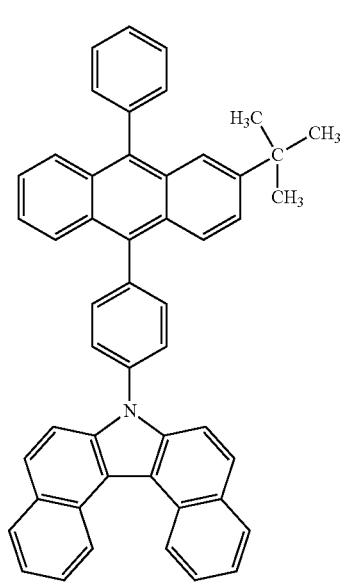

(124)
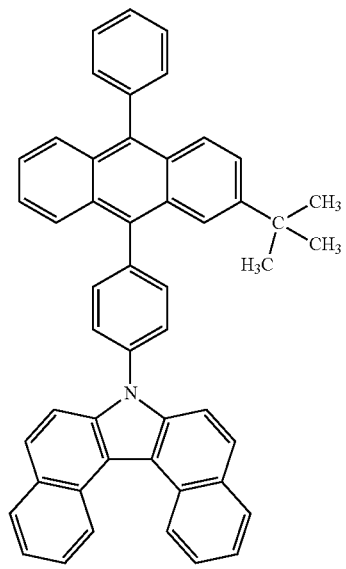
(125)
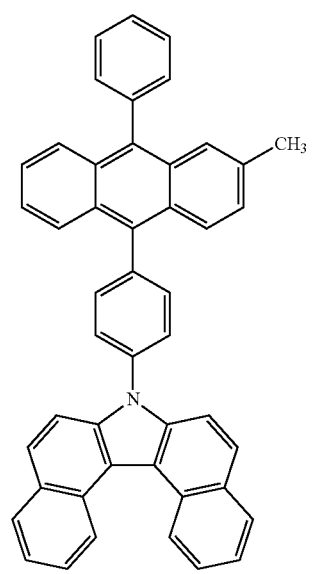
(126)
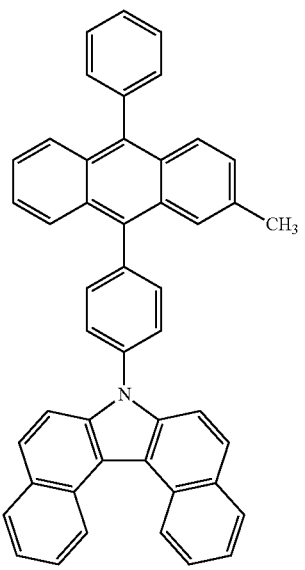
(127)
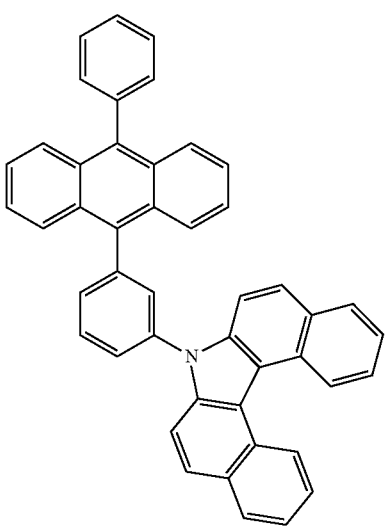
(128)
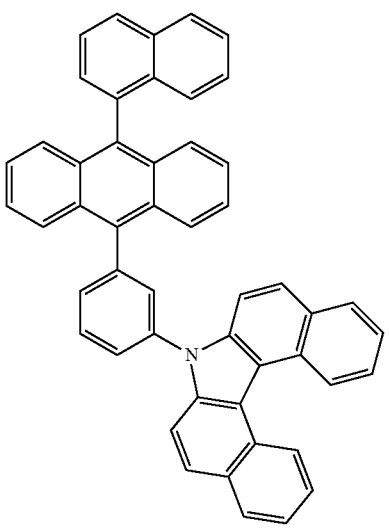

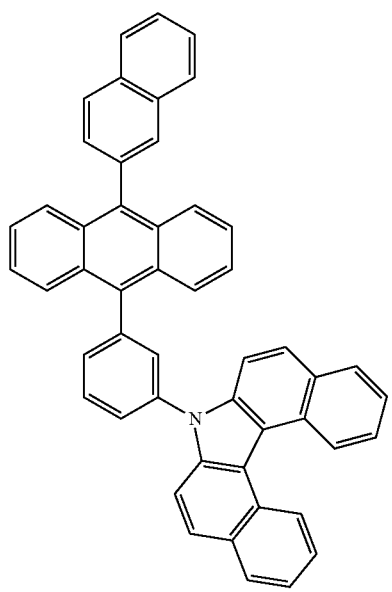
(129)
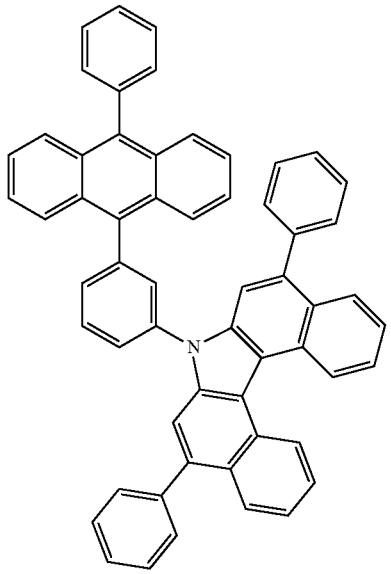
(131)
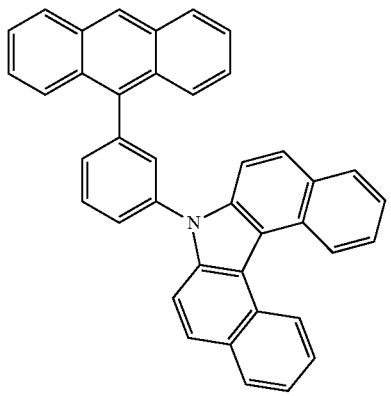
(132)
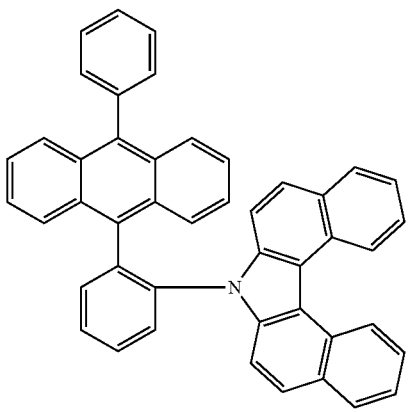
(133)

(134)

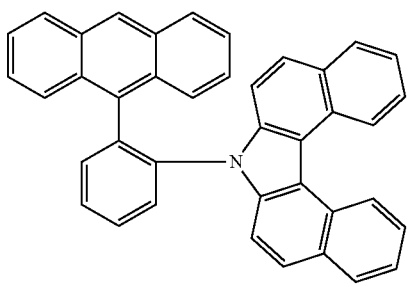

(135)

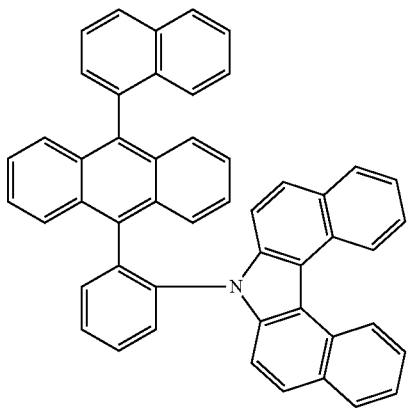

(136)

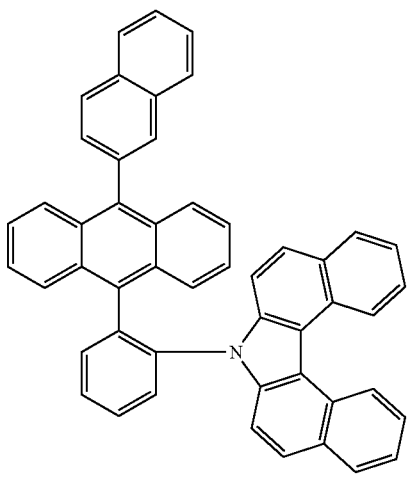

Since a dibenzo[c,g]carbazole compound described above has an excellent carrier-transport property, it is suitable as a carrier-transport material or a host material. Accordingly, a light-emitting element having low driving voltage can also be provided. Further, a dibenzo[c,g]carbazole compound in this embodiment has excellent stability to oxidation and reduction. Accordingly, a light-emitting element using a dibenzo[c,g]carbazole compound can be a light-emitting element having a long lifetime. Furthermore, a dibenzo[c,g]carbazole compound in this embodiment has a sufficiently wide band gap, and accordingly, even when it is used as a host material of a blue fluorescent material, a light-emitting element with high emission efficiency can be obtained.

Embodiment 3

Next, in this embodiment, a method of synthesizing the dibenzo[c,g]carbazole compound represented by the general formula (G1) is described. A variety of reactions can be applied to the method of synthesizing the dibenzo[c,g]carbazole compound. For example, synthesis reactions described below enable the synthesis of the dibenzo[c,g]carbazole compound represented by the general formula (G1). Note that the method of synthesizing a dibenzo[c,g]carbazole compound of one embodiment of the present invention is not limited to the following synthesis methods.

Synthesis Method of Dibenzo[c,g]carbazole Compound Represented by General Formula (G1)

The dibenzo[c,g]carbazole compound (G1) of the present invention can be synthesized in accordance with a synthesis scheme (A-1) illustrated below. Specifically, an anthracene compound (compound 1) and a dibenzo[c,g]carbazole compound (compound 2) undergo coupling, whereby the dibenzo[c,g]carbazole compound (G1) of the present invention can be obtained.

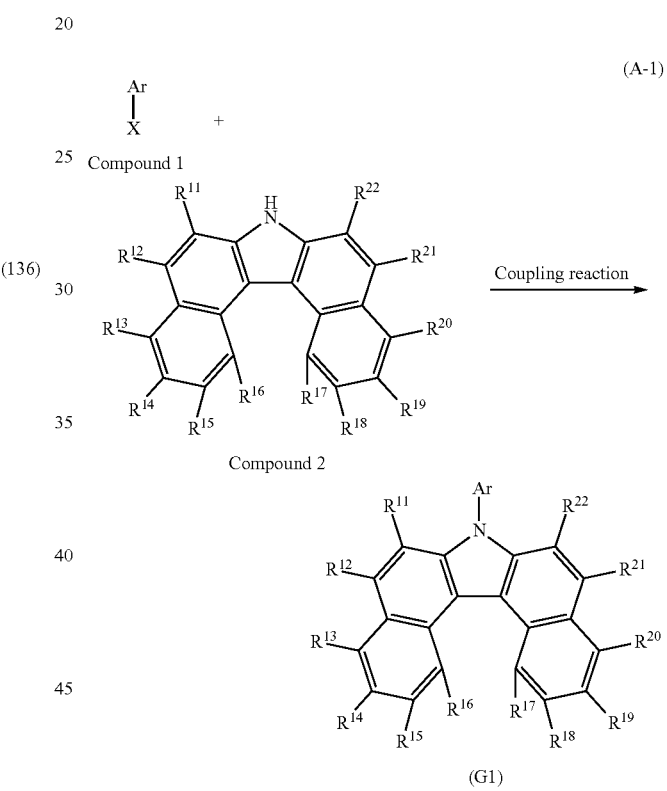

In the synthesis scheme (A-1), Ar represents a substituted or unsubstituted aryl group which has 14 to 30 carbon atoms and includes at least an anthracene skeleton. Further, $R^{11}$ to $R^{22}$ each independently represent any of hydrogen, an alkyl group having 1 to 4 carbon atoms, and an aryl group having 6 to 12 carbon atoms.

In the case where a Hartwig-Buchwald reaction using a palladium catalyst is performed in the synthesis scheme (A-1), X represents a halogen or a triflate group. As the halogen, iodine, bromine, or chlorine is preferable. A palladium catalyst using a palladium compound such as bis(dibenzylideneacetone)palladium(0) or palladium(II)acetate and a ligand that coordinates to the palladium compound, such as tri(tert-butyl)phosphine, tri(n-hexyl)phosphine, or tricyclohexylphosphine, is used for the reaction. As a base, an organic base such as sodium tert-butoxide, an inorganic base such as potassium carbonate or sodium carbonate, and the like can be used for the reaction. In the case where a solvent is used, toluene, xylene, benzene, tetrahydrofuran, or the like can be used. Note that reagents which can be used for the reaction are not limited to the above.

In the case where an Ullmann reaction using copper or a copper compound is performed in the synthesis scheme (A-1), X represents a halogen. As the halogen, iodine, bromine, or chlorine is preferable. As a catalyst, copper or a copper compound is used for the reaction. As the base which is used, an inorganic base such as potassium carbonate can be given. Examples of solvents which can be used for the reaction are 1,3-dimethyl-3,4,5,6-tetrahydro-2(1H)-pyrimidinone (DMPU), toluene, xylene, benzene, and the like. In an Ullmann reaction, DMPU or xylene, which has a high boiling point, is preferably used, in which case the object of the synthesis can be obtained in a shorter time and a higher yield at a reaction temperature of 100° C. or more. A reaction temperature of 150° C. or more is further preferred and accordingly DMPU is more preferably used. Note that reagents which can be used for the reaction are not limited to the above.

In the above manner, a dibenzo[c,g]carbazole compound described in Embodiment 2 can be synthesized.

Embodiment 4

In this embodiment is described an example of the mode where a dibenzo[c,g]carbazole compound described in Embodiment 2 is used for an active layer of a vertical transistor (static induction transistor: SIT), which is a kind of an organic semiconductor element.

Figure 2:
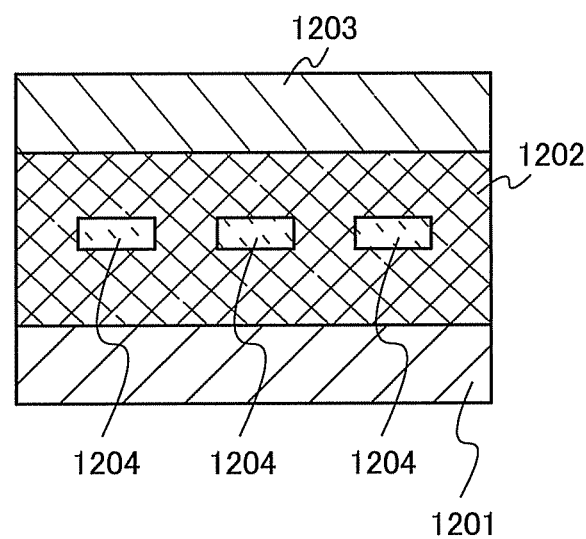
FIG. 2 is a conceptual diagram of an organic semiconductor element.

As illustrated in FIG. 2, the element has a structure in which a thin-film active layer 1202 containing a dibenzo[c,g]carbazole compound described in Embodiment 2 is provided between a source electrode 1201 and a drain electrode 1203, and a gate electrode 1204 is embedded in the active layer 1202. The gate electrode 1204 is electrically connected to a means for applying a gate voltage, and the source electrode 1201 and the drain electrode 1203 are electrically connected to a means for controlling a voltage between a source electrode and a drain electrode.

In such an element structure, when a voltage is applied between the source electrode and the drain electrode without applying a voltage to the gate electrode, current flows (on state). Then, by application of a voltage to the gate electrode in that state, a depletion layer is formed in the periphery of the gate electrode 1204, and the current ceases flowing (off state). With such a mechanism, the element operates as a transistor.

Like a light-emitting element, a vertical transistor should contain a material that can achieve both a high carrier-transport property and high film quality for an active layer; a dibenzo[c,g]carbazole compound described in Embodiment 2 meets such a requirement and therefore can be suitably used.

Embodiment 5

In this embodiment, a detailed example of the structure of a light-emitting element described in Embodiment 1 is described below with reference to FIG. 1A.

A light-emitting element in this embodiment includes a plurality of layers between a pair of electrodes. In this embodiment, the light-emitting element includes a first electrode 101, a second electrode 102, and an EL layer 103, which is provided between the first electrode 101 and the second electrode 102. Note that in this embodiment, the first electrode 101 functions as an anode and the second electrode 102 functions as a cathode. In other words, when a voltage is applied between the first electrode 101 and the second electrode 102 so that the potential of the first electrode 101 is higher than that of the second electrode 102, light emission can be obtained. A light-emitting element in this embodiment is a light-emitting element in which a dibenzo[c,g]carbazole compound is used for any of layers in the EL layer 103.

For the first electrode 101, any of metals, alloys, electrically conductive compounds, and mixtures thereof which have a high work function (specifically, a work function of 4.0 eV or more) or the like is preferably used. Specifically, for example, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), and the like can be given. Films of these electrically conductive metal oxides are usually formed by sputtering but may be formed by application of a sol-gel method or the like. For example, indium oxide-zinc oxide can be formed by a sputtering method using a target in which zinc oxide is added to indium oxide at 1 wt % to 20 wt %. Moreover, indium oxide containing tungsten oxide and zinc oxide (IWZO) can be formed by a sputtering method using a target in which tungsten oxide is added to indium oxide at 0.5 wt % to 5 wt % and zinc oxide is added to indium oxide at 0.1 wt % to 1 wt %. Besides, gold (Au), platinum (Pt), nickel (Ni), tungsten (W), chromium (Cr), molybdenum (Mo), iron (Fe), cobalt (Co), copper (Cu), palladium (Pd), graphene, nitrides of metal materials (e.g., titanium nitride), and the like can be given.

There is no particular limitation on a stacked structure of the EL layer 103. The EL layer 103 can be formed by combining a layer that contains a substance having a high electron-transport property, a layer that contains a substance having a high hole-transport property, a layer that contains a substance having a high electron-injection property, a layer that contains a substance having a high hole-injection property, a layer that contains a bipolar substance (a substance having a high electron-transport and hole-transport property), and the like as appropriate. For example, the EL layer 103 can be formed by combining a hole-injection layer, a hole-transport layer, a light-emitting layer, an electron-transport layer, an electron-injection layer, and the like as appropriate. In this embodiment, the EL layer 103 has a structure in which a hole-injection layer 111, a hole-transport layer 112, a light-emitting layer 113, an electron-transport layer 114, and an electron-injection layer 115 are stacked in this order over the first electrode 101. Materials included in the layers are specifically given below.

The hole-injection layer 111 is a layer containing a substance having a high hole-injection property. Molybdenum oxide, vanadium oxide, ruthenium oxide, tungsten oxide, manganese oxide, or the like can be used. Alternatively, the hole-injection layer 111 can be formed with a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), a high molecular compound such as poly(ethylenedioxythiophene)/poly(styrenesulfonic acid) (PEDOT/PSS), or the like.

Alternatively, a composite material in which a substance having a high hole-transport property contains a substance having an acceptor property can be used for the hole-injection layer 111. Note that the use of such a substance having a high hole-transport property which contains a substance having an acceptor property enables selection of a material used to form an electrode regardless of its work function. In other words, besides a material having a high work function, a material having a low work function can also be used for the first electrode 101. As the substance having an acceptor property, 7,7,8,8-tetracyano-2,3,5,6-tetrafluoroquinodimethane (abbreviation: $F_4$-TCNQ), chloranil, and the like can be given. In addition, transition metal oxides can be given. Oxides of the metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable in that their electron-accepting property is high. Among these, molybdenum oxide is especially preferable in that it is stable in the air, has a low hygroscopic property, and is easily treated.

As the substance having a high hole-transport property used for the composite material, any of a variety of compounds such as aromatic amine compounds, carbazole derivatives, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ cm$^2$/Vs or more is preferably used. Further, other than these substances, any substance that has a property of transporting more holes than electrons may be used. Organic compounds that can be used as the substance having a high hole-transport property in the composite material are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole derivatives that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole derivatives that can be used for the composite material are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbons that can be used for the composite material are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. Thus, an aromatic hydrocarbon having 14 to 42 carbon atoms or more and having a hole mobility of $1 \times 10^{-6}$ cm$^2$/Vs is more preferably used.

Note that the aromatic hydrocarbons that can be used for the composite material may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

The hole-transport layer 112 is a layer that contains a substance having a high hole-transport property. Examples of the substance having a high hole-transport property are aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like. The substances mentioned here are mainly ones that have a hole mobility of $10^{-6}$ cm$^2$/Vs or more. An organic compound given as an example of the substance having a high hole-transport property in the composite material described above can also be used for the hole-transport layer 112. A high molecular compound such as poly(N-vinylcarbazole) (abbreviation: PVK) or poly(4-vinyltriphenylamine) (abbreviation: PVTPA) can also be used. However, other than these substances, a substance that has a property of transporting more holes than electrons may be used. Further, the layer that includes a substance having a high hole-transport property is not limited to a single layer, and may be a stack of two or more layers including any of the above substances.

A dibenzo[c,g]carbazole compound described in Embodiment 2 may be used as a material included in the hole-transport layer 112.

The light-emitting layer 113 is a layer containing a light-emitting substance. The light-emitting layer 113 may be formed with a film containing only a light-emitting substance or a film in which an emission center substance is dispersed into a host material.

There is no particular limitation on a material that can be used as the light-emitting substance or the emission center substance in the light-emitting layer 113, and light emitted from the material may be either fluorescence or phosphorescence. Examples of the above light-emitting substance or emission center substance are the following substances: fluorescent substances such as N,N'-bis[4-(9-phenyl-9H-fluoren-9-yl)phenyl]-N,N'-diphenyl-pyrene-1,6-diamine (abbreviation: 1,6-FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM); and phosphorescent substances such as bis[2-(3',5'-bistrifluoromethylphenyl)pyridinato-N,C$^{2'}$]iridium(III)picolinate (abbreviation: Ir(CF$_3$ppy)$_2$(pic)), bis[2-(4',6'-difluorophenyl)pyridinato-N,C$^{2'}$]iridium(III)acetylacetonate (abbreviation: FIracac), tris(2-phenylpyridinato)iridium(III)(abbreviation: Ir(ppy)$_3$), bis(2-phenylpyridinato)iridium(III)acetylacetonate (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III)acetylacetonate (abbreviation: Ir(bzq)$_2$(acac)), bis(2,4-diphenyl-1,3-oxazolato-N,C$^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)), bis[2-(2'-benzo[4,5-α]thienyl)pyridinato-N,C$^{3'}$]iridium(III)(acetylacetonate) (abbreviation: Ir(btp)$_2$(acac)), bis(1-phenylisoquinolinato-N,C$^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphine platinum(II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)). Note that a dibenzo[c,g]carbazole compound described in Embodiment 2 can also be used as a light-emitting material or an emission center material. The dibenzo[c,g]carbazole compound is an emission center substance which emits light having a spectrum in a range from purple to blue.

Although there is no particular limitation on a material that can be used as the host material described above, any of the following substances can be used for the host material, for example: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[g,p]chysene derivatives can be given, and specific examples are 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N''',N'''-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), and the like. Further, a dibenzo[c,g]carbazole compound described in Embodiment 2 can also be suitably used as a host material. One or more substances having a wider energy gap than the emission center substance described above is preferably selected from these substances and known substances. Moreover, in the case where the emission center substance is a substance which emits phosphorescence, a substance having higher triplet excitation energy (energy difference between a ground state and a triplet excitation state) than the emission center substance can be selected as the host material.

Note that a dibenzo[c,g]carbazole compound described in Embodiment 2 can be suitably used in a light-emitting element whose emission center substance is a substance which emits blue fluorescence. This is because the wide band gap of the dibenzo[c,g]carbazole compound enables a substance which emits blue fluorescence to be effectively excited, so that a light-emitting element which provides blue fluorescence with high emission efficiency can be easily provided. Further, since a dibenzo[c,g]carbazole compound described in Embodiment 2 has an excellent carrier-transport property, a light-emitting element having low driving voltage can be provided.

Note that the light-emitting layer 113 can also be a stack of two or more layers. For example, in the case where the light-emitting layer 113 is formed by stacking a first light-emitting layer and a second light-emitting layer in that order over the hole-transport layer, a substance having a hole-transport property is used for the host material of the first light-emitting layer and a substance having an electron-transport property is used for the host material of the second light-emitting layer.

In the case where the light-emitting layer having the above-described structure includes a plurality of materials, co-evaporation by a vacuum evaporation method can be used, or alternatively an inkjet method, a spin coating method, a dip coating method, or the like with a solution of the materials can be used.

The electron-transport layer 114 is a layer containing a substance having a high electron-transport property. For example, a layer containing a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq). Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. A dibenzo[c,g]carbazole compound described in Embodiment 2 can also be suitably used. The substances mentioned here mainly have an electron mobility of $10^{-6}$ cm$^2$/Vs or more. Note that other than these substances, a substance that has a property of transporting more electrons than holes may be used for the electron-transport layer.

Furthermore, the electron-transport layer 114 is not limited to a single layer and may be a stack of two or more layers containing any of the above substances.

Between the electron-transport layer and the light-emitting layer, a layer that controls transport of electron carriers may be provided. This is a layer formed by addition of a small amount of a substance having a high electron-trapping property to a material having a high electron-transport property as described above, and the layer is capable of adjusting carrier balance by suppressing transport of electron carriers. Such a structure is very effective in preventing a problem (such as a reduction in element lifetime) caused when electrons pass through the light-emitting layer.

Since a dibenzo[c,g]carbazole compound described in Embodiment 2 has an excellent carrier-transport property, by using the compound as a material of the electron-transport layer 114, a light-emitting element having low driving voltage can be easily provided. Further, since the dibenzo[c,g]carbazole compound has a wide band gap, even when the compound is used as a material of the electron-transport layer 114 adjacent to the light-emitting layer 113, there is less possibility of deactivation of the excitation energy of the emission center substance and a light-emitting element with high emission efficiency can be easily provided.

In addition, an electron-injection layer 115 may be provided in contact with the second electrode 102 between the electron-transport layer 114 and the second electrode 102. For the electron-injection layer 115, an alkali metal, an alkaline earth metal, or a compound thereof such as lithium fluoride (LiF), cesium fluoride (CsF), or calcium fluoride (CaF$_2$) can be used. For example, a layer that is formed with a substance having an electron-transport property and contains an alkali metal, an alkaline earth metal, magnesium (Mg), or a compound thereof can be used. For example, an Alq layer containing magnesium (Mg) can be used. Note that electron injection from the second electrode 102 is efficiently performed with the use of a layer that is formed with a substance having an electron-transport property and contains an alkali metal or an alkaline earth metal as the electron-injection layer 115, which is preferable.

For the second electrode 102, any of metals, alloys, electrically conductive compounds, and mixtures thereof which have a low work function (specifically, a work function of 3.8 eV or less) or the like can be used. Specific examples of such a cathode material include elements that belong to Groups 1 and 2 in the periodic table, i.e., alkali metals such as lithium (Li) and cesium (Cs), and alkaline earth metals such as magnesium (Mg), calcium (Ca), and strontium (Sr), alloys thereof (e.g., MgAg or AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these electrically conductive materials can be formed by a sputtering method, an inkjet method, a spin coating method, or the like.

Further, any of a variety of methods can be used to form the EL layer 103 regardless whether it is a dry process or a wet process. For example, a vacuum evaporation method, an inkjet method, a spin coating method or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

In the light-emitting element having the above-described structure, current flows due to a potential difference between the first electrode 101 and the second electrode 102, and holes and electrons recombine in the light-emitting layer 113 which contains a substance having a high light-emitting property, so that light is emitted. That is, a light-emitting region is formed in the light-emitting layer 113.

Light emission is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light emission is extracted through the first electrode 101. In the case where only the second electrode 102 is a light-transmitting electrode, light emission is extracted through the second electrode 102. In the case where both the first electrode 101 and the second electrode 102 are light-transmitting electrodes, light emission is extracted through the first electrode 101 and the second electrode 102.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented.

Further, in order that transfer of energy from an exciton generated in the light-emitting layer can be suppressed, preferably, the hole-transport layer and the electron-transport layer which are in direct contact with the light-emitting layer, particularly a carrier-transport layer in contact with a side closer to the light-emitting region in the light-emitting layer 113 is formed with a substance having a larger energy gap than the light-emitting substance of the light-emitting layer or the emission center substance included in the light-emitting layer.

In a light-emitting element in this embodiment, when a dibenzo[c,g]carbazole compound described in Embodiment 2 is used for the hole-transport layer or the electron-transport layer, efficient light emission is possible even with the light-emitting substance or the emission center substance that has a large energy gap and emits blue fluorescence or green phosphorescence with large triplet excitation energy (an energy difference between a ground state and a triplet excited state); thus, a light-emitting element having high emission efficiency can be obtained. Accordingly, a light-emitting element having higher emission efficiency and lower power consumption can be provided. In addition, a light-emitting element capable of light emission with high color purity can be provided. Further, a dibenzo[c,g]carbazole compound described in Embodiment 2 has an excellent carrier-transport property; thus, a light-emitting element having low driving voltage can be provided.

Since a dibenzo[c,g]carbazole compound described in Embodiment 2 is stable to repetition of oxidation and reduction, a light-emitting element having a long lifetime can be easily provided by using the dibenzo[c,g]carbazole compound.

A light-emitting element in this embodiment is preferably fabricated over a substrate of glass, plastic, or the like. As the way of stacking layers over the substrate, layers may be sequentially stacked on the first electrode 101 side or sequentially stacked on the second electrode side.

In a light-emitting device, although one light-emitting element may be formed over one substrate, a plurality of light-emitting elements may be formed over one substrate.

With a plurality of light-emitting elements as described above formed over one substrate, a lighting device in which elements are separated or a passive-matrix light-emitting device can be manufactured.

A light-emitting element may be formed over an electrode electrically connected to a thin film transistor (TFT), for example, which is formed over a substrate formed of glass, plastic, or the like, so that an active matrix light-emitting device in which the TFT controls the drive of the light-emitting element can be manufactured.

Note that there is no particular limitation on the structure of the TFT, which may be a staggered TFT or an inverted staggered TFT. In addition, crystallinity of a semiconductor used for the TFT is not particularly limited either; an amorphous semiconductor or a crystalline semiconductor may be used. In addition, a driver circuit formed in a TFT substrate may be formed with an n-type TFT and a p-type TFT, or with either an n-type TFT or a p-type TFT.

Embodiment 6

In this embodiment is described one mode of a light-emitting element having a structure in which a plurality of light-emitting units is stacked (hereinafter, also referred to as stacked-type element), with reference to FIG. 1B. This light-emitting element is a light-emitting element including a plurality of light-emitting units between a first electrode and a second electrode. Each light-emitting unit can have the same structure as the EL layer 103 which is described in Embodiment 5. In other words, the light-emitting element described in Embodiment 5 is a light-emitting element having one light-emitting unit while the light-emitting element described in Embodiment 6 is a light-emitting element having a plurality of light-emitting units.

Figure 1B:
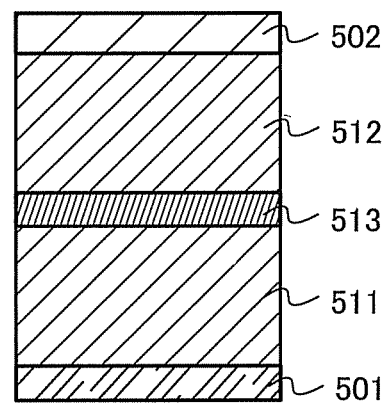

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond, respectively, to the first electrode 101 and the second electrode 102 in Embodiment 5, and materials described in Embodiment 5 can be used. Further, the structures of the first light-emitting unit 511 and the second light-emitting unit 512 may be the same or different.

The charge generation layer 513 contains a composite material of an organic compound and a metal oxide. This composite material of an organic compound and a metal oxide is the composite material described in Embodiment 5, and contains an organic compound and a metal oxide such as vanadium oxide, molybdenum oxide, or tungsten oxide. As the organic compound, any of a variety of compounds such as aromatic amine compounds, dibenzo[c,g]carbazole compounds, carbazole compounds, aromatic hydrocarbons, and high molecular compounds (oligomers, dendrimers, polymers, or the like) can be used. Note that as the organic compound, the one having a hole mobility of $10^{-6}$ cm$^2$/Vs or more as an organic compound having a hole-transport property is preferably used. Further, other than these substances, any substance that has a property of transporting more holes than electrons may be used. Since a composite of an organic compound and a metal oxide is excellent in carrier-injection property and carrier-transport property, low voltage driving and low current driving can be achieved.

The charge generation layer 513 may be formed in such a way that a layer containing the composite material of an organic compound and a metal oxide is combined with a layer containing another material, for example, with a layer that contains a compound selected from substances having an electron-donating property and a compound having a high electron-transport property. The charge generation layer 513 may be formed in such a way that a layer containing the composite material of an organic compound and a metal oxide is combined with a transparent conductive film.

The charge generation layer 513 provided between the first light-emitting unit 511 and the second light-emitting unit 512 may have any structure as far as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as far as the layer injects electrons into the first light-emitting unit 511 and holes into the second light-emitting unit 512 when a voltage is applied such that the voltage of the first electrode is higher than that of the second electrode.

Although the light-emitting element having two light-emitting units is described in this embodiment, the present invention can be similarly applied to a light-emitting element in which three or more light-emitting units are stacked. By arrangement of a plurality of light-emitting units, which are partitioned by the charge-generation layer between a pair of electrodes, as in a light-emitting element in this embodiment, light emission in a high luminance region can be realized with current density kept low, thus a light-emitting element having a long lifetime can be realized. Further, in application to lighting devices, a voltage drop due to resistance of an electrode material can be reduced and accordingly light emission in a large area is possible. Moreover, a light-emitting device having low driving voltage and lower power consumption can be realized.

By making the light-emitting units emit light of different colors from each other, the light-emitting element can provide light emission of a desired color as a whole. For example, by forming a light-emitting element having two light-emitting units such that the emission color of the first light-emitting unit and the emission color of the second light-emitting unit are complementary colors, the light-emitting element can provide white light emission as a whole. Note that the word "complementary" means color relationship in which an achromatic color is obtained when colors are mixed. In other words, when lights obtained from substances which emit light of complementary colors are mixed, white emission can be obtained. Further, the same can be applied to a light-emitting element having three light-emitting units. For example, the light-emitting element as a whole can provide white light emission when the emission color of the first light-emitting unit is red, the emission color of the second light-emitting unit is green, and the emission color of the third light-emitting unit is blue.

Since a light-emitting element in this embodiment includes a dibenzo[c,g]carbazole compound described in Embodiment 2, the light-emitting element can be a light-emitting element having high emission efficiency, a light-emitting element having low driving voltage, or a light-emitting element having a long lifetime. In addition, since light emission with high color purity which is derived from the emission center substance can be obtained from the light-emitting unit including the dibenzo[c,g]carbazole compound, color adjustment of the light-emitting element as a whole is easy.

Note that this embodiment can be combined with any of the other embodiments as appropriate.

Embodiment 7

In this embodiment, a light-emitting device using a light-emitting element including a dibenzo[c,g]carbazole compound described in Embodiment 2 (light-emitting element described in Embodiment 1) is described.

In this embodiment, the light-emitting device using a light-emitting element including a dibenzo[c,g]carbazole compound described in Embodiment 2 (light-emitting element described in Embodiment 1) is described with reference to FIGS. 3A and 3B. Note that FIG. 3A is a top view illustrating the light-emitting device and FIG. 3B is a cross-sectional view of FIG. 3A taken along the lines A-B and C-D. This light-emitting device includes a driver circuit portion (source line driver circuit) 601, a pixel portion 602, and a driver circuit portion (gate line driver circuit) 603, which are to control light emission of the light-emitting element and illustrated with dotted lines. Moreover, a reference numeral 604 denotes a sealing substrate; 625, a desiccant; 605, a sealing material; and 607, a space surrounded by the sealing material 605.

Reference numeral 608 denotes a wiring for transmitting signals to be inputted into the source line driver circuit 601 and the gate line driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is described with reference to FIG. 3B. The driver circuit portion and the pixel portion are formed over an element substrate 610; the source line driver circuit 601, which is a driver circuit portion, and one of the pixels in the pixel portion 602 are illustrated here As the source line driver circuit 601, a CMOS circuit in which an n-channel TFT 623 and a p-channel TFT 624 are combined is formed. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit may not necessarily be formed over the substrate, and the driver circuit can be formed outside, not over the substrate.

The pixel portion 602 includes a plurality of pixels including a switching TFT 611, a current controlling TFT 612, and a first electrode 613 electrically connected to a drain of the current controlling TFT 612. Note that to cover an end portion of the first electrode 613, an insulator 614 is formed, for which a positive type photosensitive acrylic resin film is used here.

In order to improve coverage, the insulator 614 is formed to have a curved surface with curvature at its upper or lower end portion. For example, in the case where positive photosensitive acrylic is used for a material of the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. Note that when the stacked structure is used, the first electrode 613 has low resistance as a wiring, forms a favorable ohmic contact, and can function as an anode.

In addition, the EL layer 616 is formed by any of a variety of methods such as an evaporation method using a shadow mask, an inkjet method, and a spin coating method. The EL layer 616 includes a dibenzo[c,g]carbazole compound described in Embodiment 2. Further, another material included in the EL layer 616 may be a low molecular compound or a high molecular compound (which may be an oligomer and a dendrimer).

As a material used for the second electrode 617, which is formed over the EL layer 616 and functions as a cathode, a material having a low work function (e.g., Al, Mg, Li, Ca, or an alloy or compound thereof, such as MgAg, MgIn, or AlLi) is preferably used. In the case where light generated in the EL layer 616 passes through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the EL layer 616, and the second electrode 617. The light-emitting element has the structure described in Embodiment 5. In the light-emitting device of this embodiment, the pixel portion, which includes a plurality of light-emitting elements, may include both the light-emitting element described in Embodiment 1 with the structure described in Embodiment 5 or 6 and a light-emitting element with a structure other than those.

Further, the sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with filler, and may be filled with an inert gas (such as nitrogen or argon), or the sealing material 605.

An epoxy-based resin or glass frit is preferably used for the sealing material 605. It is preferable that such a material do not transmit moisture or oxygen as much as possible. As the sealing substrate 604, a glass substrate, a quartz substrate, or a plastic substrate formed of fiberglass reinforced plastic (FRP), polyvinyl fluoride (PVF), polyester, acrylic, or the like can be used.

As described above, the light-emitting device using a light-emitting element including a dibenzo[c,g]carbazole compound described in Embodiment 2 (light-emitting element described in Embodiment 1) can be obtained.

A light-emitting element including a dibenzo[c,g]carbazole compound described in Embodiment 2 (light-emitting element described in Embodiment 1) is used in the light-emitting device in this embodiment, and thus a light-emitting device having favorable characteristics can be obtained. Specifically, since a dibenzo[c,g]carbazole compound described in Embodiment 2 has a large energy gap and high triplet excitation energy and can suppress energy transfer from a light-emitting substance, a light-emitting element having high emission efficiency can be provided, and accordingly a light-emitting device having reduced power consumption can be provided. In addition, a light-emitting element having low driving voltage can be provided, and accordingly a light-emitting device having low driving voltage can be provided. Further, since a light-emitting element using a dibenzo[c,g]carbazole compound described in Embodiment 2 (light-emitting element described in Embodiment 1) is a light-emitting element having a long lifetime, a light-emitting device with high reliability can be provided.

Figure 4A:
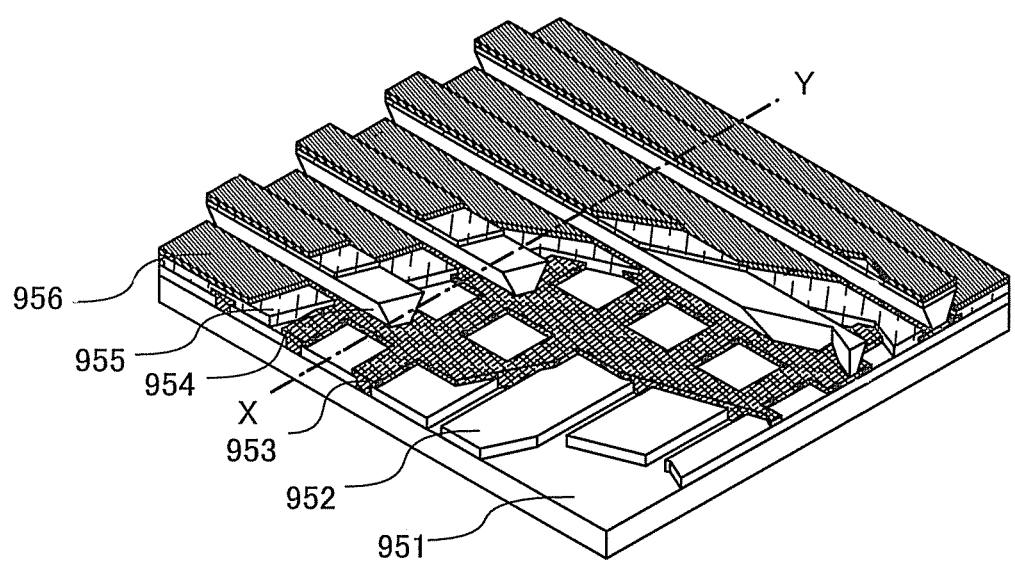
FIGS. 4A and 4B are conceptual diagrams of a passive matrix light-emitting device.
Figure 4B:
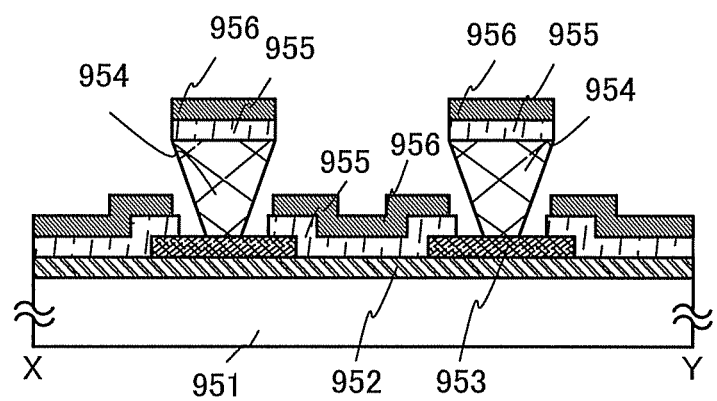

Although an active matrix light-emitting device is described in this embodiment as described above, a passive matrix light-emitting device may be manufactured. FIGS. 4A and 4B illustrate a passive matrix light-emitting device manufactured using the present invention. FIG. 4A is a perspective view of the light-emitting device, and FIG. 4B is a cross-sectional view taken along line X-Y in FIG. 4A. In FIGS. 4A and 4B, over a substrate 951, an EL layer 955 is provided between an electrode 952 and an electrode 956. An end portion of the electrode 952 is covered with an insulating layer 953. In addition, a partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). The partition layer 954 thus provided can prevent defects in the light-emitting element due to static electricity or the like. The passive matrix light-emitting device can also be driven while power consumption is kept low, by including a light-emitting element described in Embodiment 1 which is capable of operating at low voltage and includes a dibenzo[c,g]carbazole compound described in Embodiment 2. In addition, the light-emitting device can be driven while power consumption is kept low, by including a light-emitting element described in Embodiment 1 which includes a dibenzo[c,g]carbazole compound described in Embodiment 2 and accordingly has high emission efficiency. Further, the light-emitting device can have high reliability by including a light-emitting element described in Embodiment 1 which includes a dibenzo[c,g]carbazole compound described in Embodiment 2.

Embodiment 8

Figure 5A:
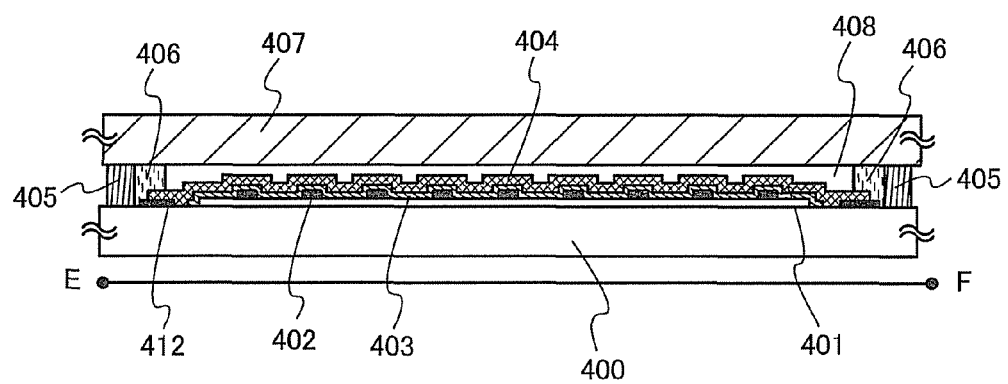
FIGS. 5A and 5B are conceptual diagrams of a lighting device.
Figure 5B:
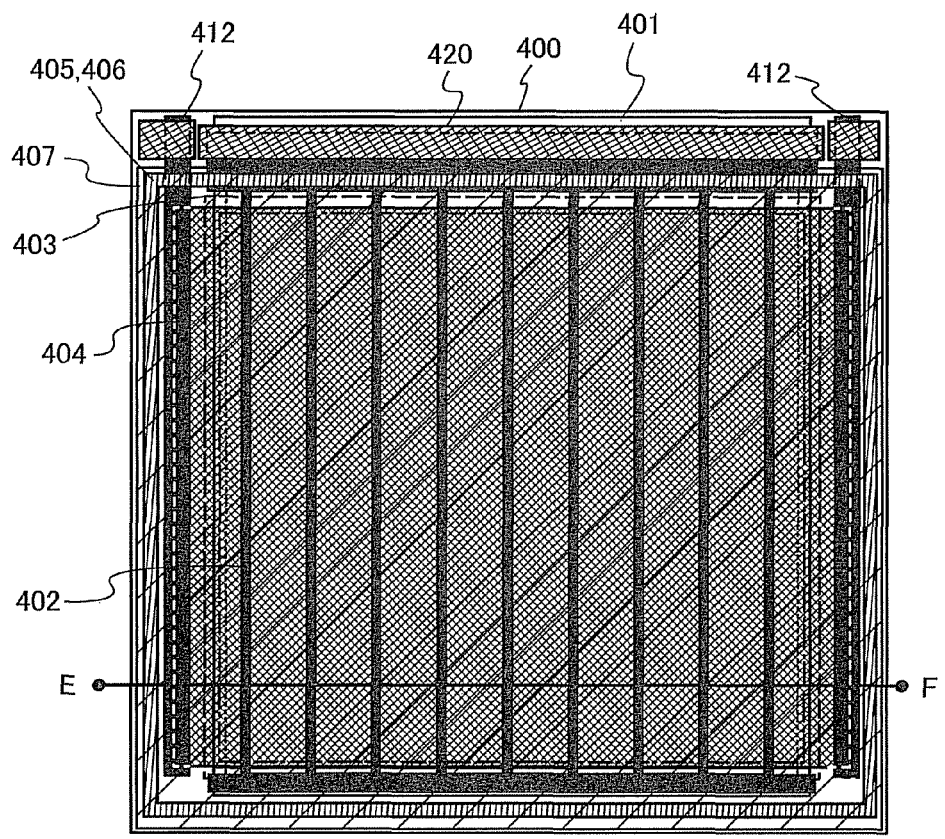

In this embodiment, an example in which a light-emitting element using a dibenzo[c,g]carbazole compound described in Embodiment 2 (light-emitting element described in Embodiment 1) is used for a lighting device is described with reference to FIGS. 5A and 5B. FIG. 5B is a top view of the lighting device, and FIG. 5A is a cross-sectional view taken along the line E-F in FIG. 5B.

In the lighting device in this embodiment, a first electrode 401 is formed over a substrate 400 which is a support and has a light-transmitting property. The first electrode 401 corresponds to the first electrode 101 in Embodiment 5.

An auxiliary electrode 402 is provided over the first electrode 401. Since light emission is extracted through the first electrode 401 side in the example given in this embodiment, the first electrode 401 is formed using a material having a light-transmitting property. The auxiliary electrode 402 is provided in order to compensate for the low conductivity of the material having a light-transmitting property, and has a function of suppressing luminance unevenness in a light emission surface due to voltage drop caused by the high resistance of the first electrode 401. The auxiliary electrode 402 is formed using a material having at least higher conductivity than the material of the first electrode 401, and is preferably formed using a material having high conductivity such as aluminum. Note that surfaces of the auxiliary electrode 402 other than a portion thereof in contact with the first electrode 401 are preferably covered with an insulating layer. With such a structure, light emission over the upper portion of the auxiliary electrode 402, which cannot be extracted, can be suppressed, so that a reduction in power efficiency due to reactive current can be suppressed. Note that a pad 412 for applying a voltage to a second electrode 404 may be formed at the same time as the formation of the auxiliary electrode 402.

An EL layer 403 is formed over the first electrode 401 and the auxiliary electrode 402. The EL layer 403 corresponds to a structure of the EL layer 103 in Embodiment 5 or a structure combining the light-emitting units 511 and 512 and the charge generation layer 513. See the explanations of these structures. Note that the EL layer 403 is preferably formed to be slightly larger than the first electrode 401 when seen from above, in which case the EL layer 403 can also serve as an insulating layer that suppresses a short circuit between the first electrode 401 and the second electrode 404.

The second electrode 404 is formed to cover the EL layer 403. The second electrode 404 corresponds to the second electrode 102 in Embodiment 5 and has a similar structure. In this embodiment, it is preferable that the second electrode 404 be formed using a material having high reflectance because light emission is extracted through the first electrode 401 side. In this embodiment, the second electrode 404 is connected to the pad 412, whereby voltage is applied.

As described above, the lighting device described in this embodiment includes a light-emitting element including the first electrode 401, the EL layer 403, and the second electrode 404 (and the auxiliary electrode 402). Since the light-emitting element is a light-emitting element with high emission efficiency, the lighting device in this embodiment can be a lighting device having low power consumption. Further, since the light-emitting element is a light-emitting element having low driving voltage, the lighting device in this embodiment can be a lighting device having low power consumption. Furthermore, since the light-emitting element is a light-emitting element having high reliability, the lighting device in this embodiment can be a lighting device having high reliability.

The light-emitting element having the above structure is fixed to a sealing substrate 407 with sealing materials 405 and 406 and sealing is performed, whereby the lighting device is completed. It is possible to use only either the sealing material 405 or the sealing material 406. In addition, the inner sealing material 406 can be mixed with a desiccant which enables moisture to be adsorbed, increasing reliability.

When extended to the outside of the sealing materials 405 and 406, the pad 412, the first electrode 401, and the auxiliary electrode 402 can each partly serve as external input terminal. An IC chip 420 mounted with a converter or the like may be provided over the external input terminals.

As described above, since the lighting device described in this embodiment includes a light-emitting element including a dibenzo[c,g]carbazole compound described in Embodiment 2 (light-emitting element described in Embodiment 1) as an EL element, the lighting device can be a lighting device having low power consumption, a lighting device with low driving voltage, or a lighting device with high reliability.

Embodiment 9

In this embodiment, examples of an electronic device including a light-emitting element including a dibenzo[c,g]carbazole compound described in Embodiment 2 (light-emitting element described in Embodiment 1) are described. A light-emitting element including a dibenzo[c,g]carbazole compound described in Embodiment 2 (light-emitting element described in Embodiment 1) is a light-emitting element having favorable emission efficiency and reduced power consumption. Accordingly, an electronic device described in this embodiment can be an electronic device including a light-emitting portion having reduced power consumption. Further, since a light-emitting element including a dibenzo[c,g]carbazole compound described in Embodiment 2 (light-emitting element described in Embodiment 1) is a light-emitting element having low driving voltage, an electronic device described in this embodiment can be an electronic device having low driving voltage. Furthermore, since a light-emitting element including a dibenzo[c,g]carbazole compound described in Embodiment 2 (light-emitting element described in Embodiment 1) is a light-emitting element having a long lifetime, an electronic device described in this embodiment can be an electronic device having high reliability.

Examples of the electronic devices to which the above light-emitting element is applied are television sets (also referred to as televisions or television receivers), monitors of computers or the like, cameras such as digital cameras or digital video cameras, digital photo frames, mobile phone sets (also referred to as mobile phones or mobile phone devices), portable game machines, portable information terminals, audio reproducing devices, large-sized game machines such as pachinko machines, and the like. Specific examples of these electronic devices are described below.

Figure 6A:
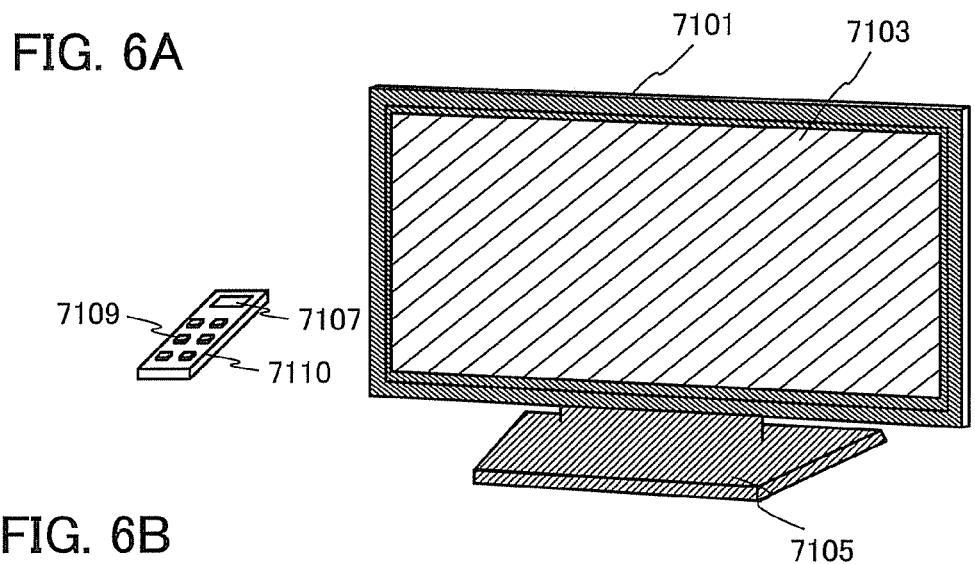
FIGS. 6A to 6D illustrates electronic devices.

FIG. 6A illustrates an example of a television set. In the television set, a display portion 7103 is incorporated in a housing 7101. In addition, here, the housing 7101 is supported by a stand 7105. The display portion 7103 enables display of images and includes light-emitting elements arranged in a matrix, each of which is a light-emitting element including a dibenzo[c,g]carbazole compound described in Embodiment 2 (light-emitting element described in Embodiment 1). The light-emitting elements can have high emission efficiency. Further, the light-emitting elements can have low driving voltage. Furthermore, the light-emitting elements can have a long lifetime. Accordingly, the television device that has the display portion 7103 including the light-emitting elements can be a television device having reduced power consumption. Further, the television device can be a television device having low driving voltage. Furthermore, the television device can be a television device having high reliability.

Operation of the television set can be performed with an operation switch of the housing 7101 or a separate remote control 7110. With operation keys 7109 of the remote control 7110, channels and volume can be controlled and images displayed on the display portion 7103 can be controlled. Furthermore, the remote control 7110 may be provided with a display portion 7107 for displaying data output from the remote control 7110.

Note that the television set is provided with a receiver, a modem, and the like. With the receiver, a general television broadcast can be received. Furthermore, when the television set is connected to a communication network by wired or wireless connection via the modem, one-way (from a transmitter to a receiver) or two-way (between a transmitter and a receiver, between receivers, or the like) data communication can be performed.

Figure 6B:
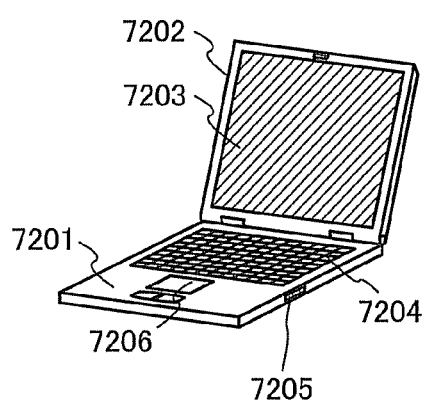

FIG. 6B illustrates a computer having a main body 7201, a housing 7202, a display portion 7203, a keyboard 7204, an external connection port 7205, a pointing device 7206, and the like. Note that this computer is manufactured by using light-emitting elements arranged in a matrix, each of which is a light-emitting element including a dibenzo[c,g]carbazole compound described in Embodiment 2 (light-emitting element described in Embodiment 1). The light-emitting elements can have high emission efficiency. Further, the light-emitting elements can have low driving voltage. Furthermore, the light-emitting elements can have a long lifetime. Accordingly, the computer that has the display portion 7203 including the light-emitting elements can be a computer having reduced power consumption. Further, the computer can be a computer having low driving voltage. Furthermore, the computer can be a computer having high reliability.

Figure 6C:
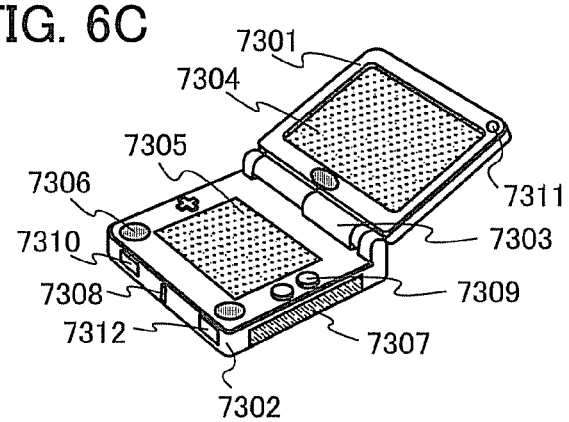

FIG. 6C illustrates a portable game machine having two housings, a housing 7301 and a housing 7302, which are connected with a joint portion 7303 so that the portable game machine can be opened or folded. A display portion 7304 including light-emitting elements arranged in a matrix which are described in Embodiment 1 and is incorporated in the housing 7301, and a display portion 7305 is incorporated in the housing 7302. A display portion 7304 is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. It is needless to say that the structure of the portable game machine is not limited to the above as far as the display portion including light-emitting elements arranged in a matrix, each of which is a light-emitting element including a dibenzo[c,g]carbazole compound described in Embodiment 2 (light-emitting element described in Embodiment 1) is used as at least either the display portion 7304 or the display portion 7305, or both, and the structure can include other accessories as appropriate. The portable game machine illustrated in FIG. 6C has a function of reading out a program or data stored in a storage medium to display it on the display portion, and a function of sharing information with another portable game machine by wireless communication. The portable game machine illustrated in FIG. 6C can have a variety of functions without limitation to the above. Since the light-emitting elements used in the display portion 7304 have high emission efficiency, the portable game machine including the above-described display portion 7304 can be a portable game machine having reduced power consumption. Since the light-emitting elements used in the display portion 7304 has low driving voltage, the portable game machine can also be a portable game machine having low driving voltage. Furthermore, since the light-emitting elements used in the display portion 7304 has high reliability, the portable game machine can also be a portable game machine having high reliability.

Figure 6D:
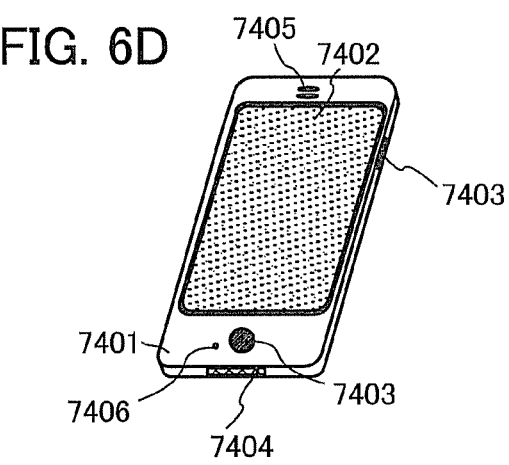

FIG. 6D illustrates an example of a mobile phone. A mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using the light-emitting device for the display portion 7402. Note that the cellular phone 7400 has the display portion 7402 including light-emitting elements arranged in a matrix, each of which is a light-emitting element including a dibenzo[c,g] carbazole compound described in Embodiment 2 (light-emitting element described in Embodiment 1). The light-emitting elements can have high emission efficiency. Further, the light-emitting elements can have low driving voltage. Furthermore, the light-emitting elements can have a long lifetime. Accordingly, the cellular phone that has the display portion 7402 including the light-emitting elements can be a cellular phone having reduced power consumption. Further, the mobile phone can be a mobile phone having low driving voltage. Furthermore, the mobile phone can be a mobile phone having high reliability.

When the display portion 7402 of the mobile phone 7400 illustrated in FIG. 6D is touched with a finger or the like, data can be input to the mobile phone. In this case, operations such as making a call and creating mail can be performed by touching the display portion 7402 with a finger or the like.

There are mainly three screen modes of the display portion 7402. The first mode is a display mode mainly for displaying images. The second mode is an input mode mainly for inputting data of a character and the like. The third mode is a display-and-input mode in which two modes of the display mode and the input mode are combined.

For example, in the case of making a call or creating an e-mail, a text input mode mainly for inputting a character is selected for the display portion 7402 so that a character displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone, display on the screen of the display portion 7402 can be automatically switched by determining the orientation of the mobile phone (whether the mobile phone is placed horizontally or vertically for a landscape mode or a portrait mode).

The screen modes are switched by touching the display portion 7402 or operating the operation buttons 7403 of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

Note that the structure described in this embodiment can be combined with any of the structures described in Embodiments 1 to 8 as appropriate.

As described above, the application range of the light-emitting device having a light-emitting element including a dibenzo[c,g]carbazole compound described in Embodiment 2 (light-emitting element described in Embodiment 1) is wide so that this light-emitting device can be applied to electronic devices in a variety of fields. By use of a light-emitting element including a dibenzo[c,g]carbazole compound described in Embodiment 2, an electronic device having reduced power consumption can be obtained. In addition, an electronic device having low driving voltage can be obtained.

Figure 7:
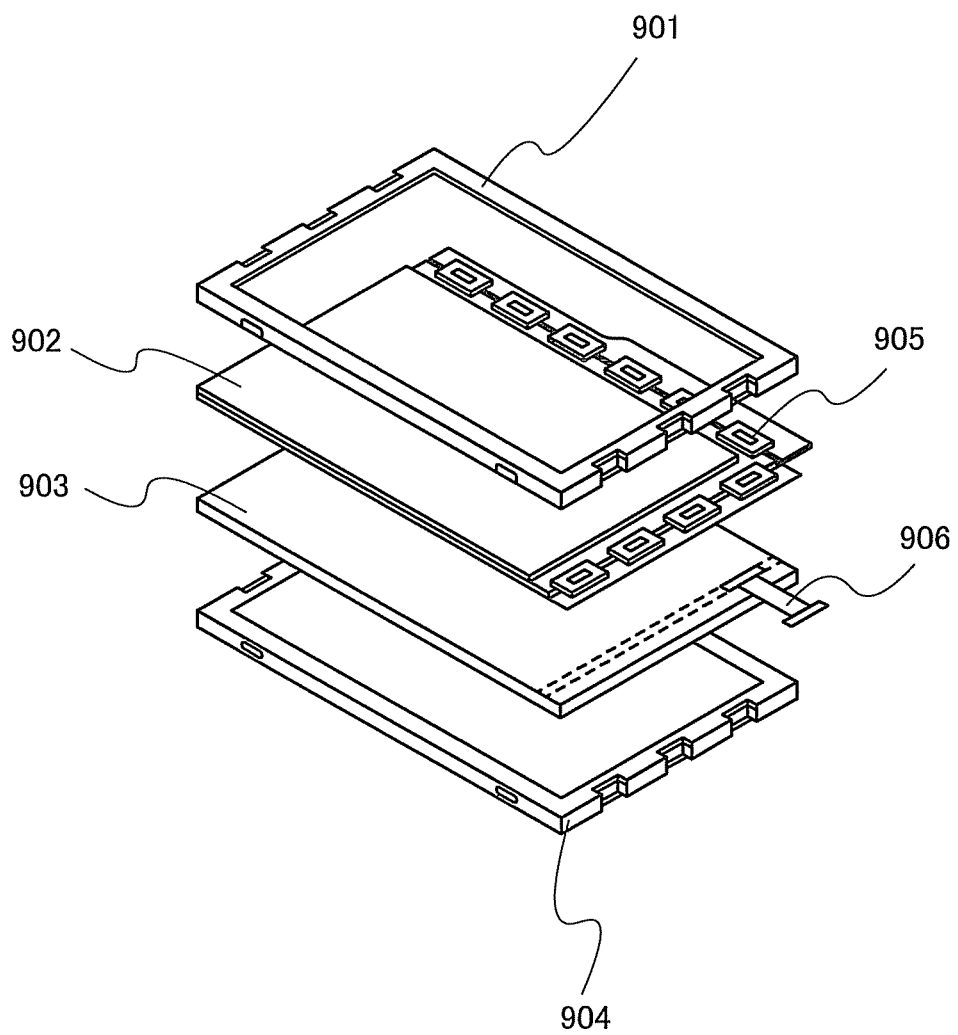
FIG. 7 illustrates a display device.

FIG. 7 illustrates an example of a liquid crystal display device using a light-emitting element including a dibenzo[c, g]carbazole compound described in Embodiment 2 (light-emitting element described in Embodiment 1) for a backlight. The liquid crystal display device illustrated in FIG. 7 includes a housing 901, a liquid crystal layer 902, a backlight 903, and a housing 904. The liquid crystal layer 902 is connected to a driver IC 905. A light-emitting element including a dibenzo [c,g]carbazole compound described in Embodiment 2 (light-emitting element described in Embodiment 1) is used in the backlight 903, to which a current is supplied through a terminal 906.

A light-emitting element including a dibenzo[c,g]carbazole compound described in Embodiment 2 (light-emitting element described in Embodiment 1) is used for the backlight of the liquid crystal display device, and thus a backlight having reduced power consumption can be obtained. In addition, use of a light-emitting element including a dibenzo[c,g] carbazole compound described in Embodiment 2 enables manufacture of a planar-emission lighting device and further a larger-area planar-emission lighting device; therefore, the backlight can be a larger-area backlight, and the liquid crystal display device can also be a larger-area device. Furthermore, the backlight using a light-emitting element including a dibenzo[c,g]carbazole compound described in Embodiment 2 (light-emitting element described in Embodiment 1) can be thinner than a conventional one; accordingly, the display device can also be thinner.

Figure 8:
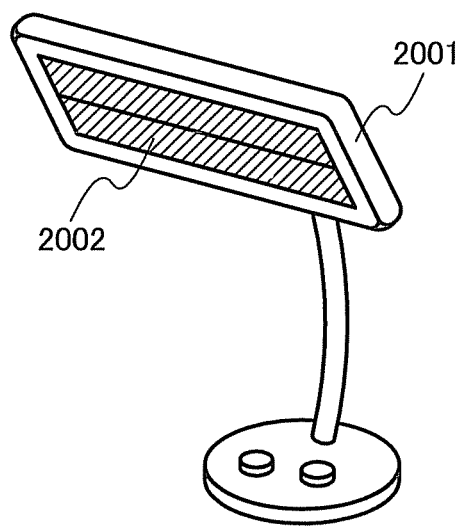
FIG. 8 illustrates a lighting device.

FIG. 8 illustrates an example in which a light-emitting element including a dibenzo[c,g]carbazole compound described in Embodiment 2 (light-emitting element described in Embodiment 1) is used for a table lamp which is a lighting device. The table lamp illustrated in FIG. 8 includes a housing 2001 and a light source 2002, and the light-emitting device described in Embodiment 8 is used for the light source 2002.

Figure 9:
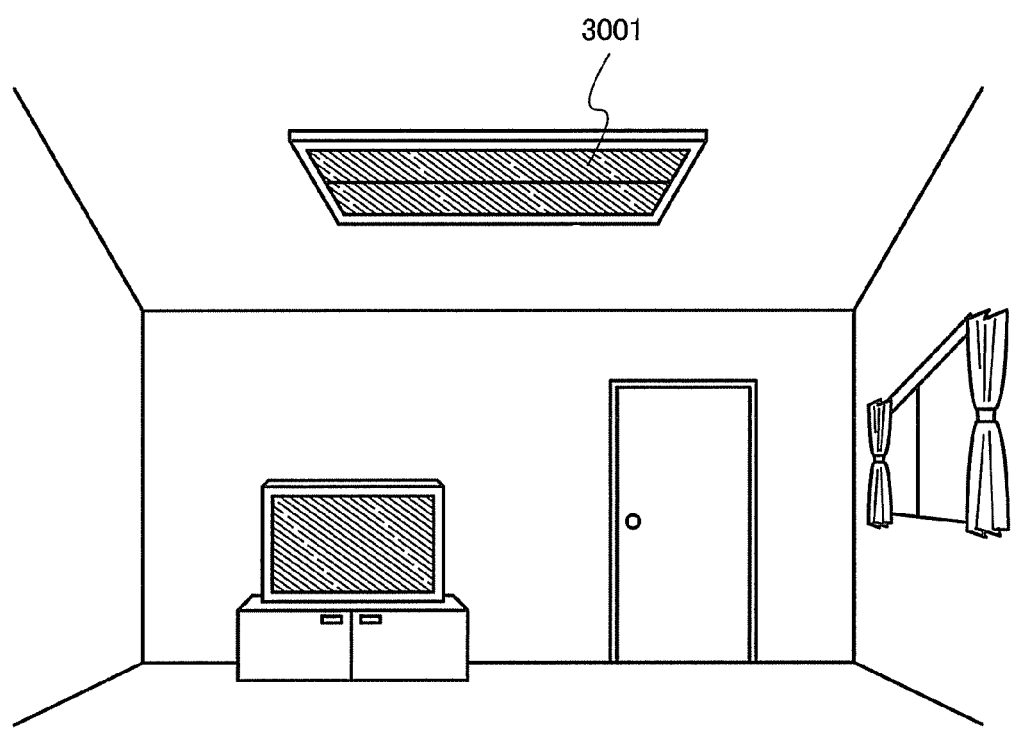
FIG. 9 illustrates lighting devices.

FIG. 9 illustrates an example in which a light-emitting element including a dibenzo[c,g]carbazole compound described in Embodiment 2 (light-emitting element described in Embodiment 1) is used for an indoor lighting device 3001. Since a light-emitting element including a dibenzo[c,g]carbazole compound described in Embodiment 2 has reduced power consumption, a lighting device that has reduced power consumption can be obtained. Further, since a light-emitting element including a dibenzo[c,g]carbazole compound described in Embodiment 2 can have a large area, the light-emitting element can be used for a large-area lighting device. Furthermore, since a light-emitting element including a dibenzo[c,g]carbazole compound described in Embodiment 2 is thin, the light-emitting element can be used for a lighting device having a reduced thickness.

Figure 10:
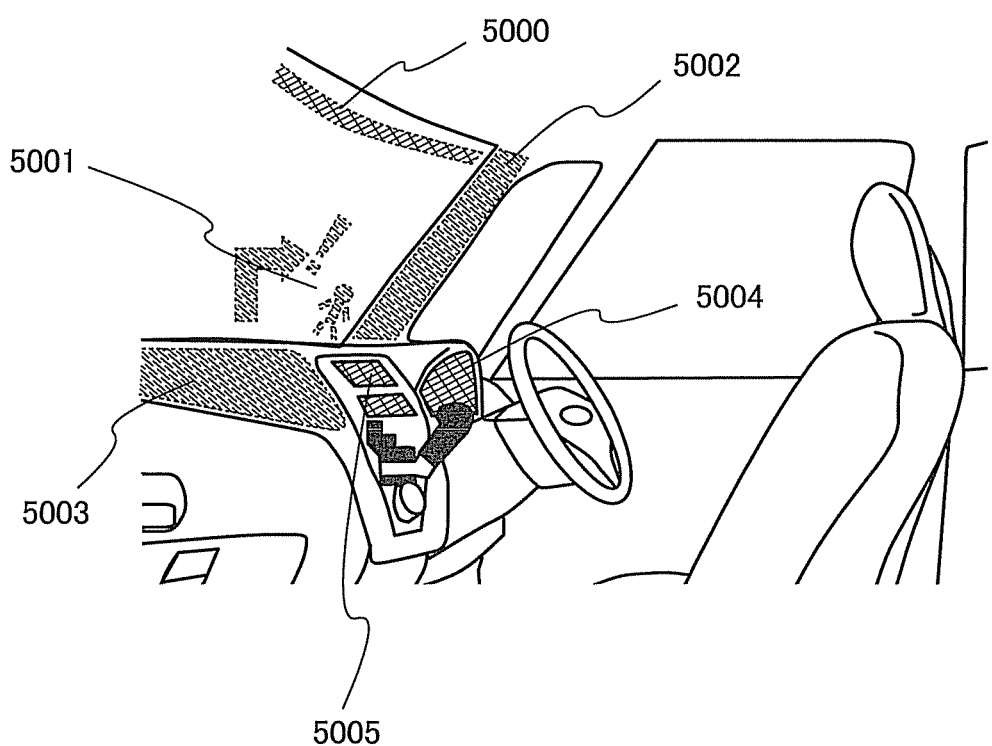
FIG. 10 illustrates in-vehicle display devices and lighting devices.

A light-emitting element including a dibenzo[c,g]carbazole compound described in Embodiment 2 (light-emitting element described in Embodiment 1) can also be used for an automobile windshield or dashboard. One mode in which the light-emitting elements including a dibenzo[c,g]carbazole compound described in Embodiment 1 are used for an automobile windshield and an automobile dashboard is illustrated in FIG. 10. Display regions 5000 to 5005 each include a light-emitting element including a dibenzo[c,g]carbazole compound described in Embodiment 2.

The display region 5000 and the display region 5001 are display devices which are provided in the automobile windshield and in which the light-emitting elements including a dibenzo[c,g]carbazole compound described in Embodiment 2 (i.e., each of which is a light-emitting element described in Embodiment 1) are incorporated. The light-emitting elements including a dibenzo[c,g]carbazole compound described in Embodiment 2 can be formed into so-called see-through display devices, through which the opposite side can be seen, by including a first electrode and a second electrode formed with electrodes having a light-transmitting property. Such see-through display devices can be provided even in the automobile windshield, without hindering the vision. Note that in the case where a transistor for driving is provided, a transistor having a light-transmitting property, such as an organic transistor using an organic semiconductor material or a transistor using an oxide semiconductor, is preferably used The display region 5002 is a display device which is provided in a pillar portion and in which a light-emitting element including a dibenzo[c,g]carbazole compound described in Embodiment 2 (light-emitting element described in Embodiment 1) is incorporated. The display region 5002 can compensate for the view hindered by the pillar portion by showing an image taken by an imaging element provided in the automobile body. Similarly, the display region 5003 provided in the dashboard can compensate for the view hindered by the automobile body by showing an image taken by an imaging element provided in the outside of the automobile body, which leads to elimination of blind areas and enhancement of safety. Showing an image so as to compensate for the area which a driver cannot see, makes it possible for the driver to confirm safety easily and comfortably.

The display region 5004 and the display region 5005 can provide a variety of kinds of information such as navigation data, a speedometer, a tachometer, a mileage, a fuel meter, a gearshift indicator, and air-condition setting. The content or layout of the display can be changed freely by a user as appropriate. Further, such information can also be shown by the display regions 5000 to 5003. Note that the display regions 5000 to 5005 can also be used as lighting devices.

A light-emitting element including a dibenzo[c,g]carbazole compound described in Embodiment 2 (light-emitting element described in Embodiment 1) can be a light-emitting element having low driving voltage or a light-emitting element having low power consumption. Accordingly, even when a number of large screens such as display regions 5000 to 5005 are provided, load on a battery can be reduced, which provides comfortable use. The light-emitting device and the lighting device each using a light-emitting element including a dibenzo[c,g]carbazole compound described in Embodiment 2 can be suitably used as an in-vehicle light-emitting device or lighting device.

Example 1

In this example, a synthesis method of 7-[4-(10-phenyl-9-anthryl)phenyl]-7H-dibenzo[c,g]carbazole (abbreviation: cgDBCzPA), which is a dibenzo[c,g]carbazole compound represented by the general formula (G1) described in Embodiment 2, is described in detail.

Step 1: Synthesis of
5,6,8,9-Tetrahydro-7H-dibenzo[c,g]carbazole

In a 100 mL three-neck flask were placed 1.0 g (20 mmol) of hydrazine monohydrate and 14 mL ethanol. To this solution in an ice bath was added dropwise 2.2 mL of a 1.7 M acetic acid aqueous solution with a dropping funnel. To this solution were added dropwise 10 g (68 mmol) of β-tetralone dissolved in 10 mL ethanol with a dropping funnel. This mixture was stirred at 80° C. for 7 hours, whereby a solid was precipitated. After the stirring, this mixture was added to about 50 mL of water and the mixture was stirred at room temperature for 30 minutes. After the stirring, this mixture was suction-filtered to collect a solid. Methanol/water in a 1:1 ratio was added to the collected solid and the mixture was irradiated with ultrasonic waves, and a solid was washed. After the washing, this mixture was suction-filtered and a solid was collected, giving 3.5 g of a yellow powder in a yield of 63%. A reaction scheme (a-1) of Step 1 is illustrated below.

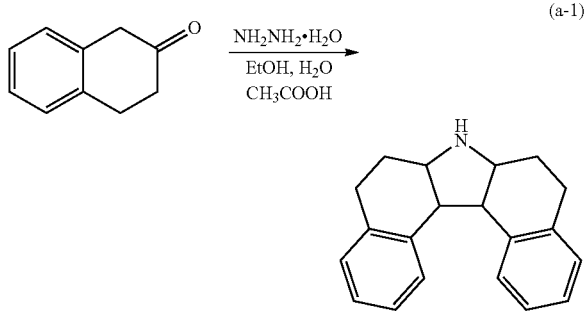

Step 2: Synthesis of 7H-Dibenzo[c,g]carbazole

In a 200 mL three-neck flask were placed 6.2 g of chloranil (25 mmol), 40 mL of xylene, and 3.5 g (12 mmol) of 5,6,8,9-tetrahydro-7H-benzo[c,g]carbazole suspended in 20 mL of xylene. This mixture was refluxed at 150° C. for 4 hours under a nitrogen stream. After reaction, this mixture cooled to room temperature, precipitating a solid. The precipitated solid was removed by suction filtration and a filtrate was obtained. The obtained filtrate was purified by silica gel column chromatography (developing solvent: toluene/hexane in a 2:1 ratio) to give a red solid. Recrystallization of the obtained solid from toluene/hexane gave pale-red needle-like crystals. The obtained crystals were again recrystallized from toluene/hexane, so that 2.5 g of white needle-like crystals were obtained in 78% yield. A reaction scheme (b-1) of Step 2 is illustrated below.

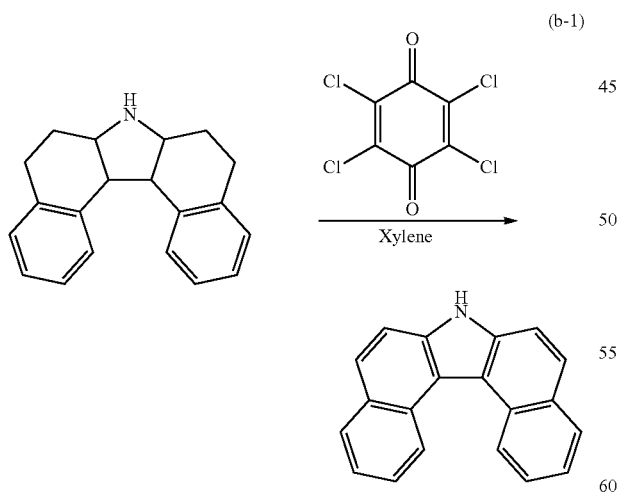

Step 3: Synthesis of 7-[4-(10-Phenyl-9-anthryl)phenyl]-7H-dibenzo[c,g]carbazole (cgDBCzPA)

In a 100 mL three-neck flask were placed 2.3 g (5.6 mmol) of 9-(4-bromophenyl)-10-phenylanthracene, 1.5 g (5.6 mol) of 7H-dibenzo[c,g]carbazole, and 1.2 g (12 mmol) of sodium tert-butoxide. After the air in the flask was replaced with nitrogen, to this mixture were added 30 mL of toluene and 2.8 mL of tri-(tert-butyl)phosphine (a 10 wt % hexane solution). This mixture was degassed by being stirred while the pressure was reduced. After the degassing, 0.16 g (0.28 mmol) of bis(dibenzylideneacetone)palladium(0) was added to this mixture. This mixture was stirred at 110° C. for 17 hours under a nitrogen stream, so that a solid was precipitated. The precipitated solid was removed by suction filtration. The collected solid was dissolved in about 30 mL of hot toluene, and this solution was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). A solid obtained by concentration of the filtrate was recrystallized from toluene/hexane to give 2.3 g of a pale yellow powder, which was the object of the synthesis, in a yield of 70%. A reaction scheme (c-1) of Step 3 is illustrated below.

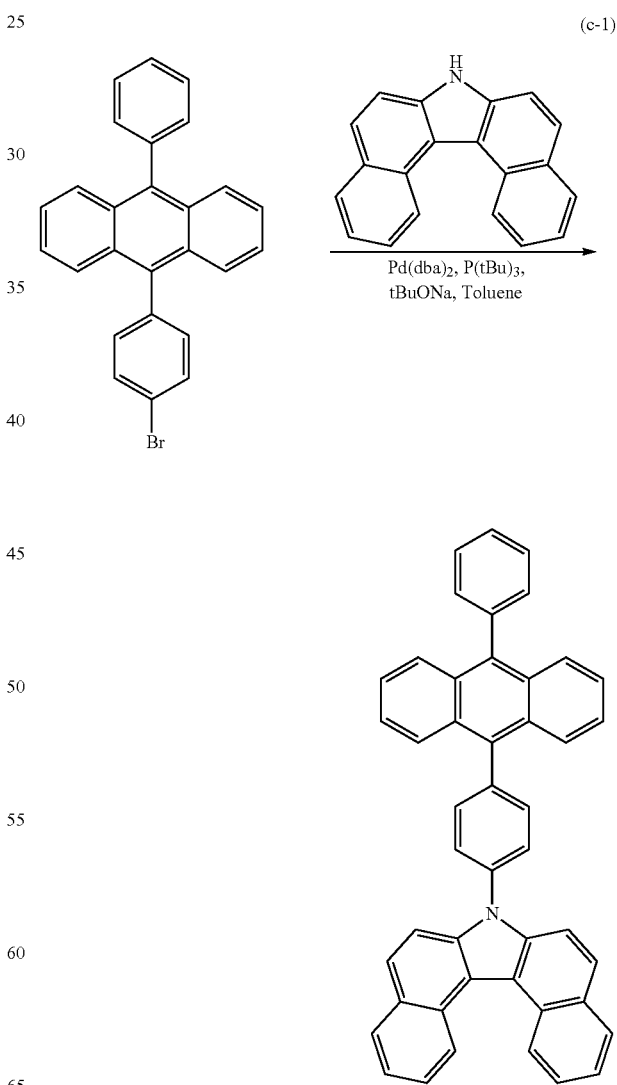

By a train sublimation method, 2.3 g of the obtained pale yellow powdery solid was purified by sublimation. In the sublimation purification, cgDBCzPA was heated at 310° C. under a pressure of 3.6 Pa with a flow rate of argon at 6.0 mL/min. After the sublimation purification, 2.1 g of a pale yellow solid of cgDBCzPA was recovered in 91% yield.

The obtained substance was measured by $^1$H NMR. The measurement data are shown below.

$^1$H NMR (CDCl$_3$, 300 MHz): δ=7.38-7.67 (m, 11H), 7.72-7.89 (m, 12H), 7.96 (d, J=8.7 Hz, 2H), 8.10 (d, J=7.2 Hz, 2H), 9.31 (d, J$_1$=8.1 Hz, 2H)

Figure 11A:
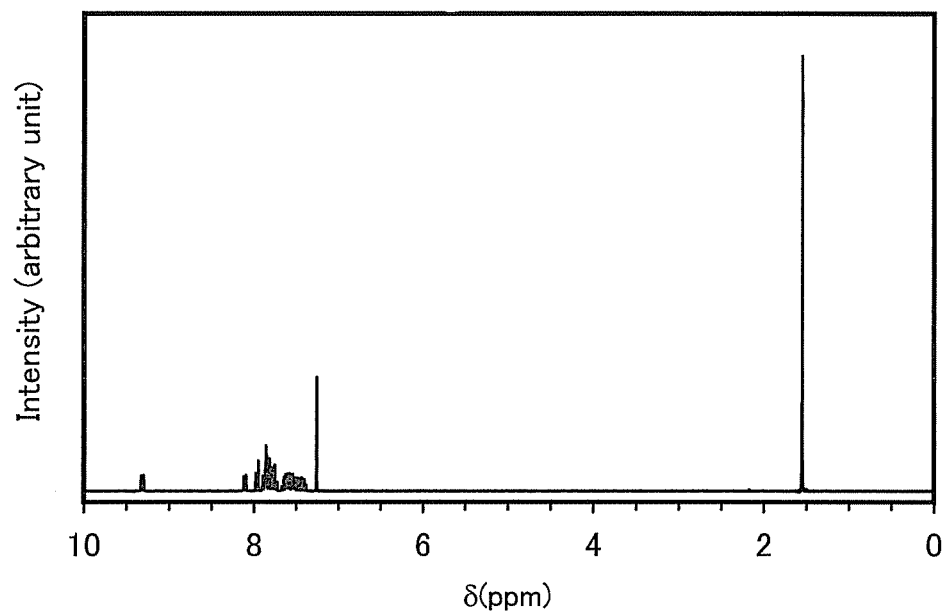
FIGS. 11A and 11B are NMR charts of cgDBCzPA.
Figure 11B:
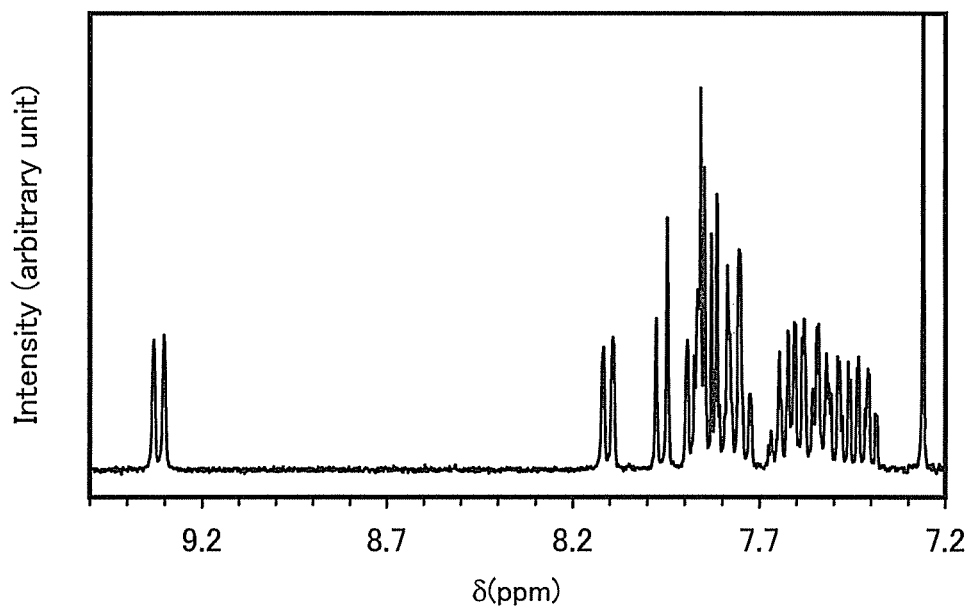

In addition, FIGS. 11A and 11B are $^1$H-NMR charts. The measurement results show that 7-[4-(10-phenyl-9-anthryl)phenyl]-7H-dibenzo[c,g]carbazole (abbreviation: cgDBCzPA) represented by the above structural formula was obtained.

Figure 12A:
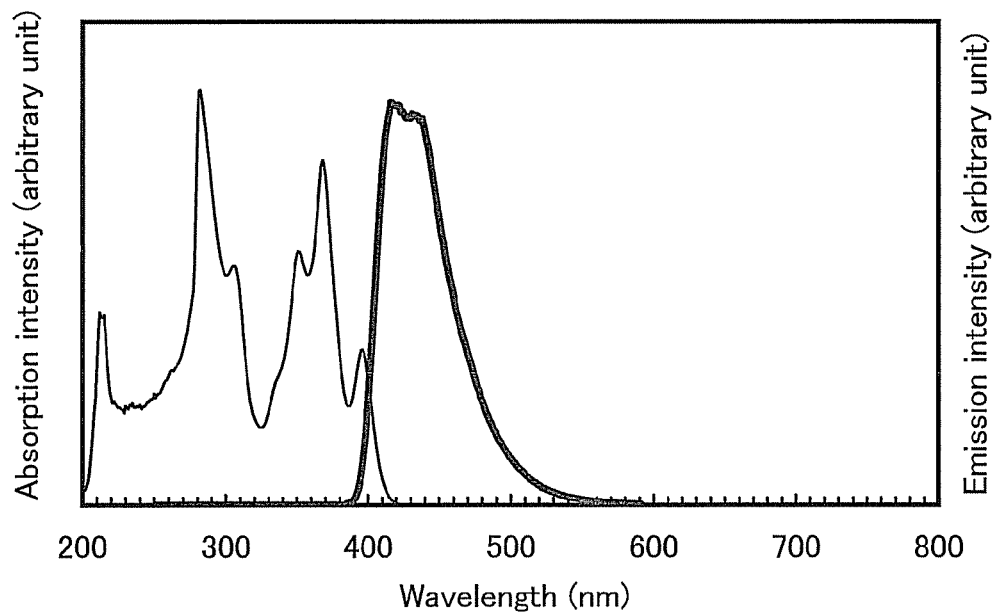
FIGS. 12A and 12B each show an absorption and emission spectra of cgDBCzPA.
Figure 12B:
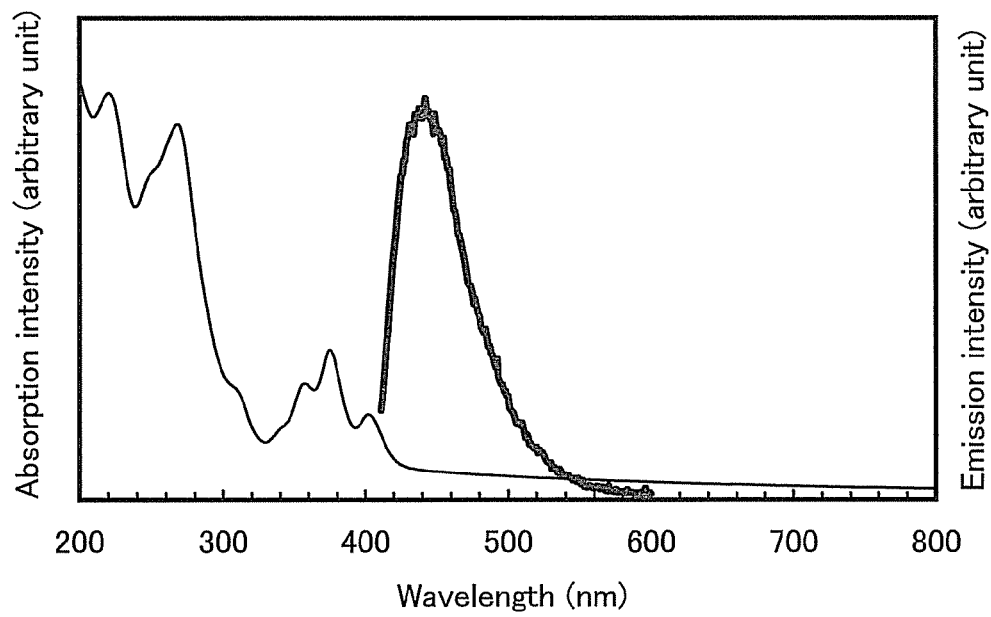

Next, absorption and emission spectra of cgDBCzPA in a toluene solution of cgDBCzPA are shown in FIG. 12A, and absorption and emission spectra of a thin film of cgDBCzPA are shown in FIG. 12B. The absorption spectra were measured using an ultraviolet-visible light spectrophotometer (V550 type manufactured by Japan Spectroscopy Corporation). A toluene solution of cgDBCzPA was put in a quartz cell and an absorption spectrum of cgDBCzPA in the toluene solution was measured. From this absorption spectrum, an absorption spectrum of the toluene solution measured with the quartz cell was subtracted, and the resultant value was shown in the drawing. In addition, as for the absorption spectrum of the thin film, a sample was prepared by evaporation of cgDBCzPA over a quartz substrate, and the absorption spectrum obtained by subtraction of an absorption spectrum of quartz from the absorption spectrum of this sample is shown in the drawing. As in the measurements of the absorption spectra, an ultraviolet-visible spectrophotometer (V550, manufactured by JASCO Corporation) was used for the measurements of the emission spectra. The emission spectrum of cgDBCzPA in a toluene solution of cgDBCzPA was measured with the toluene solution of cgDBCzPA put in a quartz cell, and the emission spectrum of the thin film was measured with a sample prepared by evaporation of cgDBCzPA over a quartz substrate. These show that the maximum absorption wavelengths of cgDBCzPA in the toluene solution of cgDBCzPA were around 396 nm, around 368 nm, around 351 nm, around 306 nm, and around 252 nm and that the maximum emission wavelengths thereof were around 417 nm and around 432 nm (an excitation wavelength of 369 nm). These also show that the maximum absorption wavelengths of the thin film were around 402 nm, around 375 nm, around 357 nm, around 343 nm, around 306 nm, around 268 nm, around 252 nm, and around 221 nm and that the largest maximum emission wavelength thereof was around 442 nm (an excitation wavelength of 402 nm).

Further, the ionization potential of a thin film of cgDBCzPA was measured by a photoelectron spectrometer (AC-2, manufactured by Riken Keiki, Co., Ltd.) in the air. The obtained value of the ionization potential was converted to a negative value, revealing that the HOMO level of cgDBCzPA was −5.72 eV. From the data of the absorption spectra of the thin film in FIGS. 12A and 12B, the absorption edge of cgDBCzPA, which was obtained from a Tauc plot with an assumption of direct transition, was 2.95 eV. Therefore, the optical energy gap of cgDBCzPA in the solid state was estimated at 2.95 eV; from the values of the HOMO level obtained above and this energy gap, the LUMO level of cgDBCzPA was able to be estimated at −2.77 eV. It was thus found that cgDBCzPA had a wide energy gap of 2.95 eV in the solid state.

The oxidation characteristics and reduction characteristics of cgDBCzPA were measured. These were examined by cyclic voltammetry (CV) measurements. An electrochemical analyzer (ALS model 600A or 600C, manufactured by BAS Inc.) was used for the measurements.

Further, as for a solution used for the CV measurements, dehydrated dimethylformamide (DMF, manufactured by Sigma-Aldrich Inc., 99.8%, Catalog No. 22705-6) was used as a solvent, and tetra-n-butylammonium perchlorate (n-Bu$_4$NClO$_4$, manufactured by Tokyo Chemical Industry Co., Ltd., Catalog No. T0836), which was a supporting electrolyte, was dissolved in the solvent such that the concentration was 100 mmol/L. Further, the object to be measured was dissolved in the solvent such that the concentration was 2 mmol/L. A platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag$^+$ electrode (RE-5 reference electrode for nonaqueous solvent, manufactured by BAS Inc.) was used as a reference electrode. Note that the measurements were conducted at room temperature (20 to 25° C.). The scan rate was set to 0.1 V/s through the CV measurements.

Figure 13A:
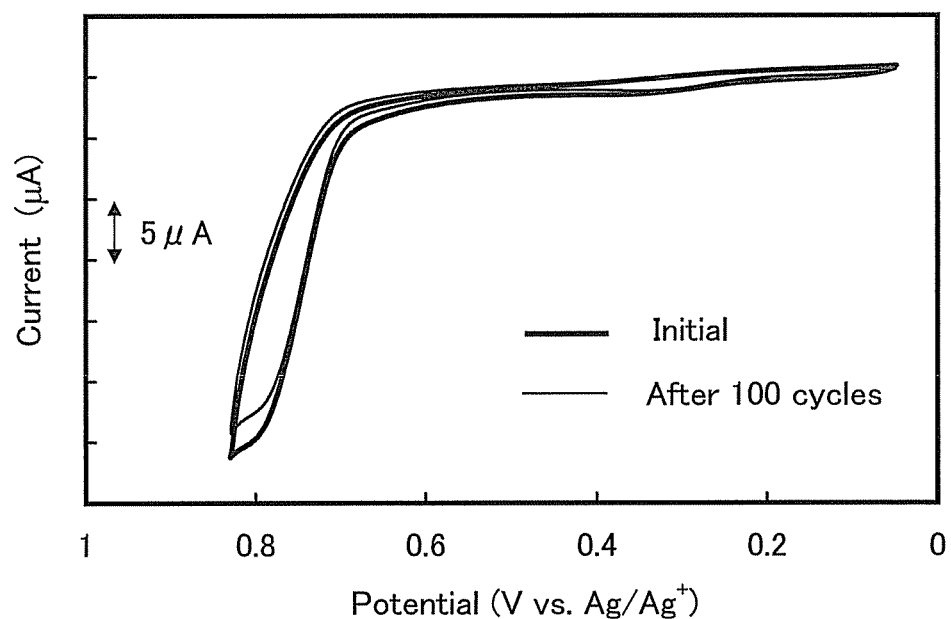
FIGS. 13A and 13B are CV charts of cgDBCzPA.

In the measurements of the oxidation characteristics, one cycle was scanning in which the potential of the working electrode with respect to the reference electrode was changed from 0.05 V to 0.83 V and then changed from 0.83 V to 0.05 V, and 100-cycle measurements were performed. Measurement results were shown in FIG. 13A.

The measurement results revealed that cgDBCzPA showed properties effective against repetition of redox reactions between an oxidized state and a neutral state without large variations in oxidation peak even after the 100-cycle measurements.

Figure 13B:
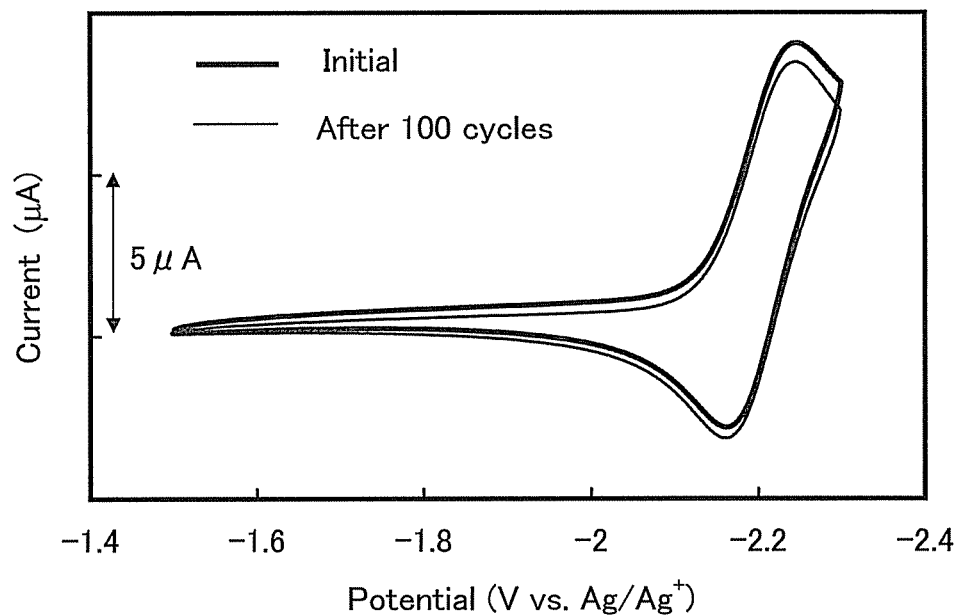

In the measurements of the reduction characteristics, one cycle was scanning in which the potential of the working electrode with respect to the reference electrode was changed from −1.50 V to −2.30 V and then changed from −2.30 V to −1.50 V, and 100-cycle measurements were performed. Measurement results were shown in FIG. 13B.

The measurement results revealed that cgDBCzPA showed properties effective against repetition of redox reactions between a reduced state and a neutral state without large variations in reduction peak even after the 100 cycles in the measurements.

Further, the HOMO and LUMO levels of cgDBCzPA were calculated also from the CV measurement results.

First, the potential energy of the reference electrode with respect to the vacuum level used was found to be −4.94 eV.

According to the measurement results of the oxidation characteristics of cgDBCzPA, the oxidation peak potential $E_{pa}$ was 0.81 V and the reduction peak potential $E_{pc}$ was 0.69 V. Therefore, a half-wave potential (an intermediate potential between $E_{pa}$ and $E_{pc}$) can be determined at 0.75 V. This means that cgDBCzPA is oxidized by an electric energy of 0.75 [V vs. Ag/Ag$^+$], and this energy corresponds to the HOMO level. Here, since the potential energy of the reference electrode, which was used in this example, with respect to the vacuum level is −4.94 [eV] as described above, the HOMO level of cgDBCzPA was found to be as follows: −4.94−0.75=−5.69 [eV]. According to the measurement results of the reduction characteristics of cgDBCzPA, the oxidation peak potential $E_{pc}$ was −2.25 V and the reduction peak potential $E_{pa}$ was −2.16 V. Therefore, a half-wave potential (an intermediate potential between $E_{pc}$ and $E_{pa}$) can be calculated at −2.21 V. This means that cgDBCzPA is reduced by an electric energy of −2.21 [V vs. Ag/Ag$^+$], and this energy corresponds to the LUMO level. Here, since the potential energy of the reference electrode, which was used in this example, with respect to the vacuum level is −4.94 [eV] as described above, the LUMO level of cgDBCzPA was found to be as follows: −4.94−(−2.21)=−2.74 [eV].

Note that the potential energy of the reference electrode (Ag/Ag$^+$ electrode) with respect to the vacuum level corresponds to the Fermi level of the Ag/Ag$^+$ electrode, and should be calculated from a value obtained by measuring a substance whose potential energy with respect to the vacuum level is known, with the use of the reference electrode (Ag/Ag$^+$ electrode).

How the potential energy (eV) of the reference electrode (Ag/Ag$^+$ electrode), which was used in this example, with respect to the vacuum level is determined by calculation is specifically described. It is known that the oxidation-reduction potential of ferrocene in methanol is +0.610 [V vs. SHE] with respect to the standard hydrogen electrode (Reference: Christian R. Goldsmith et al., *J. Am. Chem. Soc.*, Vol. 124, No. 1, pp. 83-96, 2002). In contrast, using the reference electrode used in this example, the oxidation-reduction potential of ferrocene in methanol was calculated at +0.11 V [vs. Ag/Ag$^+$]. Thus, it was found that the potential energy of this reference electrode was lower than that of the standard hydrogen electrode by 0.50 [eV].

Here, it is known that the potential energy of the standard hydrogen electrode with respect to the vacuum level is −4.44 eV (Reference: Toshihiro Ohnishi and Tamami Koyama, *High molecular EL material*, Kyoritsu shuppan, pp. 64-67). Therefore, the potential energy of the reference electrode used in this example with respect to the vacuum level can be calculated as follows: −4.44−0.50=−4.94 [eV].

Example 2

In this example is described a light-emitting element using a dibenzo[c,g]carbazole compound, 7-[4-(10-phenyl-9-anthryl)phenyl]-7H-dibenzo[c,g]carbazole (abbreviation: cgD-BCzPA, structural formula (100)), as a host material of a light-emitting layer using an emission center substance which emits blue fluorescence and as a material of an electron-transport layer, which is a light-emitting element described in Embodiment 1.

The molecular structures of organic compounds used in this example are illustrated in structural formulae (i) to (iv) and (100) below. The element structure was similar to that illustrated in FIG. 1A.

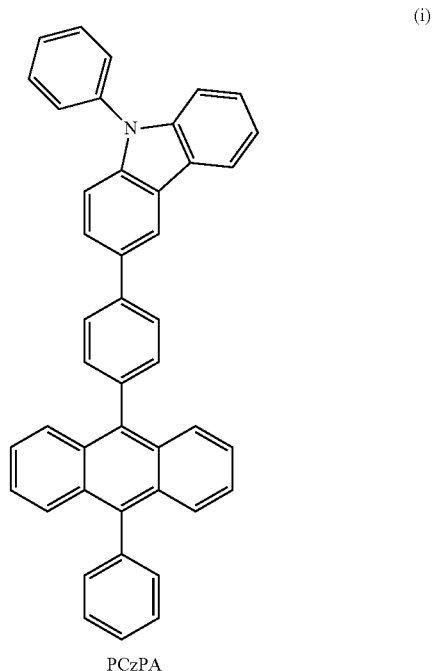

(i)

PCzPA

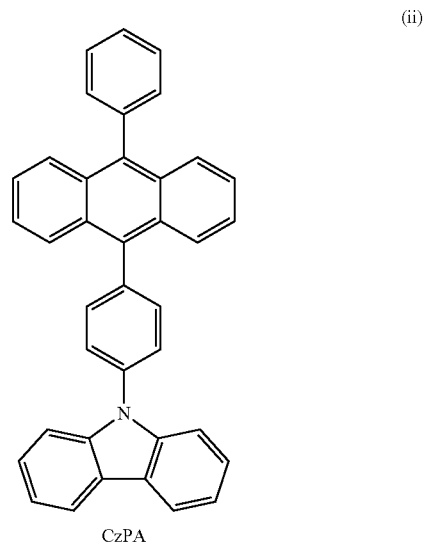 [SMILES: c1ccc(-c2c3ccccc3c(-c3ccc(-n4c5ccccc5c5ccccc54)cc3)c3ccccc23)cc1]

(ii)

CzPA

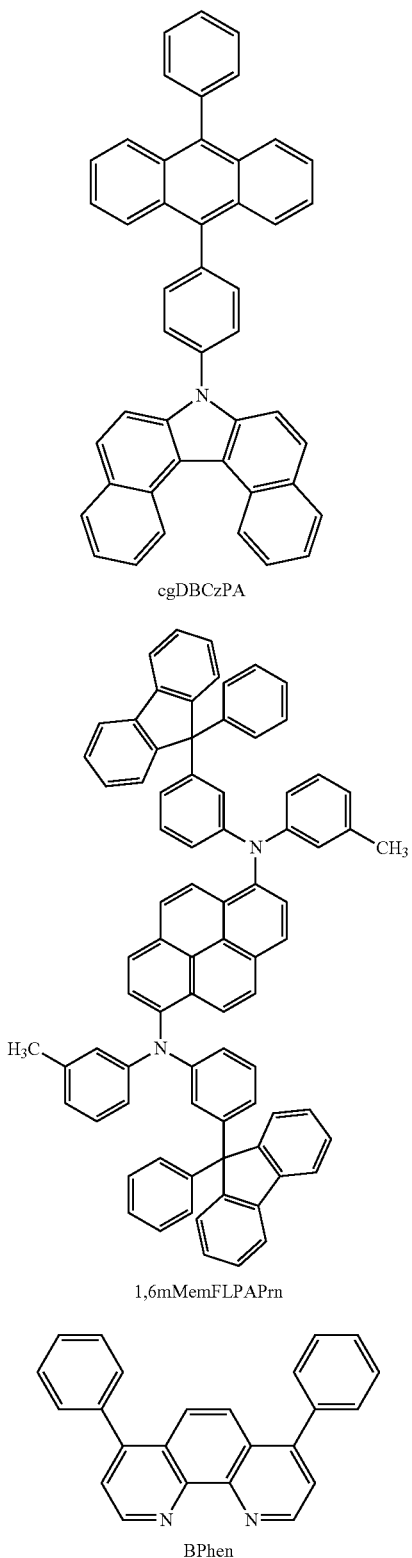

cgDBCzPA (iii)

1,6mMemFLPAPrn (iv)

BPhen

Fabrication of Light-Emitting Element 1

First, a glass substrate over which indium tin oxide containing silicon (ITSO) had been formed to a thickness of 110 nm was prepared as the first electrode 101. A surface of the ITSO was covered with a polyimide film so that an area of 2 mm×2 mm of the surface was exposed. The electrode area was 2 mm×2 mm. As pretreatment for forming the light-emitting element over this substrate, UV ozone treatment was performed for 370 seconds after washing of a surface of the substrate with water and baking that was performed at 200° C. for 1 hour. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate was fixed to a holder provided in the vacuum evaporation apparatus so that the surface of the substrate over which the ITSO film was formed faced downward.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) represented by the above structural formula (i) and molybdenum(VI)oxide were co-evaporated so that the ratio of PCzPA to molybdenum oxide was 2:1 (weight ratio), thereby forming the hole-injection layer 111. The thickness of the hole-injection layer 111 was set to 70 nm. Note that co-evaporation is an evaporation method in which a plurality of different substances is concurrently vaporized from the respective different evaporation sources.

Next, PCzPA was evaporated to a thickness of 30 nm, so that the hole-transport layer 112 was formed.

Further, over the hole-transport layer 112, 7-[4-(10-phenyl-9-anthryl)phenyl]-7H-dibenzo[c,g]carbazole (abbreviation: cgDBCzPA) represented by the above structural formula (100) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) were co-evaporated to a thickness of 25 nm so that the ratio of cgDBCzPA to 1,6mMemFLPAPrn was 1:0.03 (weight ratio), thereby forming the light-emitting layer 113.

Next, cgDBCzPA was evaporated to a thickness of 10 nm, and then bathophenanthroline (abbreviation: BPhen) represented by the above structural formula (iv) was evaporated to a thickness of 15 nm, thereby forming the electron-transport layer 114.

Further, lithium fluoride was evaporated to a thickness of 1 nm over the electron-transport layer 114, thereby forming the electron-injection layer. Lastly, aluminum was formed to a thickness of 200 nm as the second electrode 102 which serves as a cathode. Thus, the light-emitting element 1 was completed. Note that in all the above evaporation steps, evaporation was performed by a resistance-heating method.

Fabrication of Comparison Light-Emitting Element 1

The comparison light-emitting element 1 was formed like the light-emitting element 1, except for the light-emitting layer 113 and the electron-transport layer 114. As to the light-emitting layer 113, after the hole-transport layer 112 was formed, 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPAPm) represented by the above structural formula (iii) were co-evaporated to a thickness of 25 nm so that the ratio of CzPA to 1,6mMemFLPAPrn was 1:0.05 (weight ratio), thereby forming the light-emitting layer 113.

After the light-emitting layer 113 was formed, CzPA was evaporated to a thickness of 10 nm, and then bathophenanthroline (abbreviation: BPhen) represented by the above structural formula (iv) was evaporated to a thickness of 15 nm, thereby forming the electron-transport layer 114.

The structure other than the light-emitting layer 113 and the electron-transport layer 114 is similar to that of the light-emitting element 1, and repetition of the explanation of the structure is avoided. Refer to the fabrication method of the light-emitting element 1.

Thus, the comparison light-emitting element 1 was completed.

Operation Characteristics of Light-Emitting Element 1 and Comparison Light-Emitting Element 1

The light-emitting element 1 and the comparison light-emitting element 1 obtained as described above were sealed in a glove box containing a nitrogen atmosphere so as not to be exposed to the air (specifically, a sealing material was applied onto an outer edge of each element and heat treatment was performed at 80° C. for 1 hour at the time of sealing). Then, the operating characteristics of the light-emitting elements were measured. Note that the measurements were carried out at room temperature (in an atmosphere in which the temperature was kept at 25° C.).

Figure 14:
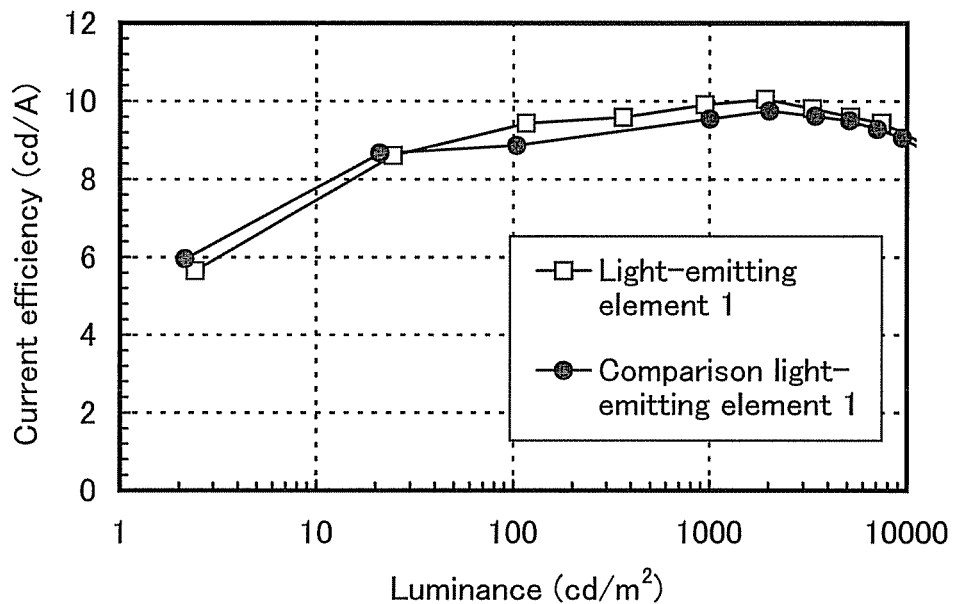
FIG. 14 shows luminance versus current efficiency characteristics of a light-emitting element 1 and a comparison light-emitting element 1.
Figure 15:
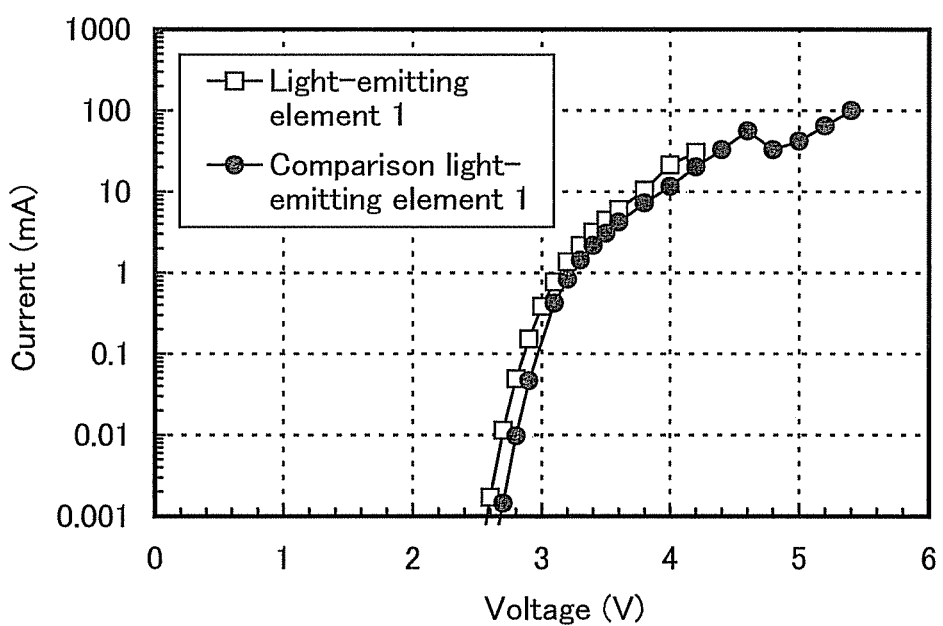
FIG. 15 shows voltage versus current characteristics of the light-emitting element 1 and the comparison light-emitting element 1.
Figure 16:
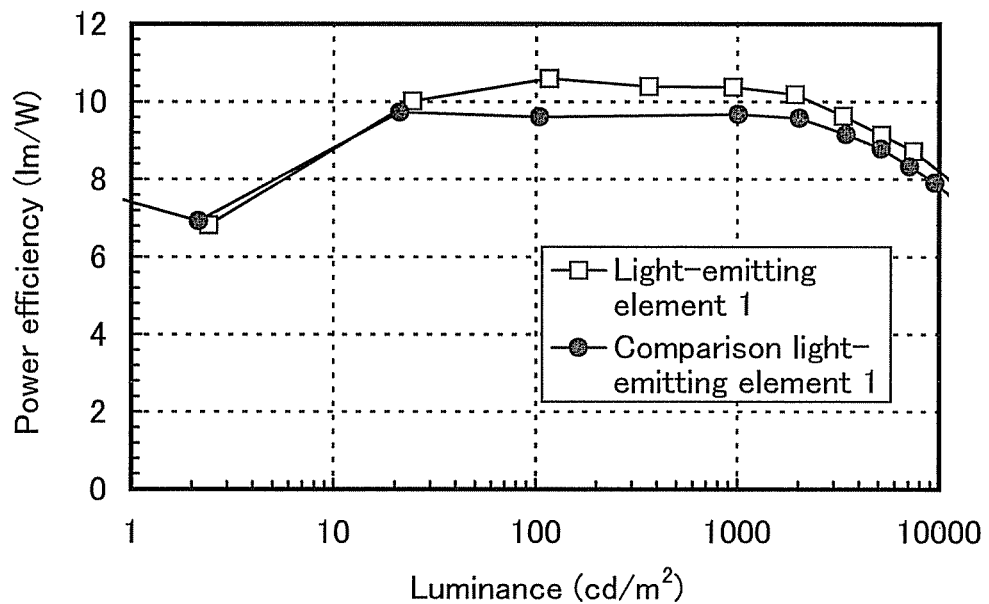
FIG. 16 shows luminance versus power efficiency characteristics of the light-emitting element 1 and the comparison light-emitting element 1.
Figure 17:
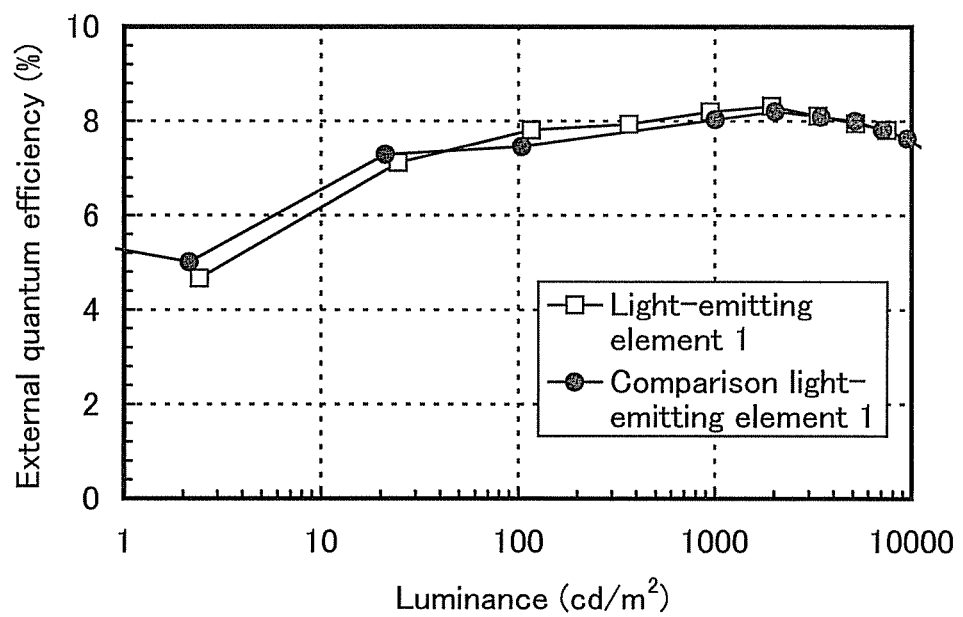
FIG. 17 shows luminance versus external quantum efficiency characteristics of the light-emitting element 1 and the comparison light-emitting element 1.

FIG. 14 shows luminance versus current efficiency characteristics of the light-emitting element 1 and the comparison light-emitting element 1, FIG. 15 shows voltage versus current characteristics, FIG. 16 shows luminance versus power efficiency characteristics, and FIG. 17 shows luminance versus external quantum efficiency characteristics. In FIG. 14, the vertical axis represents current efficiency (cd/A) and the horizontal axis represents luminance (cd/m$^2$). In FIG. 15, the vertical axis represents current (mA) and the horizontal axis represents voltage (V). In FIG. 16, the vertical axis represents power efficiency (lm/W) and the horizontal axis represents luminance (cd/m$^2$). In FIG. 17, the vertical axis represents external quantum efficiency (%) and the horizontal axis represents luminance (cd/m$^2$).

As can be seen from FIG. 14, the luminance versus current efficiency characteristics of the light-emitting element 1 that provides blue fluorescence and uses cgDBCzPA, which is a dibenzo[c,g]carbazole compound represented by the general formula (G1), as a host material of a light-emitting layer and as an electron-transport material of an electron-transport layer are favorable or substantially equal to the luminance versus current efficiency characteristics of the comparison light-emitting element 1 using CzPA like cgDBCzPA in the light-emitting element 1. This indicates that the light-emitting element 1 is a light-emitting element having high emission efficiency.

As can be seen from FIG. 15, the voltage versus current characteristics of the light-emitting element 1 are favorable or substantially equal to those of the comparison light-emitting element 1, which indicates that the light-emitting element 1 is a light-emitting element having low driving voltage. This means that the dibenzo[c,g]carbazole compound represented by the general formula (G1) has an excellent carrier-transport property.

As can be seen from FIG. 16, the light-emitting element 1 exhibits better luminance versus power efficiency characteristics than the light-emitting element 1, which indicates that the light-emitting element 1 is a light-emitting element having low power consumption. Thus, the light-emitting element 1 using cgDBCzPA, which is a dibenzo[c,g]carbazole compound represented by the general formula (G1), is a light-emitting element having favorable characteristics such as low driving voltage and high emission efficiency.

As can be seen from FIG. 17, the luminance versus external quantum efficiency characteristics of the light-emitting element 1 are favorable and substantially equal to those of the comparison light-emitting element 1, which indicates that the light-emitting element 1 is a light-emitting element having high emission efficiency.

Figure 18:
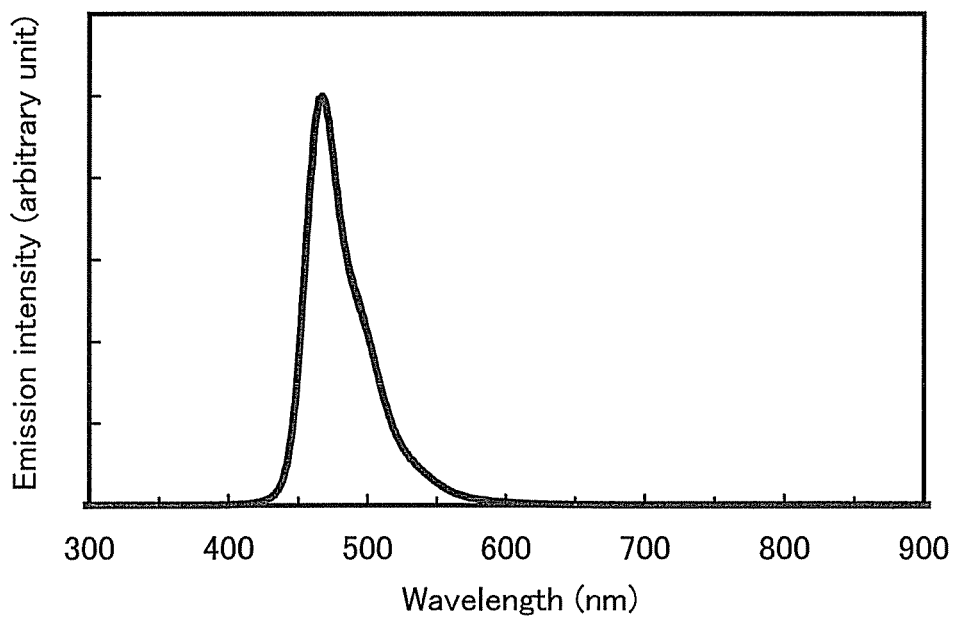
FIG. 18 shows emission spectra of the light-emitting element 1 and the comparison light-emitting element 1.

FIG. 18 shows emission spectra obtained when a current of 0.1 mA was made to flow in the fabricated light-emitting element 1 and the comparison light-emitting element 1. In FIG. 18, the vertical axis represents emission intensity (arbitrary unit) and the horizontal axis represents wavelength (nm). The emission intensity is shown as a value relative to the maximum emission intensity assumed to be 1. FIG. 18 indicates that both the light-emitting element 1 and the comparison light-emitting element 1 emit blue light emission derived from 1,6mMemFLPAPrn, which was the emission center substance.

Figure 19:
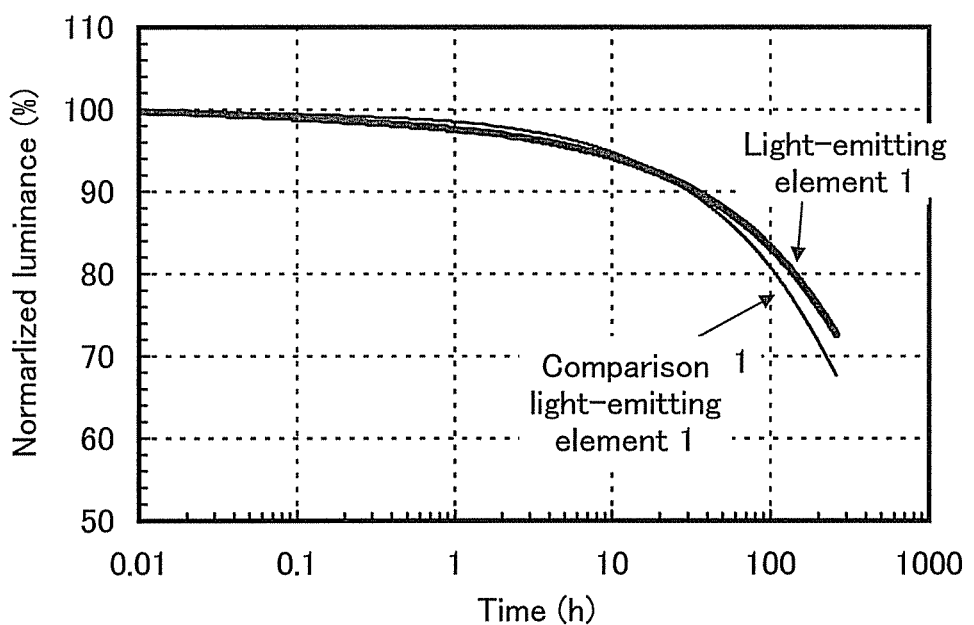
FIG. 19 shows normalized luminance versus time characteristics of the light-emitting element 1 and the comparison light-emitting element 1.

Next, with an initial luminance set to 5000 cd/m$^2$, the light-emitting element 1 and the comparison light-emitting element 1 were driven under a condition where the current density was constant, and changes in luminance relative to driving time were examined. FIG. 19 shows normalized luminance versus time characteristics. FIG. 19 indicates that, although the comparison light-emitting element 1 using CzPA is a light-emitting element having a long lifetime, the light-emitting element 1 using cgDBCzPA is an extremely reliable element having a longer lifetime than the comparison light-emitting element 1.

As compared with CzPA, cgDBCzPA is highly stable to evaporation and can easily provide a light-emitting element having stable qualities.

As described above, cgDBCzPA is found to be a material with which a light-emitting element having the right combination of excellent characteristics can be provided.

Example 3

In this example is described a light-emitting element using a dibenzo[c,g]carbazole compound, 7-[4-(10-phenyl-9-anthryl)phenyl]-7H-dibenzo[c,g]carbazole (abbreviation: cgDBCzPA, structural formula (100)), as a host material of a light-emitting layer using an emission center substance which emits blue fluorescence and as a material of an electron-transport layer, which is a light-emitting element described in Embodiment 1.

The molecular structures of organic compounds used in this example are illustrated in structural formulae (i) to (v) and (100) below. The element structure was similar to that illustrated in FIG. 1A.

(i)
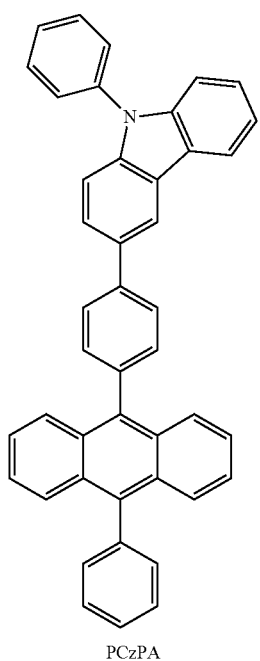
PCzPA
(ii)
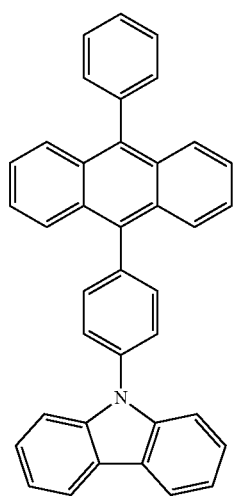
CzPA
(v)
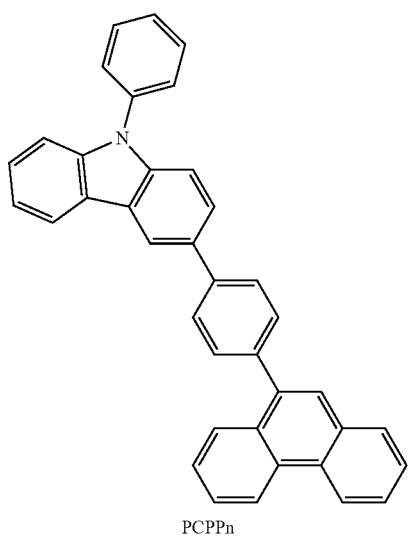
PCPPn
(100)
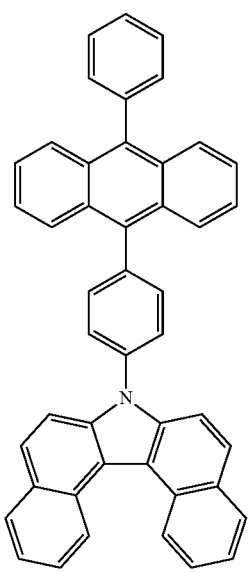
cgDBCzPA

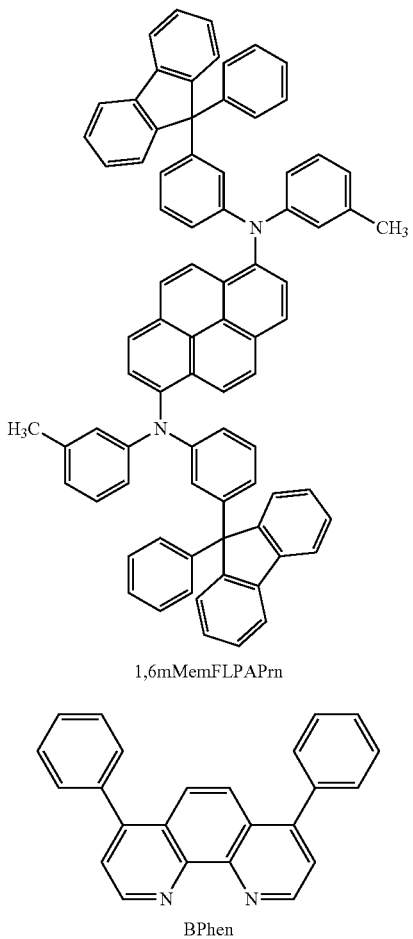

1,6mMemFLPAPrn

BPhen

Fabrication of Light-Emitting Element 2

First, a glass substrate over which indium tin oxide containing silicon (ITSO) had been formed to a thickness of 110 nm was prepared as the first electrode 101. A surface of the ITSO was covered with a polyimide film so that an area of 2 mm×2 mm of the surface was exposed. The electrode area was 2 mm×2 mm. As pretreatment for forming the light-emitting element over this substrate, UV ozone treatment was performed for 370 seconds after washing of a surface of the substrate with water and baking that was performed at 200° C. for 1 hour. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate was fixed to a holder provided in the vacuum evaporation apparatus so that the surface of the substrate over which the ITSO film was formed faced downward.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) represented by the above structural formula (i) and molybdenum(VI)oxide were co-evaporated so that the ratio of PCzPA to molybdenum oxide was 2:1 (weight ratio), thereby forming the hole-injection layer 111. The thickness of the hole-injection layer 111 was set to 70 nm. Note that co-evaporation is an evaporation method in which a plurality of different substances is concurrently vaporized from the respective different evaporation sources.

Next, 3-[4-(9-phenanthryl)-phenyl]-9-phenyl-9H-carbazole (abbreviation: PCPPn) represented by the above structural formula (v) was evaporated to a thickness of 30 nm, so that the hole-transport layer 112 was formed.

Further, over the hole-transport layer 112, 7-[4-(10-phenyl-9-anthryl)phenyl]-7H-dibenzo[c,g]carbazole (abbreviation: cgDBCzPA) represented by the above structural formula (100) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) were co-evaporated to a thickness of 25 nm so that the ratio of cgDBCzPA to 1,6mMemFLPAPrn was 1:0.03 (weight ratio), thereby forming the light-emitting layer 113.

Next, cgDBCzPA was evaporated to a thickness of 10 nm, and then bathophenanthroline (abbreviation: BPhen) represented by the above structural formula (iv) was evaporated to a thickness of 15 nm, thereby forming the electron-transport layer 114.

Further, lithium fluoride was evaporated to a thickness of 1 nm over the electron-transport layer 114, thereby forming the electron-injection layer. Lastly, aluminum was formed to a thickness of 200 nm as the second electrode 102 which serves as a cathode. Thus, the light-emitting element 2 was completed. Note that in all the above evaporation steps, evaporation was performed by a resistance-heating method.

Fabrication of Comparison Light-Emitting Element 2

The comparison light-emitting element 2 was formed like the light-emitting element 2, except for the light-emitting layer 113 and the electron-transport layer 114. As to the light-emitting layer 113, after the hole-transport layer 112 was formed, 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) were co-evaporated to a thickness of 25 nm so that the ratio of CzPA to 1,6mMemFLPAPrn was 1:0.05 (weight ratio), thereby forming the light-emitting layer 113.

After the light-emitting layer 113 was formed, CzPA was evaporated to a thickness of 10 nm, and then bathophenanthroline (abbreviation: BPhen) represented by the above structural formula (iv) was evaporated to a thickness of 15 nm, thereby forming the electron-transport layer 114.

The structure other than the light-emitting layer 113 and the electron-transport layer 114 is similar to that of the light-emitting element 2, and repetition of the explanation of the structure is avoided. Refer to the fabrication method of the light-emitting element 2.

Thus, the comparison light-emitting element 2 was completed.

Operation Characteristics of Light-Emitting Element 2 and Comparison Light-Emitting Element 2

The light-emitting element 2 and the comparison light-emitting element 2 obtained as described above were sealed in a glove box containing a nitrogen atmosphere so as not to be exposed to the air (specifically, a sealing material was applied onto an outer edge of each element and heat treatment was performed at 80° C. for 1 hour at the time of sealing). Then, the operating characteristics of the light-emitting elements were measured. Note that the measurements were carried out at room temperature (in an atmosphere in which the temperature was kept at 25° C.).

Figure 20:
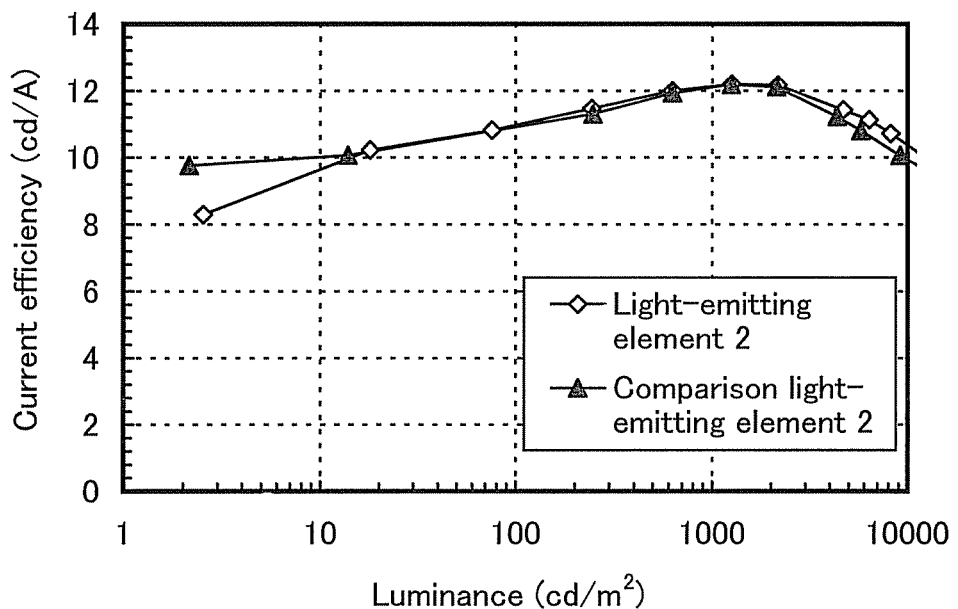
FIG. 20 shows luminance versus current efficiency characteristics of a light-emitting element 2 and a comparison light-emitting element 2.
Figure 21:
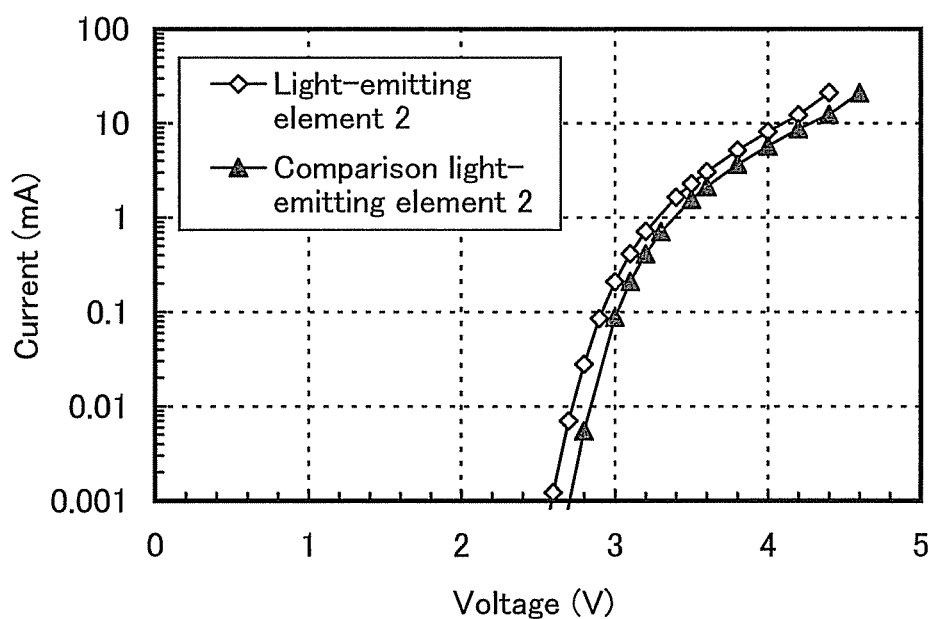
FIG. 21 shows voltage versus current characteristics of the light-emitting element 2 and the comparison light-emitting element 2.
Figure 22:
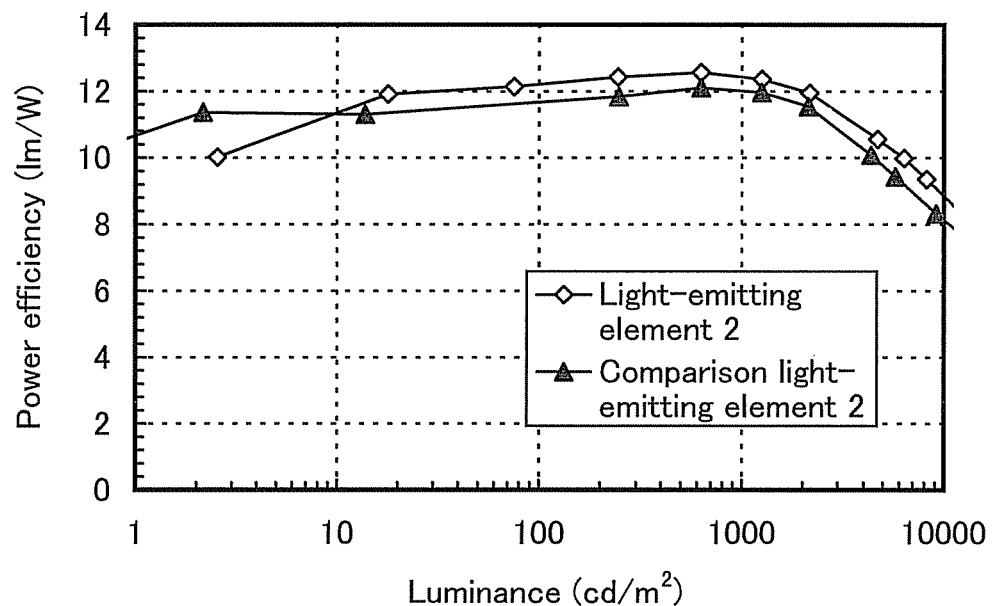
FIG. 22 shows luminance versus power efficiency characteristics of the light-emitting element 2 and the comparison light-emitting element 2.
Figure 23:
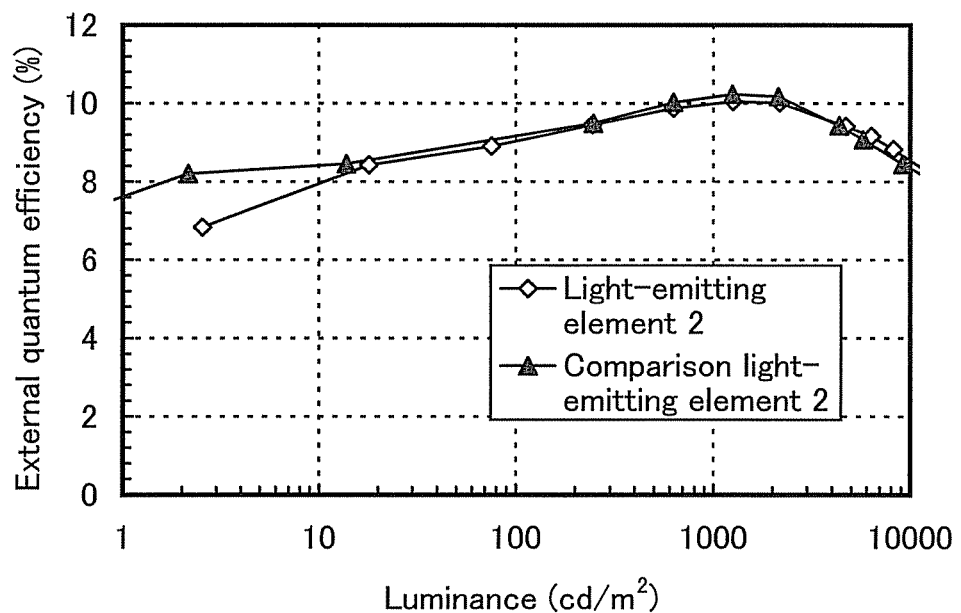
FIG. 23 shows luminance versus external quantum efficiency characteristics of the light-emitting element 2 and the comparison light-emitting element 2.

FIG. 20 shows luminance versus current efficiency characteristics of the light-emitting element 2 and the comparison light-emitting element 2, FIG. 21 shows voltage versus current characteristics, FIG. 22 shows luminance versus power efficiency characteristics, and FIG. 23 shows luminance versus external quantum efficiency characteristics. In FIG. 20, the vertical axis represents current efficiency (cd/A) and the horizontal axis represents luminance (cd/m$^2$). In FIG. 21, the vertical axis represents current (mA) and the horizontal axis represents voltage (V). In FIG. 22, the vertical axis represents power efficiency (lm/W) and the horizontal axis represents luminance (cd/m$^2$). In FIG. 23, the vertical axis represents external quantum efficiency (%) and the horizontal axis represents luminance (cd/m$^2$).

As can be seen from FIG. 20, the luminance versus current efficiency characteristics of the light-emitting element 2 that provides blue fluorescence and uses cgDBCzPA, which is a dibenzo[c,g]carbazole compound represented by the general formula (G1), as a host material of a light-emitting layer and as an electron-transport material of an electron-transport layer are substantially equal to the luminance versus current efficiency characteristics of the comparison light-emitting element 2 using CzPA like cgDBCzPA in the light-emitting element 2. This indicates that the light-emitting element 2 is a light-emitting element having high emission efficiency.

As can be seen from FIG. 21, the light-emitting element 2 exhibits better voltage versus current characteristics than the light-emitting element 2, which indicates that the light-emitting element 2 is a light-emitting element having low driving voltage. This means that the dibenzo[c,g]carbazole compound represented by the general formula (G1) has an excellent carrier-transport property.

As can be seen from FIG. 22, the light-emitting element 2 exhibits very favorable luminance versus power efficiency characteristics better than those of the comparison light-emitting element 2, which indicates that the light-emitting element 2 is a light-emitting element having low power consumption. Thus, the light-emitting element 2 using cgDBCzPA which is a dibenzo[c,g]carbazole compound represented by the general formula (G1) is a light-emitting element having favorable characteristics such as low driving voltage and high emission efficiency.

As can be seen from FIG. 23, the luminance versus external quantum efficiency characteristics of the light-emitting element 2 are favorable and substantially equal to those of the comparison light-emitting element 2, which indicates that the light-emitting element 2 is a light-emitting element having very high emission efficiency.

Figure 24:
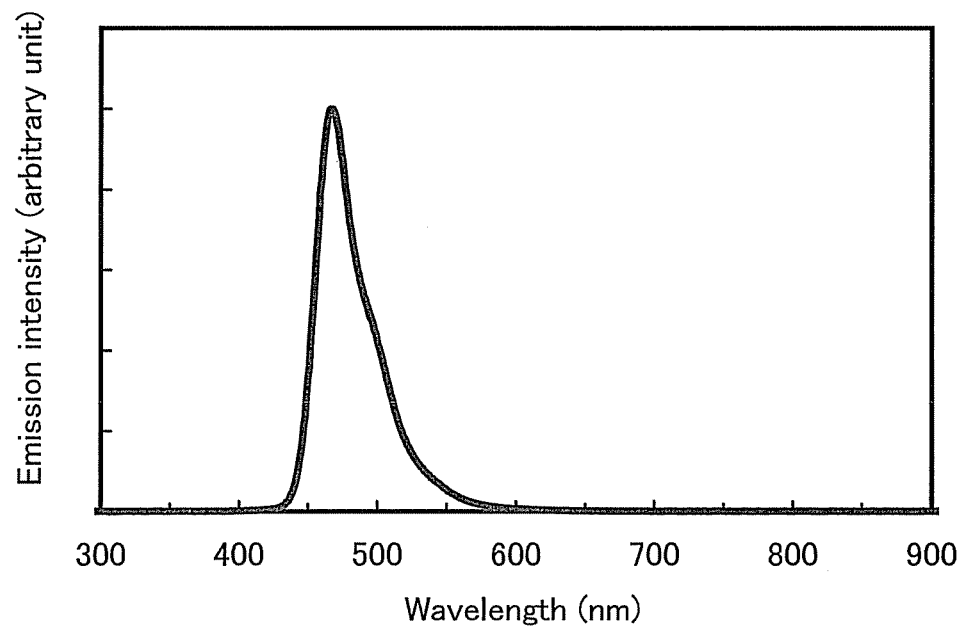
FIG. 24 shows emission spectra of the light-emitting element 2 and the comparison light-emitting element 2.

FIG. 24 shows emission spectra obtained when a current of 0.1 mA was made to flow in the fabricated light-emitting element 2 and the comparison light-emitting element 2. In FIG. 24, the vertical axis represents emission intensity (arbitrary unit) and the horizontal axis represents wavelength (nm). The emission intensity is shown as a value relative to the maximum emission intensity assumed to be 1. FIG. 24 shows the spectra of the light-emitting element 2 and the comparison light-emitting element 2 overlaps completely, which indicates that both elements emit blue light emission derived from 1,6mMemFLPAPrn, which was the emission center substance.

Figure 25:
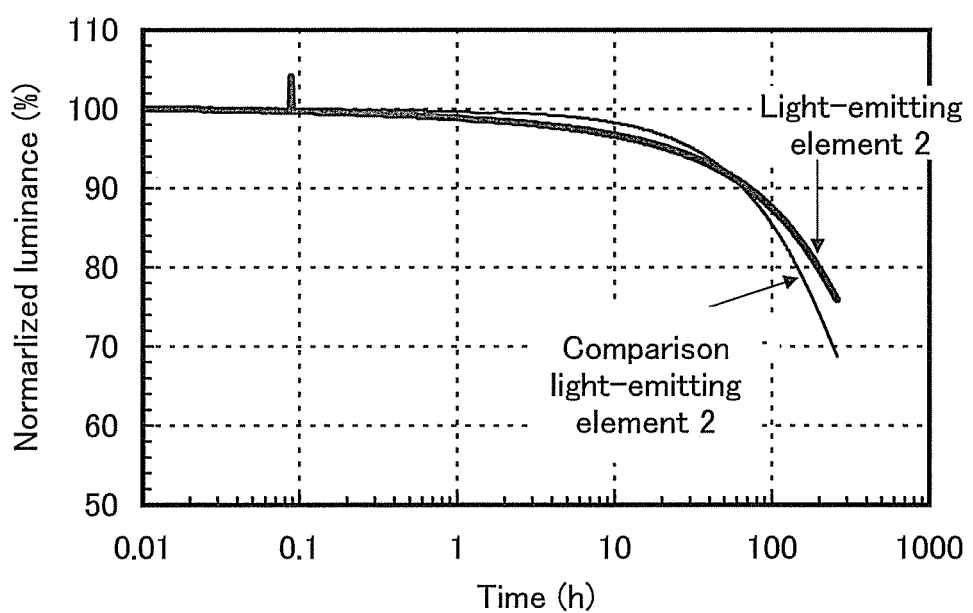
FIG. 25 shows normalized luminance versus time characteristics of a light-emitting element 2 and a comparison light-emitting element 2.

Next, with an initial luminance set to 5000 cd/m$^2$, the light-emitting element 2 and the comparison light-emitting element 2 were driven under a condition where the current density was constant, and changes in luminance relative to driving time were examined. FIG. 25 shows normalized luminance versus time characteristics. FIG. 25 indicates that, although the comparison light-emitting element 2 using CzPA is a light-emitting element having a long lifetime, the light-emitting element 2 using cgDBCzPA is an extremely reliable element having a longer lifetime than the comparison light-emitting element 2.

As compared with CzPA, cgDBCzPA is highly stable to evaporation and can easily provide a light-emitting element having stable qualities.

As described above, it is also confirmed in this example that cgDBCzPA is found to be a material with which a light-emitting element having the right combination of excellent characteristics can be provided.

Example 4

In this example is described a light-emitting element using a dibenzo[c,g]carbazole compound, 7-[4-(10-phenyl-9-anthryl)phenyl]-7H-dibenzo[c,g]carbazole (abbreviation: cgDBCzPA, structural formula (100)), as a host material of a light-emitting layer using an emission center substance which emits blue fluorescence and as a material of an electron-transport layer, which is a light-emitting element described in Embodiment 1.

The molecular structures of organic compounds used in this example are illustrated in structural formulae (i) to (vi) and (100) below. The element structure was similar to that illustrated in FIG. 1A.

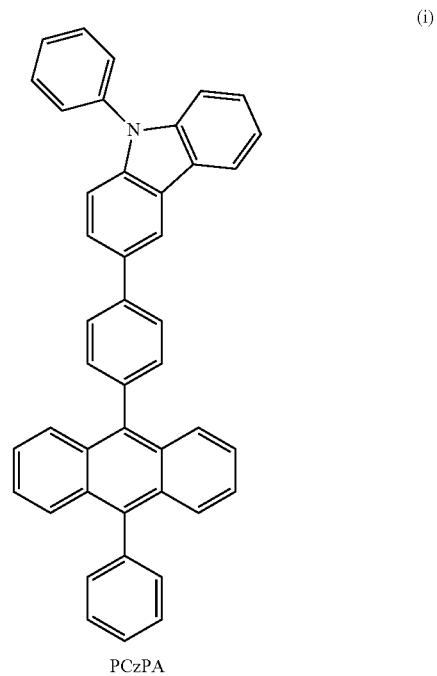

(i)

PCzPA

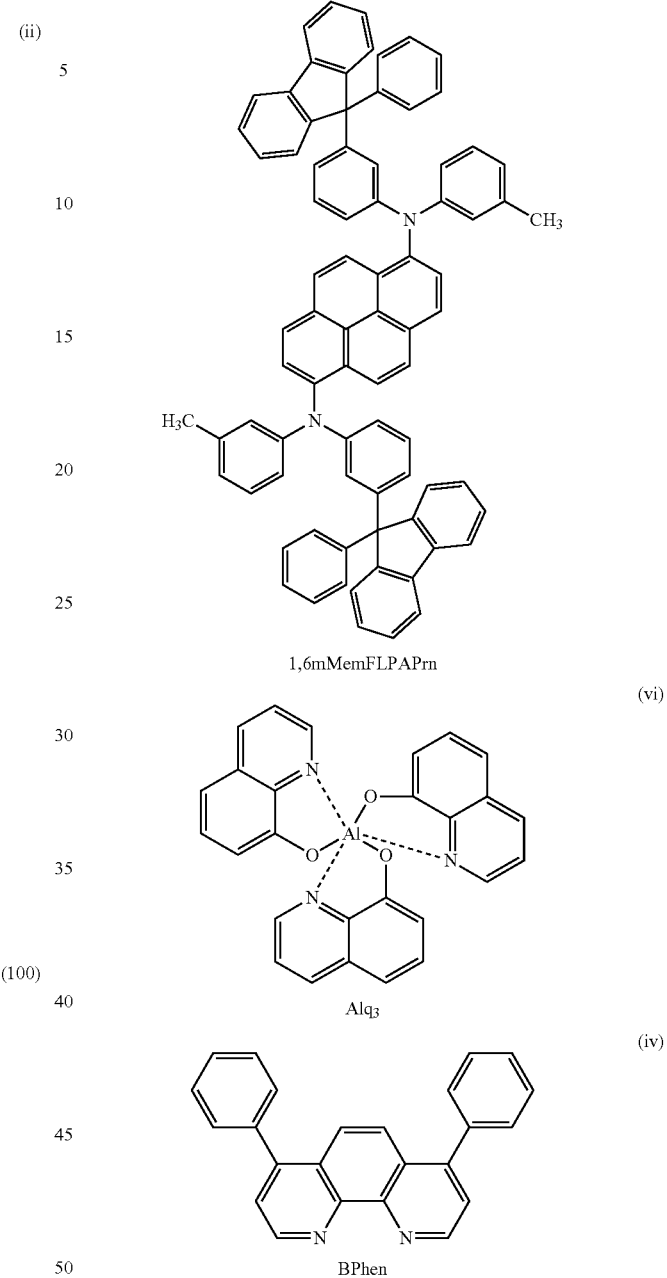

Fabrication of Light-Emitting Element 3

First, a glass substrate over which indium tin oxide containing silicon (ITSO) had been formed to a thickness of 110 nm was prepared as the first electrode 101. A surface of the ITSO was covered with a polyimide film so that an area of 2 mm×2 mm of the surface was exposed. The electrode area was 2 min×2 mm. As pretreatment for forming the light-emitting element over this substrate, UV ozone treatment was performed for 370 seconds after washing of a surface of the substrate with water and baking that was performed at 200° C. for 1 hour. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate was fixed to a holder provided in the vacuum evaporation apparatus so that the surface of the substrate over which the ITSO film was formed faced downward.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) represented by the above structural formula (i) and molybdenum(VI)oxide were co-evaporated so that the ratio of PCzPA to molybdenum oxide was 2:1 (weight ratio), thereby forming the hole-injection layer 111. The thickness of the hole-injection layer 111 was set to 50 nm. Note that co-evaporation is an evaporation method in which a plurality of different substances is concurrently vaporized from the respective different evaporation sources.

Next, PCzPA was evaporated to a thickness of 10 nm, so that the hole-transport layer 112 was formed.

Further, over the hole-transport layer 112, 7-[4-(10-phenyl-9-anthryl)phenyl]-7H-dibenzo[c,g]carbazole (abbreviation: cgDBCzPA) represented by the above structural formula (100) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) were co-evaporated to a thickness of 30 nm so that the ratio of cgDBCzPA to 1,6mMemFLPAPrn was 1:0.05 (weight ratio), thereby forming the light-emitting layer 113.

Next, tris(8-quinolinolato)aluminum(III) (abbreviation: Alq) represented by the above structural formula (vi) was evaporated to a thickness of 10 nm, and then bathophenanthroline (abbreviation: BPhen) represented by the above structural formula (iv) was evaporated to a thickness of 15 nm; thereby forming the electron-transport layer 114.

Further, lithium fluoride was evaporated to a thickness of 1 nm over the electron-transport layer 114, thereby forming the electron-injection layer. Lastly, aluminum was formed to a thickness of 200 nm as the second electrode 102 which serves as a cathode. Thus, the light-emitting element 3 was completed. Note that in all the above evaporation steps, evaporation was performed by a resistance-heating method.

Fabrication of Comparison Light-Emitting Element 3

The comparison light-emitting element 3 was formed like the light-emitting element 3, except for the light-emitting layer 113. For the comparison light-emitting element 3, after the hole-transport layer 112 was formed, 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) were co-evaporated to a thickness of 30 nm so that the ratio of CzPA to 1,6mMemFLPAPrn was 1:0.05 (weight ratio), thereby forming the light-emitting layer 113.

The structure other than the light-emitting layer 113 is similar to that of the light-emitting element 3, and repetition of the explanation of the structure is avoided. Refer to the fabrication method of the light-emitting element 3.

Thus, the comparison light-emitting element 3 was completed.

Operation Characteristics of Light-Emitting Element 3 and Comparison Light-Emitting Element 3

The light-emitting element 3 and the comparison light-emitting element 3 obtained as described above were sealed in a glove box containing a nitrogen atmosphere so as not to be exposed to the air (specifically, a sealing material was applied onto an outer edge of each element and heat treatment was performed at 80° C. for 1 hour at the time of sealing). Then, the operating characteristics of the light-emitting elements were measured. Note that the measurements were carried out at room temperature (in an atmosphere in which the temperature was kept at 25° C.).

Figure 26:
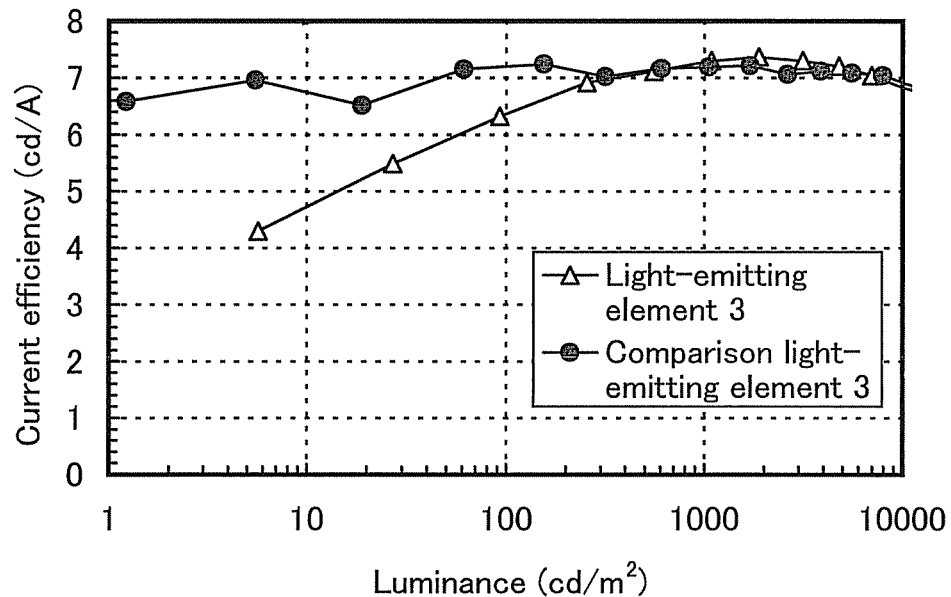
FIG. 26 shows luminance versus current efficiency characteristics of the light-emitting element 3 and the comparison light-emitting element 3.
Figure 27:
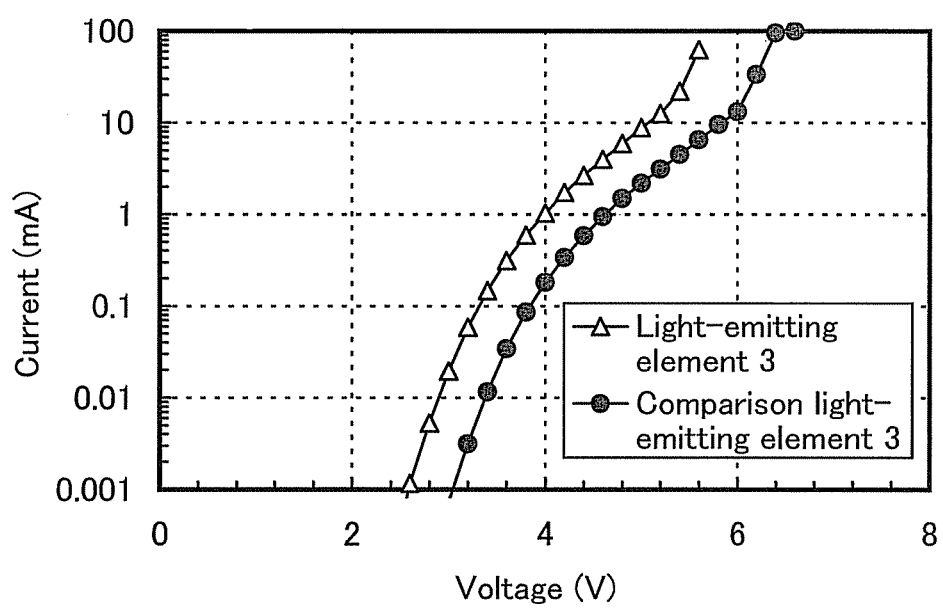
FIG. 27 shows voltage versus current characteristics of the light-emitting element 3 and the comparison light-emitting element 3.

FIG. 26 shows luminance versus current efficiency characteristics of the light-emitting element 3 and the comparison light-emitting element 3, and FIG. 27 shows voltage versus current characteristics. In FIG. 26, the vertical axis represents current efficiency (cd/A) and the horizontal axis represents luminance (cd/m$^2$). In FIG. 27, the vertical axis represents current (mA) and the horizontal axis represents voltage (V).

As can be seen from FIG. 26, the luminance versus current efficiency characteristics of the light-emitting element 3 that provides blue fluorescence and uses cgDBCzPA, which is a dibenzo[c,g]carbazole compound represented by the general formula (G1), as a host material of a light-emitting layer and as an electron-transport material of an electron-transport layer are equal to the luminance versus current efficiency characteristics of the comparison light-emitting element 3 using CzPA like cgDBCzPA in the light-emitting element 3. This indicates that the light-emitting element 3 is a light-emitting element having high emission efficiency.

As can be seen from FIG. 27, the light-emitting element 3 has much better voltage versus current characteristics than the comparison light-emitting element 3, which indicates that the light-emitting element 3 is a light-emitting element having low driving voltage. This means that the dibenzo[c,g]carbazole compound represented by the general formula (G1) has an excellent carrier-transport property.

Figure 28:
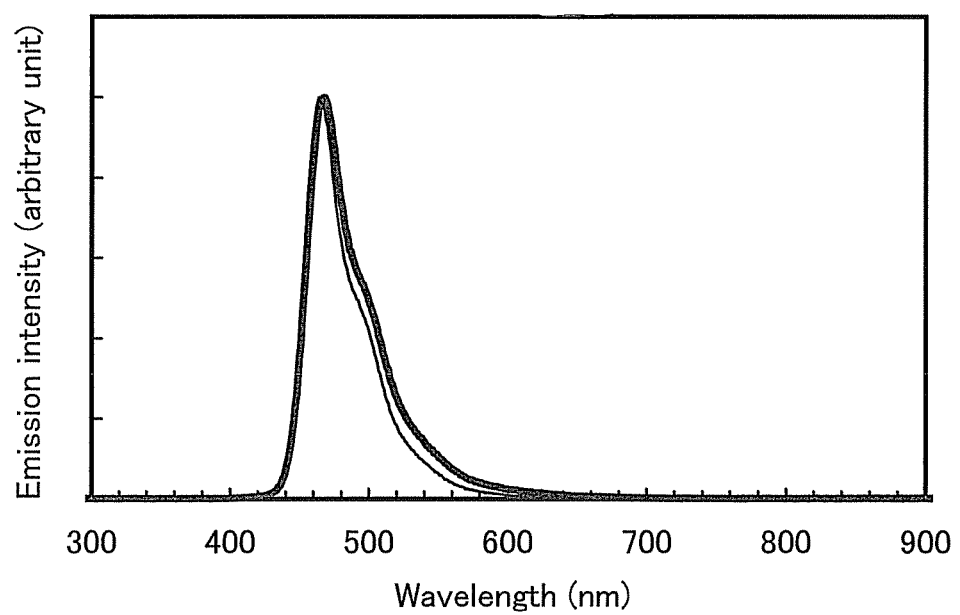
FIG. 28 shows emission spectra of the light-emitting element 3 and the comparison light-emitting element 3.

FIG. 28 shows emission spectra obtained when a current of 0.1 mA was made to flow in the fabricated light-emitting element 3 and the comparison light-emitting element 3. In FIG. 28, the vertical axis represents emission intensity (arbitrary unit) and the horizontal axis represents wavelength (nm). The emission intensity is shown as a value relative to the maximum emission intensity assumed to be 1. FIG. 28 shows the spectra of the light-emitting element 3 and the comparison light-emitting element 3 are not greatly different, which indicates that both elements emit blue light emission derived from 1,6mMemFLPAPrn, which was the emission center substance.

As compared with CzPA, cgDBCzPA is highly stable to evaporation and can easily provide a light-emitting element having stable qualities.

As described above, it is also confirmed in this example that cgDBCzPA is found to be a material with which a light-emitting element having the right combination of excellent characteristics can be provided.

Example 5

In this example is described a light-emitting element using a dibenzo[c,g]carbazole compound, 7-[4-(10-phenyl-9-anthryl)phenyl]-7H-dibenzo[c,g]carbazole (abbreviation: cgDBCzPA, structural formula (100)), as a host material of a light-emitting layer using an emission center substance which emits blue fluorescence and as a material of an electron-transport layer, which is a light-emitting element described in Embodiment 1.

The molecular structures of organic compounds used in this example are illustrated in structural formulae (i), (iii), (iv), (vi) to (viii), and (100) below. The element structure was similar to that illustrated in FIG. 1A.

(i)
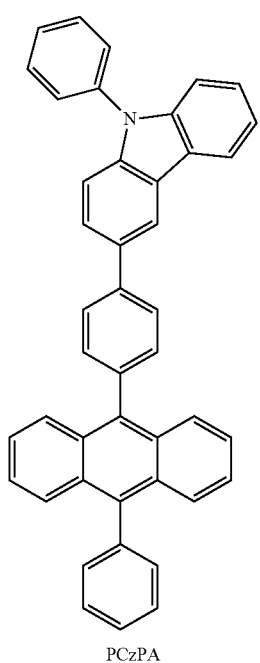
PCzPA
(100)
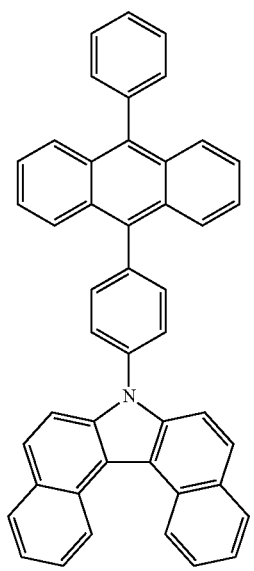
cgDBCzPA
(vii)
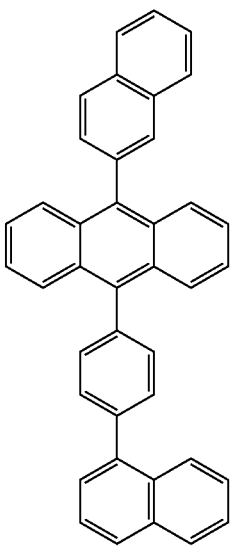
(viii)
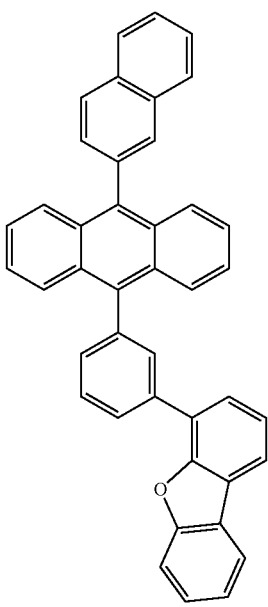

-continued (iii)

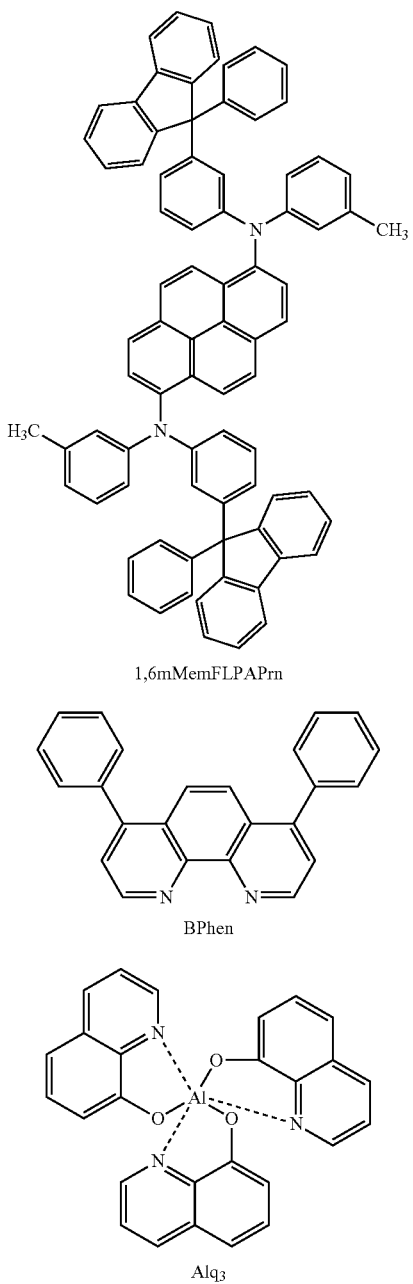

1,6mMemFLPAPrn (iv)

BPhen (vi)

Alq₃

Fabrication of Light-Emitting Element 4

First, a glass substrate over which indium tin oxide containing silicon (ITSO) had been formed to a thickness of 110 nm was prepared as the first electrode 101. A surface of the ITSO was covered with a polyimide film so that an area of 2 mm×2 mm of the surface was exposed. The electrode area was 2 mm×2 mm. As pretreatment for forming the light-emitting element over this substrate, UV ozone treatment was performed for 370 seconds after washing of a surface of the substrate with water and baking that was performed at 200° C. for 1 hour. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate was fixed to a holder provided in the vacuum evaporation apparatus so that the surface of the substrate over which the ITSO film was formed faced downward.

After the pressure in the vacuum evaporation apparatus was reduced to $10^{-4}$ Pa, 9-phenyl-3-[4-(10-phenyl-9-anthryl) phenyl]-9H-carbazole (abbreviation: PCzPA) represented by the above structural formula (i) and molybdenum(VI)oxide were co-evaporated so that the ratio of PCzPA to molybdenum oxide was 2:1 (weight ratio), thereby forming the hole-injection layer 111. The thickness of the hole-injection layer 111 was set to 50 nm. Note that co-evaporation is an evaporation method in which a plurality of different substances is concurrently vaporized from the respective different evaporation sources.

Next, PCzPA was evaporated to a thickness of 10 nm, so that the hole-transport layer 112 was formed.

Further, over the hole-transport layer 112, 7-[4-(10-phenyl-9-anthryl)phenyl]-7H-dibenzo[c,g]carbazole (abbreviation: cgDBCzPA) represented by the above structural formula (100) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) were co-evaporated to a thickness of 25 nm so that the ratio of cgDBCzPA to 1,6mMemFLPAPrn was 1:0.03 (weight ratio), thereby forming the light-emitting layer 113.

Next, tris(8-quinolinolato)aluminum(III) (abbreviation: Alq) represented by the above structural formula (vi) was evaporated to a thickness of 10 nm, and then bathophenanthroline (abbreviation: BPhen) represented by the above structural formula (iv) was evaporated to a thickness of 15 nm, thereby forming the electron-transport layer 114.

Further, lithium fluoride was evaporated to a thickness of 1 nm over the electron-transport layer 114, thereby forming the electron-injection layer. Lastly, aluminum was formed to a thickness of 200 nm as the second electrode 102 which serves as a cathode. Thus, the light-emitting element 4 was completed. Note that in all the above evaporation steps, evaporation was performed by a resistance-heating method.

Fabrication of Comparison Light-Emitting Element 4-1

The comparison light-emitting element 4-1 was formed like the light-emitting element 4, except for the light-emitting layer 113. For the comparison light-emitting element 4-1, after the hole-transport layer 112 was formed, a known anthracene derivative represented by the above structural formula (vii) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) were co-evaporated to a thickness of 25 nm so that the ratio of the anthracene derivative to 1,6mMemFLPAPrn was 1:0.03 (weight ratio), thereby forming the light-emitting layer 113.

The structure other than the light-emitting layer 113 is similar to that of the light-emitting element 4, and repetition of the explanation of the structure is avoided. Refer to the fabrication method of the light-emitting element 4.

Thus, the comparison light-emitting element 4-1 was completed.

Fabrication of Comparison Light-Emitting Element 4-2

The comparison light-emitting element 4-2 was formed like the light-emitting element 4, except for the light-emitting layer 113. For the comparison light-emitting element 4-2, after the hole-transport layer 112 was formed, a known anthracene derivative represented by the above structural formula (viii) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) were co-evaporated to a thickness of 25 nm so that the ratio of the anthracene derivative to 1,6mMemFLPAPrn was 1:0.03 (weight ratio), thereby forming the light-emitting layer 113.

The structure other than the light-emitting layer 113 is similar to that of the light-emitting element 4, and repetition of the explanation of the structure is avoided. Refer to the fabrication method of the light-emitting element 4.

Thus, the comparison light-emitting element 4-2 was completed.

Operation Characteristics of Light-Emitting Element 4 and Comparison Light-Emitting Elements 4-1 and 4-2

The light-emitting element 4 and the comparison light-emitting elements 4-1 and 4-2 obtained as described above were sealed in a glove box containing a nitrogen atmosphere so as not to be exposed to the air (specifically, a sealing material was applied onto an outer edge of each element and heat treatment was performed at 80° C. for 1 hour at the time of sealing). Then, the operating characteristics of the light-emitting elements were measured. Note that the measurements were carried out at room temperature (in an atmosphere in which the temperature was kept at 25° C.).

Figure 29:
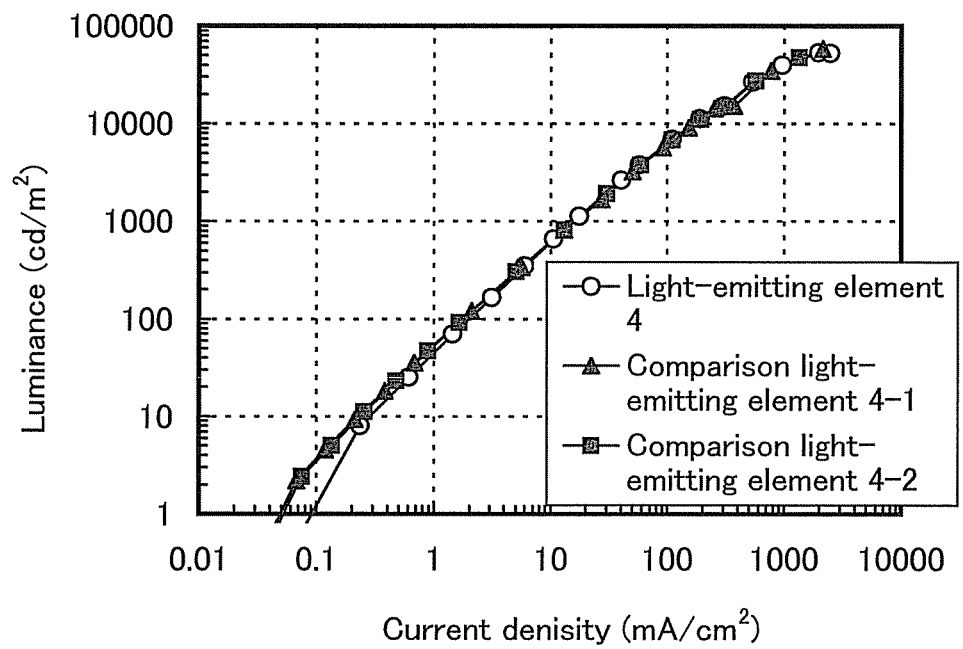
FIG. 29 shows current density versus luminance characteristics of a light-emitting element 4 and comparison light-emitting elements 4-1 and 4-2.
Figure 30:
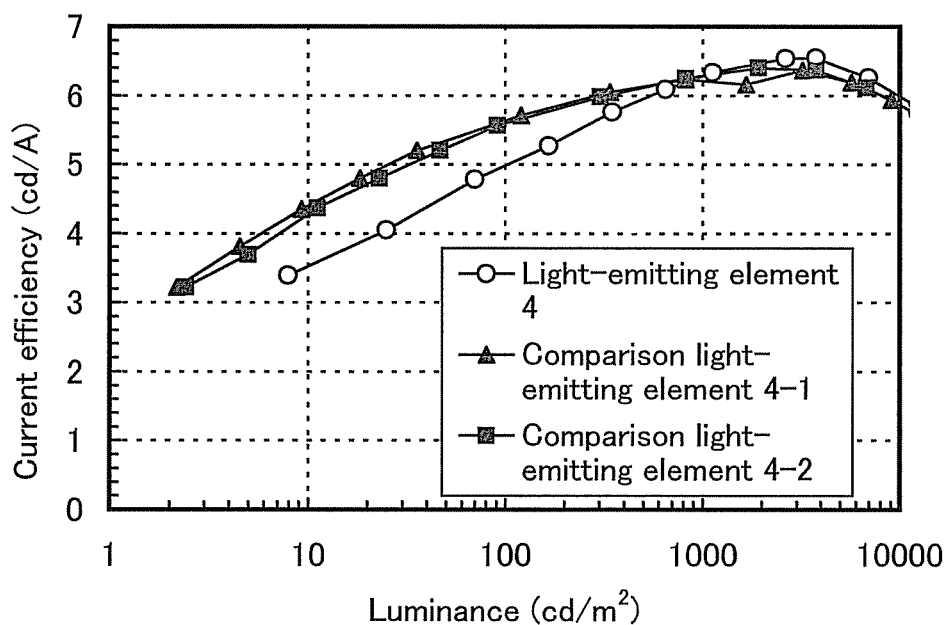
FIG. 30 shows luminance versus current efficiency characteristics of the light-emitting element 4 and the comparison light-emitting elements 4-1 and 4-2.
Figure 31:
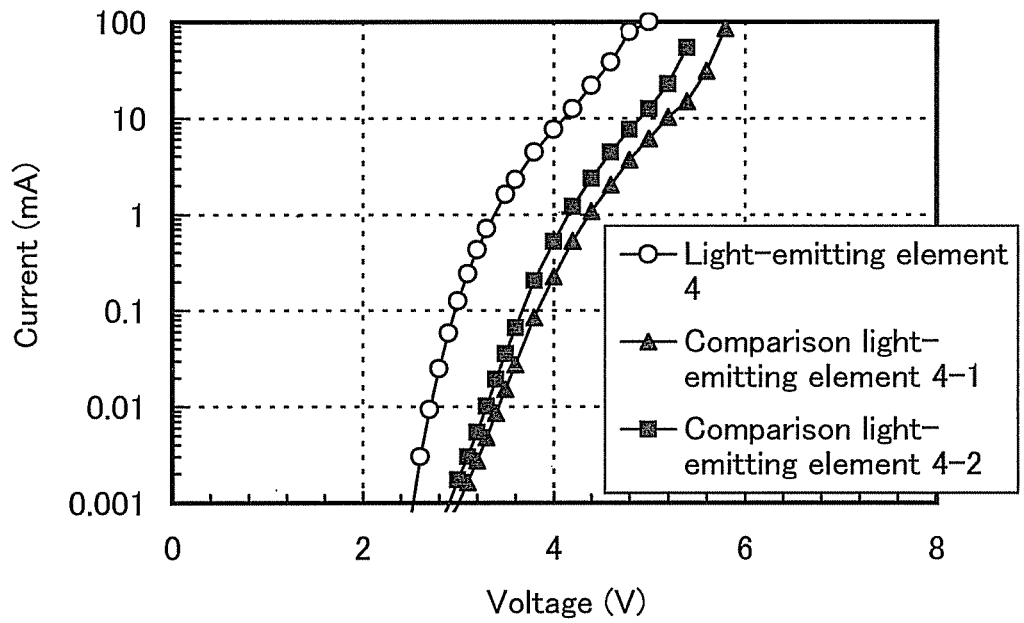
FIG. 31 shows voltage versus current characteristics of the light-emitting element 4 and the comparison light-emitting elements 4-1 and 4-2.
Figure 32:
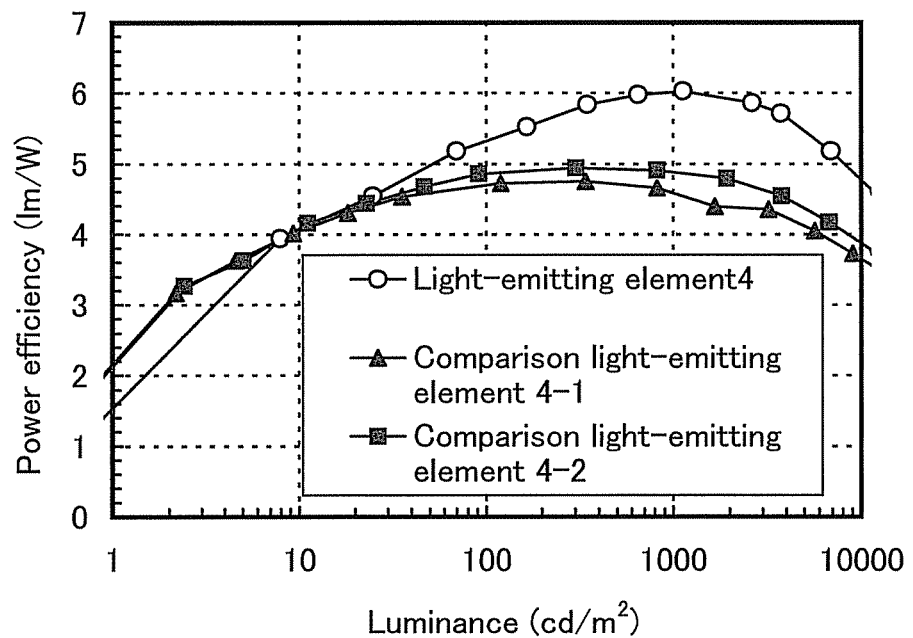
FIG. 32 shows luminance versus power efficiency characteristics of the light-emitting element 4 and the comparison light-emitting elements 4-1 and 4-2.
Figure 33:
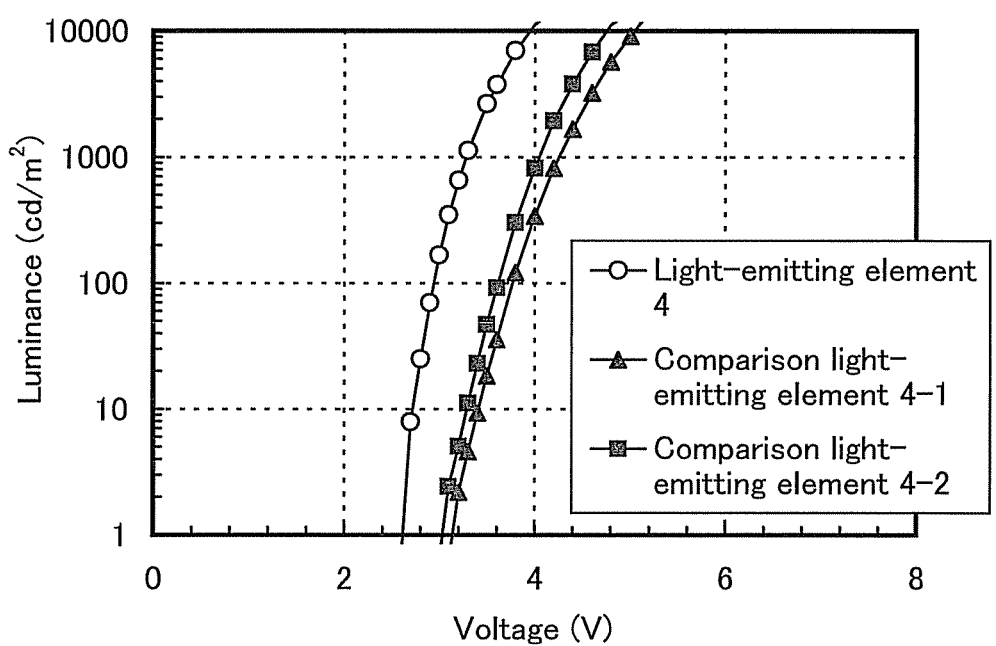
FIG. 33 shows voltage versus luminance characteristics of the light-emitting element 4 and the comparison light-emitting elements 4-1 and 4-2.

FIG. 29 shows current density versus luminance characteristics of the light-emitting element 4 and the comparison light-emitting elements 4-1 and 4-2, FIG. 30 shows luminance versus current efficiency characteristics, FIG. 31 shows voltage versus current characteristics, FIG. 32 shows luminance versus power efficiency characteristics, and FIG. 33 shows voltage versus luminance characteristics. In FIG. 29, the vertical axis represents luminance ($cd/m^2$) and the horizontal axis represents current density ($mA/cm^2$). In FIG. 30, the vertical axis represents current efficiency (cd/A) and the horizontal axis represents luminance ($cd/m^2$). In FIG. 31, the vertical axis represents current (mA) and the horizontal axis represents voltage (V). In FIG. 32, the vertical axis represents power efficiency (lm/W) and the horizontal axis represents luminance ($cd/m^2$). In FIG. 33, the vertical axis represents luminance ($cd/m^2$) and the horizontal axis represents voltage (V).

As can be seen from FIG. 29, the light-emitting element 4 and the comparison light-emitting elements 4-1 and 4-2 have substantially equal current density versus luminance characteristics. In addition, FIG. 30 reveals that the light-emitting element 4 and the comparison light-emitting elements 4-1 and 4-2 have substantially equal luminance versus current efficiency characteristics, at a luminance of at least 1000 $cd/m^2$ or more which is a practical luminance.

Furthermore, FIG. 31 reveals that the light-emitting element 4 exhibits much better voltage versus current characteristics than the comparison light-emitting elements 4-1 and 4-2. This indicates the favorable carrier-transport property of cgDBCzPA. Thus, also as seen from FIG. 32, the light-emitting element 4 is found to be an element having highly favorable luminance versus power efficiency characteristics. Note that FIG. 33 shows high driving voltage of the comparison light-emitting elements 4-1 and 4-2, and in order to achieve a luminance of 1000 $cd/m^2$, which is of practical use, a voltage of about 3.3 V needs to be applied to the light-emitting element 4 but a voltage of 4 V or more needs to be applied to each of the comparison light-emitting elements 4-1 and 4-2. The driving voltage of the comparison light-emitting element 4-1 is especially high.

Figure 34:
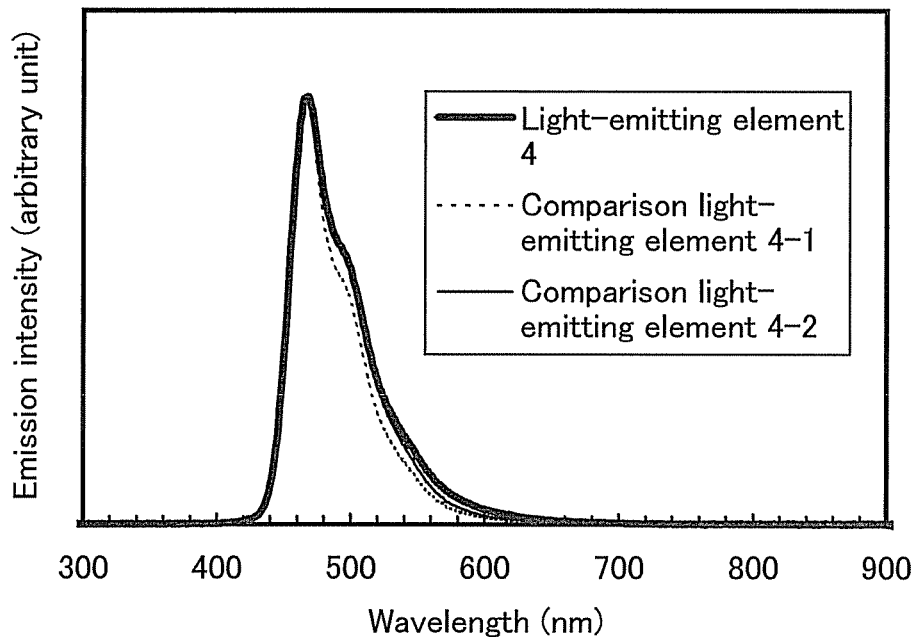
FIG. 34 shows emission spectra of the light-emitting element 4 and the comparison light-emitting elements 4-1 and 4-2.

FIG. 34 shows emission spectra obtained when a current of 0.1 mA was made to flow in the fabricated light-emitting element 4 and the comparison light-emitting element 4-1 and 4-2. In FIG. 34, the vertical axis represents emission intensity (arbitrary unit) and the horizontal axis represents wavelength (nm). The emission intensity is shown as a value relative to the maximum emission intensity assumed to be 1. FIG. 34 shows the spectra of the light-emitting element 4 and the comparison light-emitting element 4-1 and 4-2 are not greatly different, which indicates that both elements emit blue light emission derived from 1,6mMemFLPAPrn, which was the emission center substance.

Figure 35:
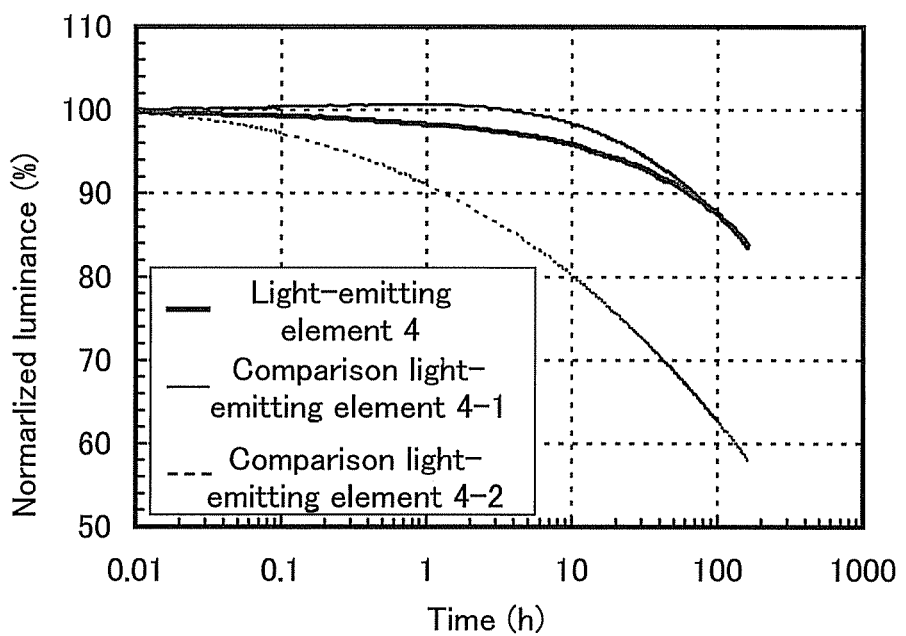
FIG. 35 shows normalized luminance versus time characteristics of the light-emitting element 4 and the comparison light-emitting elements 4-1 and 4-2.

Next, with an initial luminance set to 5000 $cd/m^2$, the light-emitting element 4 and the comparison light-emitting elements 4-1 and 4-2 were driven under a condition where the current density was constant, and changes in luminance relative to driving time were examined. FIG. 35 shows normalized luminance versus time characteristics. FIG. 35 shows that the comparison light-emitting element 4-2 using the substance represented by the above structural formula (viii) has a shorter lifetime than the other elements. In addition, although the comparison light-emitting element 4-1 using the substance represented by the above structural formula (vii) instead of cgDBCzPA has a lifetime equal to that of the light-emitting element 4 at a glance, the comparison light-emitting element 4-1 exhibits not only a rise in initial luminance but also an increase in deterioration rate after a certain time point; consequently, the half life of the comparison light-emitting element 4-1 is estimated at about half of that of the light-emitting element 4.

Thus, the comparison light-emitting element 4-1 has a drawback in driving voltage and the comparison light-emitting element 4-2 has drawbacks in both driving voltage and lifetime, and it is difficult for each element to have the right combination of characteristics. In contrast, by using cgDBCzPA, a high-performance light-emitting element which has excellent combination of characteristics in terms of efficiency, driving voltage, and lifetime is found to be able to be fabricated. What is remarkable is the driving voltage, which enables a light-emitting element having very high power efficiency to be provided.

As described above, it is also confirmed in this example that cgDBCzPA is found to be a material with which a light-emitting element having the right combination of excellent characteristics can be provided.

Example 6

In this example is described a synthesis method of 7-[4-(10-phenyl-9-anthryl)phenyl]-7H-dibenzo[c,g]carbazole (abbreviation: cgDBCzPA), which is a dibenzo[c,g]carbazole compound represented by the general formula (G1) described in Embodiment 2, which is different from the synthesis method in Example 1.

The steps up to and including synthesis of 7H-dibenzo[c,g]carbazole were the same as Steps 1 and 2 in Example 1.

Step 3:
7-(4-Bromophenyl)-7H-dibenzo[c,g]carbazole

In a 200 mL three-neck flask were placed 5.0 g (18 mmol) of 7H-dibenzo[c,g]carbazole, 13 g (47 mol) of 4-bromoiodobenzene, and 1.9 g (20 mmol) of sodium tert-butoxide. After the air in the flask was replaced with nitrogen, to this mixture were added 100 mL of mesitylene and 0.90 mL of tri-(tert-butyl)phosphine (a 10 wt % hexane solution). This mixture was degassed by being stirred while the pressure was reduced. After the degassing, 0.51 g (0.90 mmol) of bis(dibenzylideneacetone)palladium(0) was added to this mixture. This mixture was stirred at 170° C. for 17 hours under a nitrogen stream. After the stirring, 20 mL of water was added to the obtained mixture. The aqueous layer of this mixture was extracted with toluene, and the solution of the extract and the organic layer were combined and washed with saturated brine. The organic layer was dried with magnesium sulfate, and this mixture was gravity-filtered. A solid obtained by concentration of the obtained filtrate was dissolved in about 30 mL of toluene. This solution was suction-filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). A solid obtained by concentration of the filtrate was recrystallized from toluene/hexane to give 2.9 g of pale yellow needle-like crystals, which was the object of the synthesis, in a yield of 38% yield. A reaction scheme (c-2) of Step 3 is illustrated below.

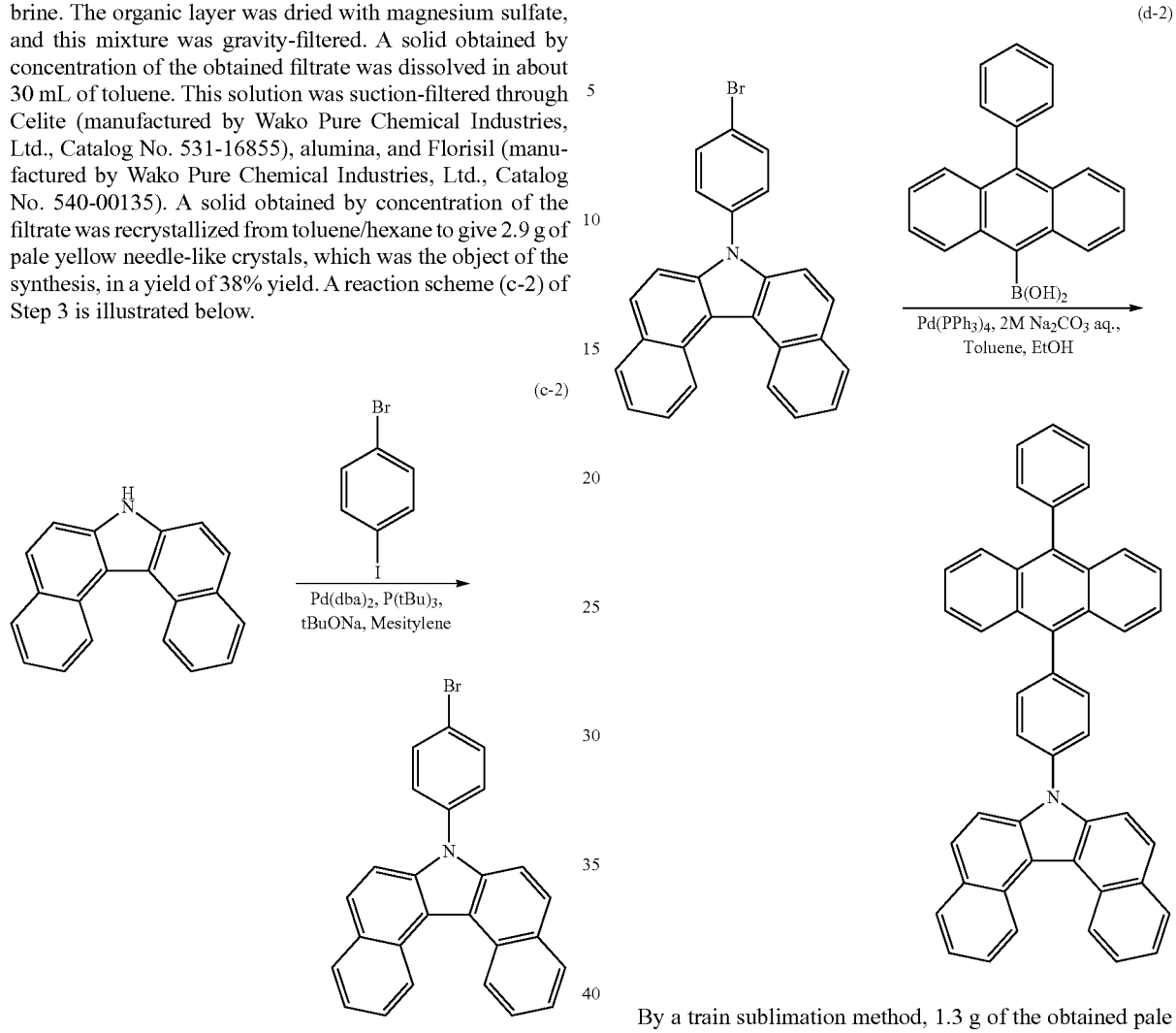

Step 4: 7-[4-(10-Phenyl-9-anthryl)phenyl]-7H-dibenzo[c,g]carbazole (cgDBCzPA)

In a 200 mL three-neck flask were placed 1.7 g (4.0 mmol) of 7-(4-bromophenyl)-7H-dibenzo[c,g]carbazole and 1.2 g (4.0 mmol) of 10-phenylanthracene-9-boronic acid, and the air in the flask was replaced with nitrogen. To this mixture were added 15 mL of toluene, 5.0 mL of ethanol, and 4.0 mL of an aqueous solution of sodium carbonate. This mixture was degassed by being stirred while the pressure was reduced. To this mixture was added 0.23 g (0.20 mmol) of tetrakis(triphenylphosphine)palladium(0), and the mixture was stirred at 90° C. for 10 hours under a nitrogen stream, so that a solid was precipitated. The precipitated solid was removed by suction filtration. The collected solid was dissolved in about 50 mL of hot toluene, and this solution was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). A solid obtained by concentration of the filtrate was washed with toluene/hexane to give 1.3 g of a pale yellow powder, which was the object of the synthesis, in a yield of 55%. A synthesis scheme (d-2) of Step 4 is illustrated below.

By a train sublimation method, 1.3 g of the obtained pale yellow powdery solid was purified by sublimation. In the sublimation purification, cgDBCzPA was heated at 300° C. under a pressure of 3.6 Pa with a flow rate of argon at 5.0 mL/min. After the sublimation purification, 1.1 g of a pale yellow solid of cgDBCzPA was recovered in 86% yield.

Reference Example 1

A method of synthesizing N,N'-bis(3-methylphenyl)-N,N'-bis[3-(9-phenyl-9H-fluoren-9-yl)phenyl]-pyrene-1,6-diamine (abbreviation: 1,6mMemFLPAPrn) used in the above examples is described.

Step 1: Synthesis of 3-Methylphenyl-3-(9-phenyl-9H-fluoren-9-yl)phenylamine (abbreviation: mMemFLPA)

There were placed 3.2 g (8.1 mmol) of 9-(3-bromophenyl)-9-phenylfluorene and 2.3 g (24.1 mmol) of sodium tert-butoxide in a 200 mL three-neck flask. The air in the flask was replaced with nitrogen. Then, 40.0 mL of toluene, 0.9 mL (8.3 mmol) of m-toluidine, and 0.2 mL of a 10% hexane solution of tri(tert-butyl)phosphine were added to this mixture. The temperature of this mixture was set to 60° C., and 44.5 mg (0.1 mmol) of bis(dibenzylideneacetone)palladium(0) was added to the mixture. The temperature of the mixture was raised to 80° C., and the mixture was stirred for 2.0 hours. After the stirring, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (developing solvent: hexane/toluene in a 1:1 ratio). Recrystallization from a mixed solvent of toluene and hexane gave 2.8 g of a white solid, which was the object of the synthesis, in 82% yield. A synthesis scheme of the above Step 1 is illustrated below.

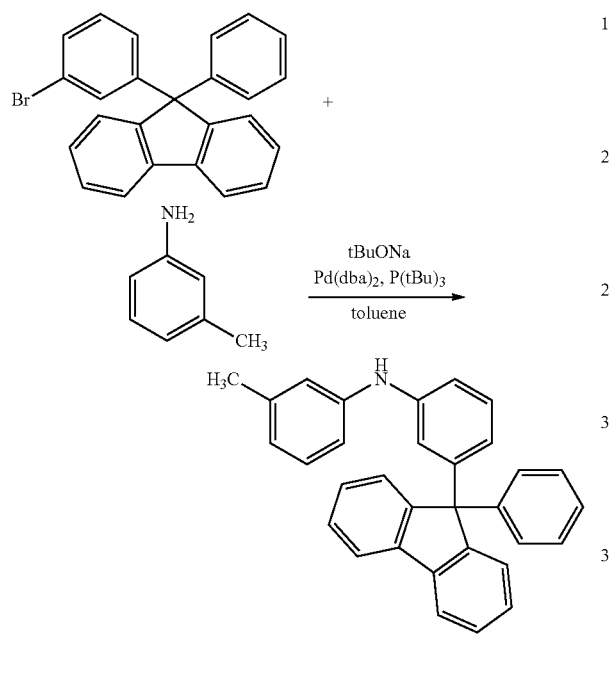

Step 2: Synthesis of N,N'-Bis(3-methylphenyl)-N,N'-bis[3-(9-phenyl-9H-fluoren-9-yl)phenyl]-pyrene-1,6-diamine (abbreviation: 1,6mMemFLPAPrn)

There were placed 0.6 g (1.7 mmol) of 1,6-dibromopyrene, 1.4 g (3.4 mmol) of 3-methylphenyl-3-(9-phenyl-9H-fluoren-9-yl)phenylamine obtained in Step 1 above, and 0.5 g (5.1 mmol) of sodium tert-butoxide in a 100 mL three-neck flask. The air in the flask was replaced with nitrogen. To this mixture were added 21.0 mL of toluene and 0.2 mL of a 10% hexane solution of tri(tert-butyl)phosphine. The temperature of this mixture was set to 60° C., and 34.9 mg (0.1 mmol) of bis(dibenzylideneacetone)palladium(0) was added to the mixture. The temperature of this mixture was set to 80° C., and the mixture was stirred for 3.0 hours. After the stirring, 400 mL of toluene was added to the mixture, and the mixture was heated. While the mixture it was suction-filtered through Florisil (produced by Wako Pure Chemical Industries, was kept hot, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (developing solvent: hexane/toluene in a 3:2 ratio) to give a yellow solid. Recrystallization of the obtained yellow solid from a mixed solvent of toluene and hexane gave 1.2 g of a yellow solid, which was the object of the synthesis, in 67% yield.

By a train sublimation method, 1.0 g of the obtained yellow solid was purified. In the purification, the yellow solid was heated at 317° C. under a pressure of 2.2 Pa with a flow rate of argon gas of 5.0 mL/min. After the purification, 1.0 g of a yellow solid, which was the object of the synthesis, in 93% yield. A synthesis scheme of the above Step 2 is illustrated below.

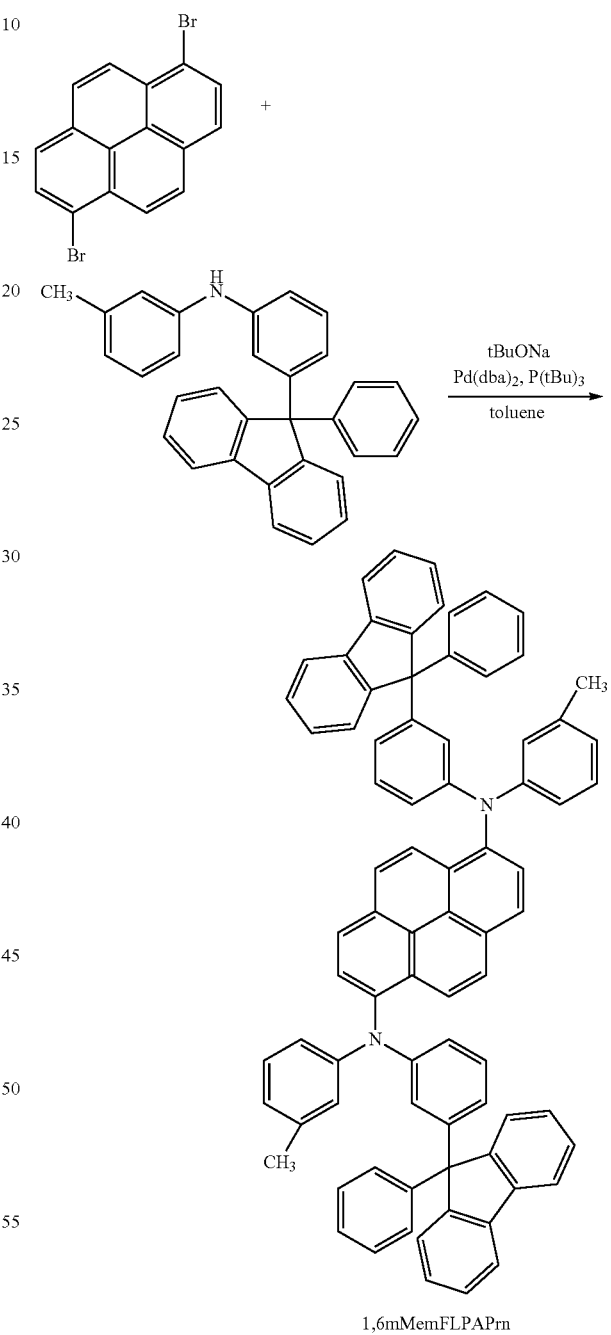

1,6mMemFLPAPrn

A nuclear magnetic resonance (NMR) spectroscopy identified this compound as N,N'-bis(3-methylphenyl)-N,N'-bis[3-(9-phenyl-9H-fluoren-9-yl)phenyl]-pyrene-1,6-diamine (abbreviation: 1,6mMemFLPAPrn), which was the object of the synthesis.

$^1$H NMR data of the obtained compound are shown below.

$^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H).

Reference Example 2

An example of synthesis of 3-[4-(9-phenanthryl)-phenyl]-9-phenyl-9H-carbazole (abbreviation: PCPPn) is described.

Step 1: Synthesis of 4-(9-Phenyl-9H-carbazol-3-yl)phenylboronic acid

In a 300 mL three-neck flask, 8.0 g (20 mmol) of 3-(4-bromophenyl)-9-phenyl-9H-carbazole was placed, the air in the flask was replaced with nitrogen, 100 mL of dehydrated tetrahydrofuran (abbreviation: THF) was added, and the temperature was lowered to −78° C. Into this mixture solution, 15 mL (24 mmol) of a 1.65 mol/L n-butyllithium hexane solution was dropped, and the mixture solution with the n-butyllithium hexane solution added was stirred for 2 hours. To this mixture, 3.4 mL (30 mmol) of trimethyl borate was added, and the mixture was stirred at −78° C. for 2 hours and at room temperature for 18 hours. After the reaction, a 1M diluted hydrochloric acid was added to this reaction solution until the solution became acid, and the solution with the diluted hydrochloric acid added was stirred for 7 hours. This solution was subjected to extraction with ethyl acetate, and the obtained organic layer was washed with a saturated aqueous sodium chloride solution. After the washing, magnesium sulfate was added to the organic layer to adsorb moisture. This suspension was filtered, and the obtained filtrate was concentrated, and hexane was added thereto. The mixture was irradiated with supersonic waves and then recrystallized to give 6.4 g of a white powder, which was the object of synthesis, in a yield of 88%. A reaction scheme of Step 1 described above is illustrated below.

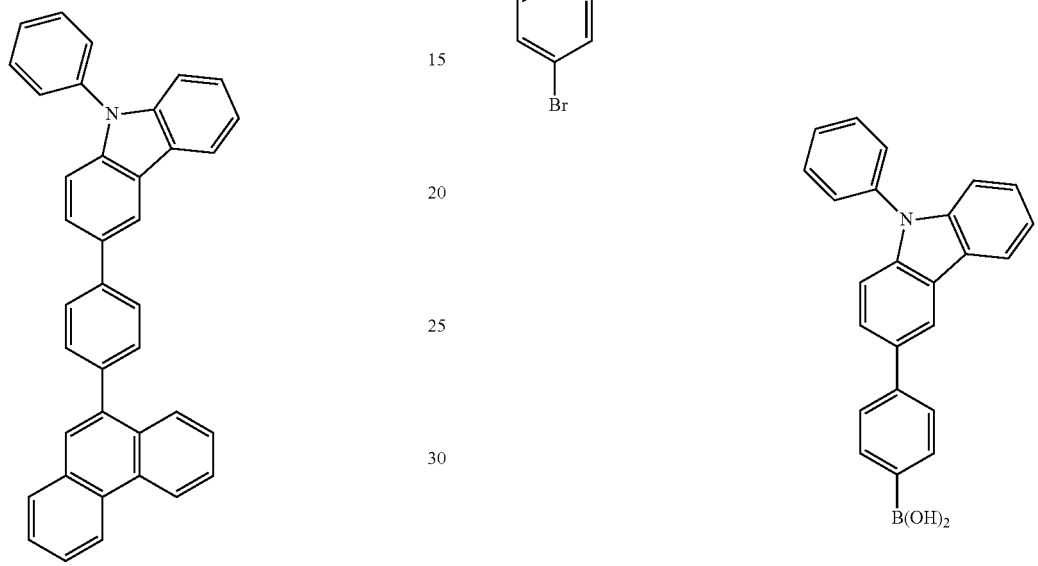

The Rf values of the substance that was the object of synthesis and 3-(4-bromophenyl)-9-phenyl-9H-carbazole were respectively 0 (origin) and 0.53, which were found by silica gel thin layer chromatography (TLC) (developing solvent: ethyl acetate/hexane in a 1:10 ratio). In addition, the Rf values of the object of the synthesis and 3-(4-bromophenyl)-9-phenyl-9H-carbazole were respectively 0.72 and 0.93, which were found by silica gel thin layer chromatography (TLC) using ethyl acetate as a developing solvent.

Step 2: Synthesis of 3-[4-(9-Phenanthryl)-phenyl]-9-phenyl-9H-carbazole (abbreviation: PCPPn)

In a 200 mL three-neck flask, a mixture of 1.5 g (5.0 mmol) of 9-phenyl-9H-carbazol-3-yl-phenyl-4-boronic acid, 3.2 g (11 mmol) of 9-bromophenanthrene, 11 mg (0.1 mmol) of palladium(II)acetate, 30 mg (0.1 mmol) of tri(ortho-tolyl)phosphine, 30 mL of toluene, 3 mL of ethanol, and 5 mL of a 2 mol/L aqueous solution of potassium carbonate was degassed while being stirred under reduced pressure, and reacted by being stirred and heated at 90° C. for 6 hours under a nitrogen atmosphere.

After the reaction, 200 mL of toluene was added to this reaction mixture solution, and the organic layer of the mixture solution was filtered through Florisil, alumina, and Celite. The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and acetone and methanol were added thereto. The mixture was irradiated with ultrasonic waves and then recrystallized, so that PCPPn, which was the object of the synthesis, was obtained as 2.2 g of a white powder in a yield of 75%. A reaction scheme of Step 2 is illustrated below.

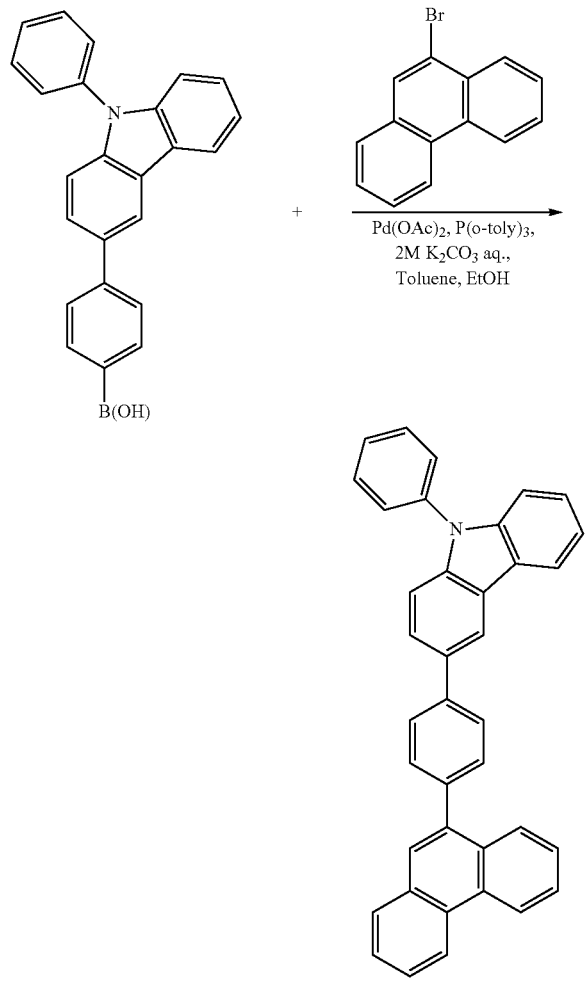

The Rf values of the substance that was the object of the synthesis and 9-bromophenanthrene were respectively 0.33 and 0.70, which were found by silica gel thin layer chromatography (TLC) (developing solvent: ethyl acetate/hexane in a 1:10 ratio).

The obtained compound was subjected to nuclear magnetic resonance (NMR) spectroscopy. The measurement results confirmed that PCPPn was obtained. The measurement data are as follows:

$^1$H NMR (CDCl$_3$, 300 MHz): δ (ppm)=7.30-7.35 (m, 11H), 7.43-7.78 (m, 16H), 7.86-7.93 (m, 3H), 8.01 (dd, J=0.9 Hz, 7.8 Hz, 1H), 8.23 (d, J=7.8 Hz, 1H), 8.47 (d, J=1.5 Hz, 1H), 8.74 (d, J=8.1 Hz, 1H), 8.80 (d, J=7.8 Hz, 1H).

REFERENCE NUMERALS

101: first electrode, 102: second electrode, 103: EL layer, 111: hole-injection layer, 112: hole-transport layer, 113: light-emitting layer, 114: electron-transport layer, 115: electron-injection layer, 400: substrate, 401: first electrode, 402: auxiliary electrode, 403: EL layer, 404: second electrode, 405: sealing material, 406: sealing material, 407: sealing substrate, 408: space, 412: pad, 420: IC chip, 501: first electrode, 502: second electrode, 511: first light-emitting unit, 512: second light-emitting unit, 513: charge generation layer, 601: driver circuit portion (source line driver circuit), 602: pixel portion, 603: driver circuit portion (gate line driver circuit), 604: sealing substrate, 605: sealing material, 607: space, 608: wiring, 609: FPC (flexible printed circuit), 610: element substrate, 611: switching TFT, 612: current control TFT, 613: first electrode, 614: insulator, 616: EL layer, 617: second electrode, 618: light-emitting element, 623: n-channel TFT, 624: p-channel TFT, 901: housing, 902: liquid crystal layer, 903: backlight unit, 904: housing, 905: driver IC, 906: terminal, 951: substrate, 952: electrode, 953: insulating layer, 954: partition layer, 955: EL layer, 956: electrode, 1201: source electrode, 1202: active layer, 1203: drain electrode, 1204: gate electrode, 2001: housing, 2002: light source, 3001: lighting device, 5000: display region, 5001: display region, 5002: display region, 5003: display region, 5004: display region, 5005: display region, 7101: housing, 7103: display portion, 7105: stand, 7107: display portion, 7109: operation key, 7110: remote control, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7401: housing, 7402: display portion, 7403: operation button, 7404: external connection port, 7405: speaker, 7406: microphone, 7400: mobile phone.

This application is based on Japanese Patent Application Serial No. 2011-161161 filed with the Japan Patent Office on Jul. 22, 2011, the entire contents of which are hereby incorporated by reference.

The invention claimed is:

1. A compound comprising:
a dibenzo[c,g]carbazole skeleton; and
an aryl group bonded to a 7-position of the dibenzo[c,g] carbazole skeleton,
wherein the aryl group has 14 to 30 carbon atoms and includes at least an anthracene skeleton, and wherein the anthracene skeleton is bonded to the 7-position of the dibenzo[c,g]carbazole skeleton through a phenylene group.

2. The compound according to claim 1, wherein the 7-position of the dibenzo[c,g]carbazole skeleton and a 9-position of the anthracene skeleton are bonded through the phenylene group.

3. The compound according to claim 1, wherein the aryl group is a substituted or unsubstituted anthryl phenyl group, and wherein the substituted or unsubstituted anthryl phenyl group has 20 to 30 carbon atoms.

4. The compound according to claim 1, wherein the aryl group is a substituted or unsubstituted (9-anthryl)phenyl group, and wherein the substituted or unsubstituted (9-anthryl)phenyl group has 20 to 30 carbon atoms.

5. A light-emitting element comprising a dibenzo[c,g]carbazole compound comprising:
a dibenzo[c,g]carbazole skeleton; and an aryl group bonded to a 7-position of the dibenzo[c,g]carbazole skeleton,
wherein the aryl group has 14 to 30 carbon atoms and includes at least an anthracene skeleton, and
wherein the anthracene skeleton is bonded to the 7-position of the dibenzo[c,g]carbazole skeleton through a phenylene group.

6. The light-emitting element according to claim 5, wherein the 7-position of the dibenzo[c,g]carbazole skeleton and a 9-position of the anthracene skeleton are bonded through the phenylene group.

7. The light-emitting element according to claim 5, wherein the aryl group is a substituted or unsubstituted anthryl phenyl group, and wherein the substituted or unsubstituted anthryl phenyl group has 20 to 30 carbon atoms.

8. The light-emitting element according to claim 5, wherein the aryl group is a substituted or unsubstituted (9-anthryl)phenyl group, and wherein the substituted or unsubstituted (9-anthryl)phenyl group has 20 to 30 carbon atoms.

9. A lighting device comprising the light-emitting element according to claim 5.

10. A display device comprising the light-emitting element according to claim 5.

11. A compound represented by a general formula (G2),

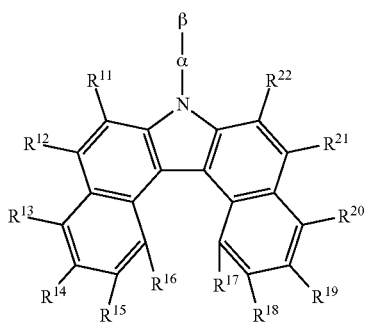

(G2)

wherein α represents a substituted or unsubstituted phenylene group,
wherein β represents a substituted or unsubstituted anthryl group, and
wherein $R^{11}$ to $R^{22}$ each independently represent any of hydrogen, an alkyl group having 1 to 4 carbon atoms, and an aryl group having 6 to 12 carbon atoms.

12. The compound according to claim 11, wherein the compound is represented by a general formula (G3),

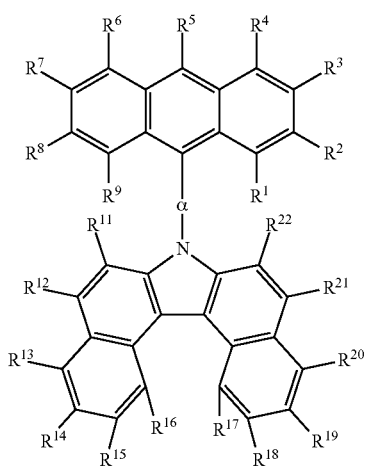

(G3)

wherein $R^5$ represents any of hydrogen, an alkyl group having 1 to 4 carbon atoms, and an aryl group having 6 to 10 carbon atoms, wherein $R^1$, $R^2$, $R^3$, $R^4$, $R^6$, $R^7$, $R^8$, and $R^9$ each independently represent hydrogen or an alkyl group having 1 to 4 carbon atoms, and wherein α represents a substituted or unsubstituted phenylene group.

13. The compound according to claim 11,

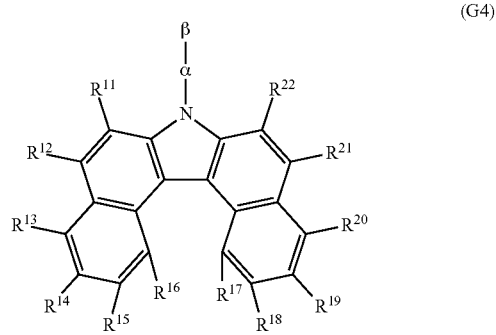

(G4)

wherein a total number of carbon atoms of α and β is 20 to 30.

14. The compound according to claim 11, wherein the compound is represented by a general formula (G5),

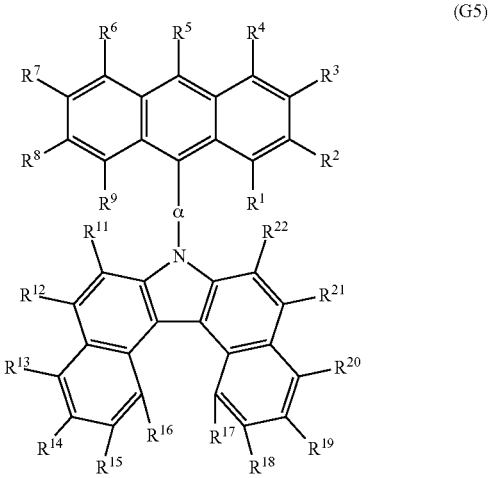

(G5)

wherein $R^5$ represents any of hydrogen, an alkyl group having 1 to 4 carbon atoms, and an aryl group having 6 to 10 carbon atoms, wherein $R^1$, $R^2$, $R^3$, $R^4$, $R^6$, $R^7$, $R^8$, and $R^9$ each independently represent hydrogen or an alkyl group having 1 to 4 carbon atoms, wherein α represents a substituted or unsubstituted phenylene group, and wherein a total number of carbon atoms of $R^1$ to $R^9$ and α is greater than or equal to 6 and less than or equal to 16.

15. The compound according to claim 11, wherein the compound is represented by a general formula (G6), (G6)

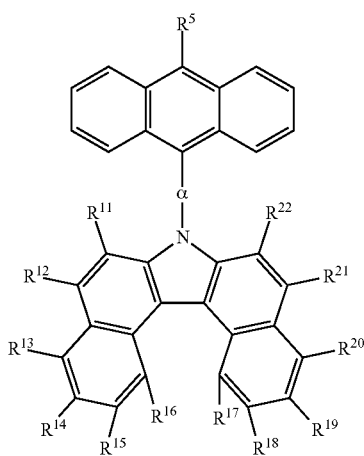

wherein α represents a substituted or unsubstituted phenylene group, wherein $R^5$ represents any of hydrogen, an alkyl group having 1 to 4 carbon atoms, and an aryl group having 6 to 10 carbon atoms, and wherein a total number of carbon atoms of $R^5$ and α is greater than or equal to 6 and less than or equal to 16.

16. The compound according to claim 11, wherein the compound is represented by a general formula (G7), (G7)

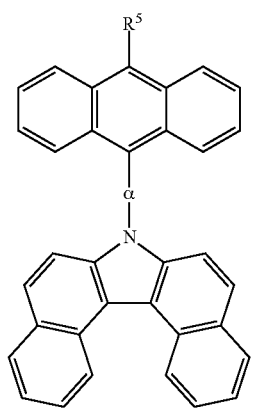

wherein α represents a substituted or unsubstituted phenylene group, wherein $R^5$ represents any of hydrogen, an alkyl group having 1 to 4 carbon atoms, and an aryl group having 6 to 10 carbon atoms, and wherein a total number of carbon atoms of $R^5$ and α is greater than or equal to 6 and less than or equal to 16.

17. The compound according to claim 11, wherein the compound is represented by a structural formula (100), (100)

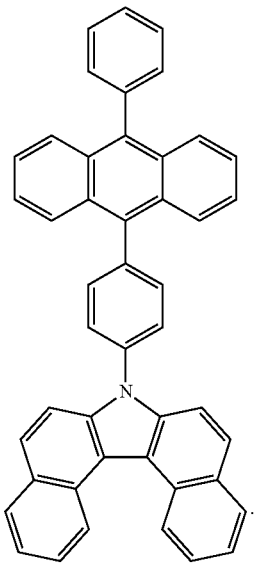

18. The compound according to claim 11, the compound is represented by a structural formula (127), (127)

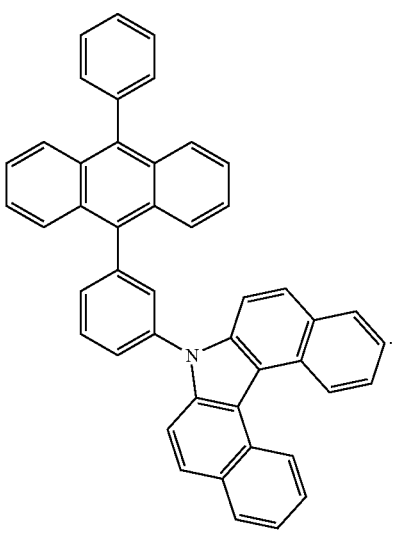

19. A light-emitting element comprising:
a first electrode;
a light-emitting layer over the first electrode; and
a second electrode over the light-emitting layer,
wherein the light-emitting layer comprises the compound according to claim 11.

20. A lighting device comprising the light-emitting element according to claim 19.

21. A display device comprising the light-emitting element according to claim 19.

* * * * *